(12) United States Patent
Kim et al.

(10) Patent No.: US 11,173,192 B2
(45) Date of Patent: Nov. 16, 2021

(54) ANTI-RNA VIRUS COMPOSITION COMPRISING EPRS PROTEIN OR FRAGMENT THEREOF

(71) Applicants: KOREA RESEARCH INSTITUTE OF BIOSCIENCE AND BIOTECHNOLOGY, Daejeon (KR); MEDICINAL BIOCONVERGENCE RESEARCH CENTER, Gyeonggi-do (KR)

(72) Inventors: Myung Hee Kim, Daejeon (KR); Eun Young Lee, Daejeon (KR); Sung Hoon Kim, Gyeonggi-do (KR); Chul Ho Lee, Daejeon (KR)

(73) Assignees: Korea Research Institute of Bioscience and Biotechnology, Daejeon (KR); Medicinal Bioconvergence Research Center, Gyeonngi-do (KR)

( * ) Notice: Subject to any disclaimer, the term of this patent is extended or adjusted under 35 U.S.C. 154(b) by 0 days.

(21) Appl. No.: 16/283,121

(22) Filed: Feb. 22, 2019

(65) Prior Publication Data
US 2019/0321455 A1    Oct. 24, 2019

Related U.S. Application Data

(63) Continuation-in-part of application No. PCT/KR2017/009224, filed on Aug. 23, 2017.

(30) Foreign Application Priority Data

Aug. 23, 2016  (KR) .......................... 10-2016-0107037

(51) Int. Cl.
*A61K 38/53*    (2006.01)
*A61K 47/64*    (2017.01)

(52) U.S. Cl.
CPC .............. *A61K 38/53* (2013.01); *A61K 47/64* (2017.08); *C12Y 601/01018* (2013.01)

(58) Field of Classification Search
CPC ......... A61K 38/53; A61K 47/64; A61P 31/14; C12N 9/93; C12Y 601/01015;
(Continued)

(56) References Cited

U.S. PATENT DOCUMENTS 7,248,971 B1    7/2007  Rigoutsos et al.
9,062,301 B2 *  6/2015  Greene .............. A61K 39/3955
(Continued)

FOREIGN PATENT DOCUMENTS

JP    2005-533793 A    11/2005
JP    2013-531478 A    8/2013
(Continued)

OTHER PUBLICATIONS

Xing et al., Foreign RNA Induces the Degradation of Mitochondrial Antiviral Signaling Protein (MAVS): The Role of Intracellular Antiviral Factors, PLoS ONE 7(9):e45136 (9 pages), also available at https://doi.org/10.1371/journal.pone.0045136 (Sep. 17, 2012) (Year: 2012).*

(Continued)

*Primary Examiner* — Randall L Beane
(74) *Attorney, Agent, or Firm* — Morgan, Lewis & Bockius LLP

(57) ABSTRACT

The present invention relates to an EPRS (glutamyl-prolyl-tRNA synthetase) protein or a fragment thereof.
The EPRS protein of the present invention or fragment thereof may bind to PCBP2 protein to activate the MAVS signaling pathway, and thus it has anti-RNA viral effects, thereby being effective for preventing or treating a RNA viral infectious disease.

19 Claims, 76 Drawing Sheets

Specification includes a Sequence Listing.

(58) Field of Classification Search
CPC .... C12Y 601/01017; C12Y 601/01018; Y02A 50/385; Y02A 50/387; Y02A 50/389
See application file for complete search history.

(56) References Cited

U.S. PATENT DOCUMENTS

| | | | | |
|---|---|---|---|---|
| 2013/0224173 A1* | 8/2013 | Greene | ............... | A61P 3/00 424/94.5 |
| 2015/0064188 A1* | 3/2015 | Greene | .......... | C12Y 601/01021 424/139.1 |

FOREIGN PATENT DOCUMENTS

| | | |
|---|---|---|
| WO | 03/106479 A2 | 12/2003 |
| WO | 2011/140266 A2 | 11/2011 |

OTHER PUBLICATIONS

McGivern et al., Virus-specific mechanisms of carcinogenesis in hepatitis C virus associated liver cancer, Oncogene, vol. 30:1969-1983 (2011) (Year: 2011).*
Vazquez et al., MAVS Coordination of Antiviral Innate Immunity, Journal of Virology, vol. 89(14):6974-6977 (online Jun. 18, 2015) (Year: 2015).*
Agnello et al., Hepatitis C virus and other Flaviviridae viruses enter cells via low density lipoprotein receptor, PNAS, vol. 96(22): 12766-12771 (Oct. 26, 1999) (Year: 1999).*
NCBI, GenBank accession No. AAI26276.1 (2006).
Zhong et al., "Recent Progress in Studies of Arterivirus- and Coronavirus-Host Interactions," Viruses, 4: 980-1010 (2012).
Lee et al., "Infection-specific phosphorylation of glutamyl-prolyl tRNA synthetase induces antiviral immunity," Nature Immunology, 17: 1252-1262 (Nov. 2016).
Sampath et al., "Noncanonical Function of Flutamyl-Prolyl-tRNA Synthetase: Gene-Specific Silencing of Translation," Cell, 119: 195-208 (2004).
Ray et al., 'Macromolecular complexes as depots for releasable regulatory proteins', Trends in Biochemical Sciences, 32: 158-164 (2007).
Mukhopadhyay et al., "The GAIT system: a gatekeeper of inflammatory gene expression," Trends in Biochemical Sciences, 34: 324-331 (2009).
Akira et al., "Pathogen Recognition and Innate Immunity," Cell,124: 783-801 (2006).
International Search Report issued in related International Patent Application No. PCT/KR2017/009224 dated Feb. 12, 2018.
EPRS protein [*Homo sapiens*],Oct. 23, 2006,GenBank AAI26276.1.

* cited by examiner

[FIG. 1]
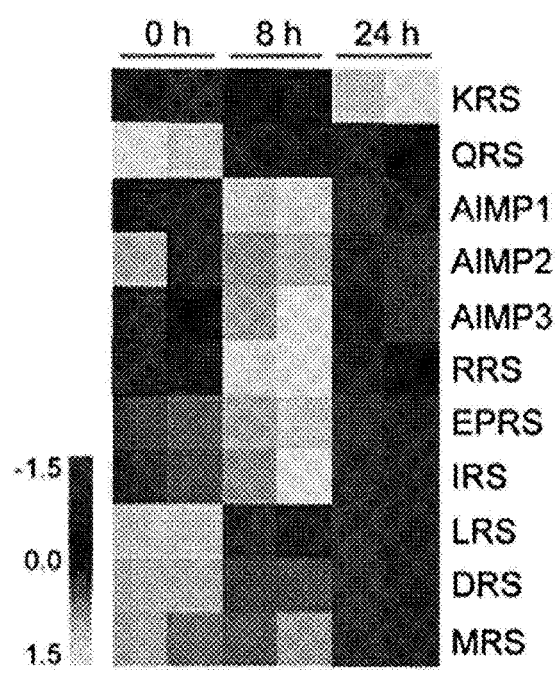

[FIG. 2]
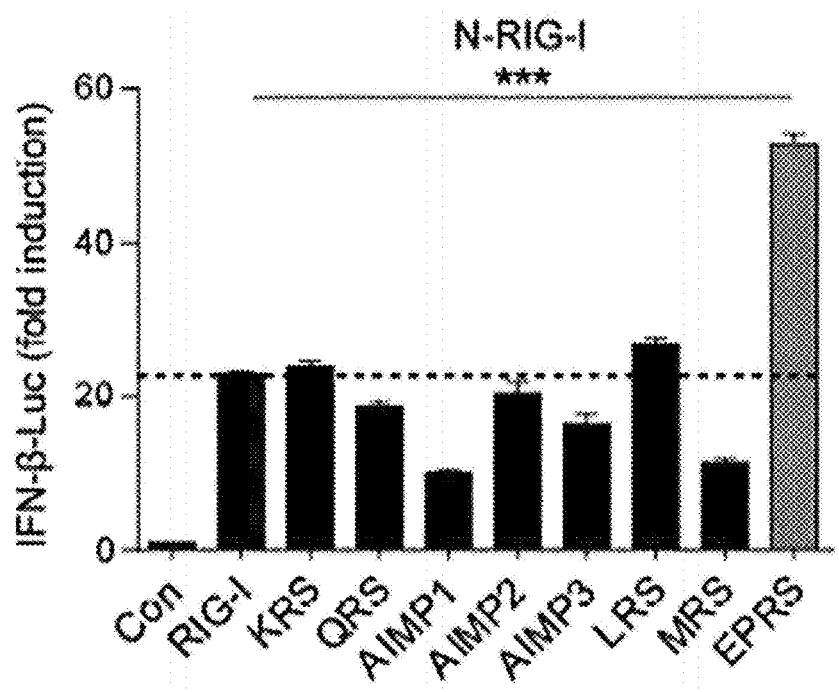

[FIG. 3]
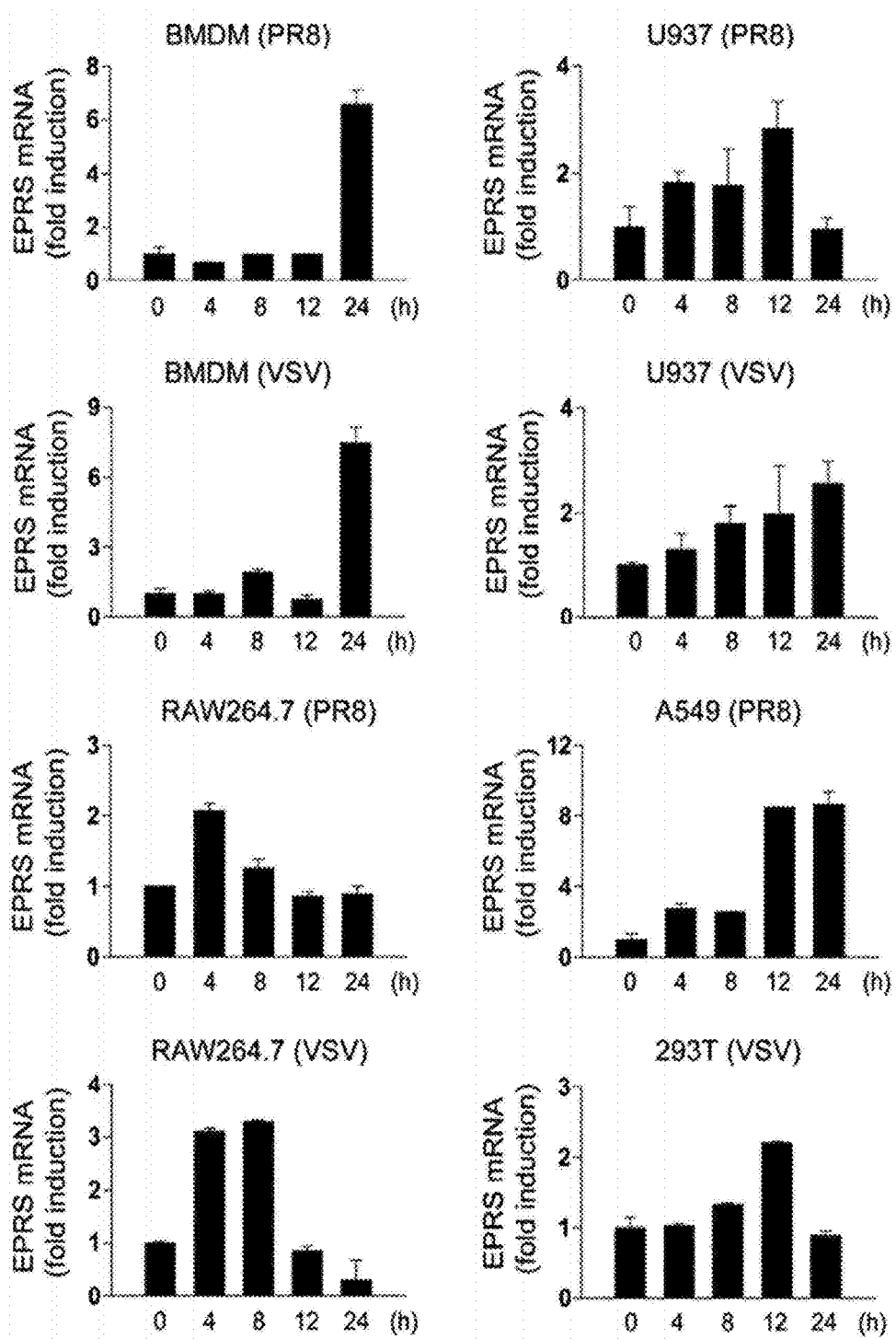

[FIG. 4]
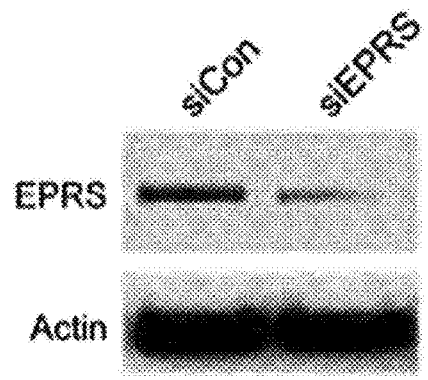
[FIG. 5]
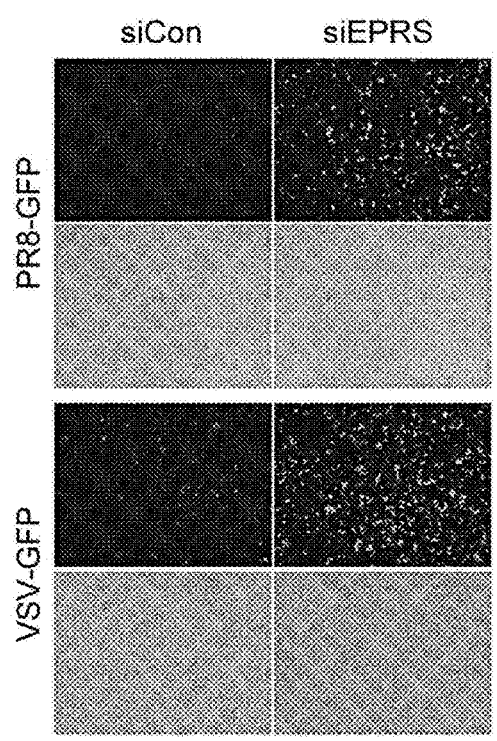

[FIG. 6]
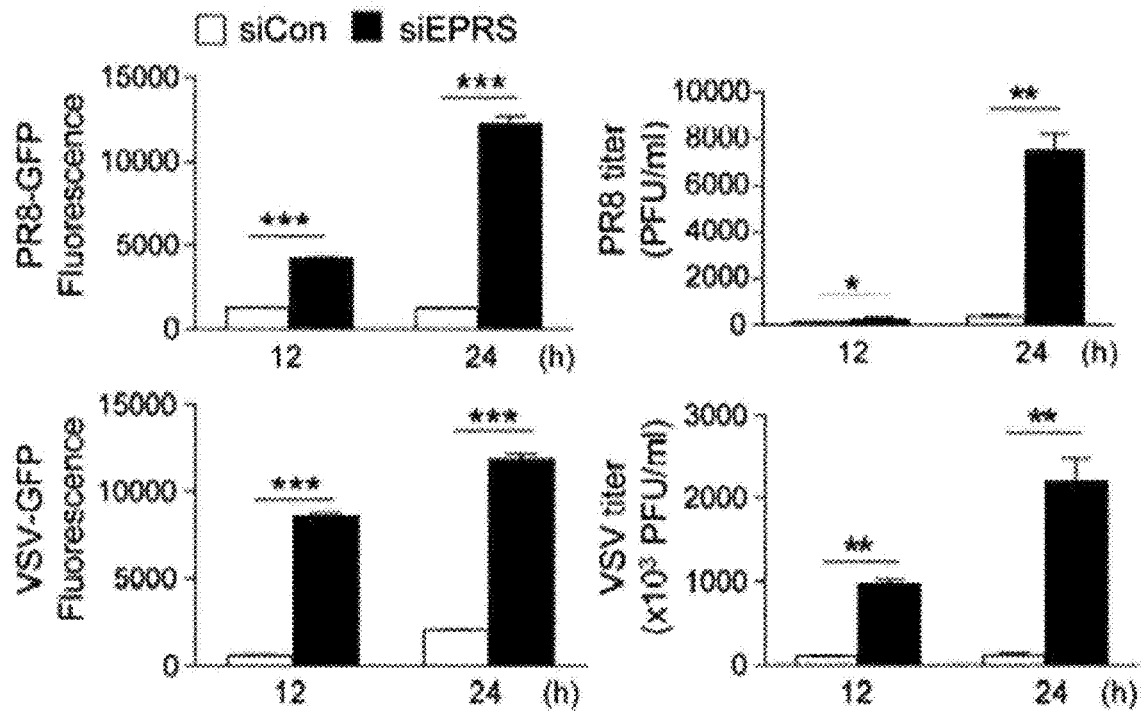
[FIG. 7]
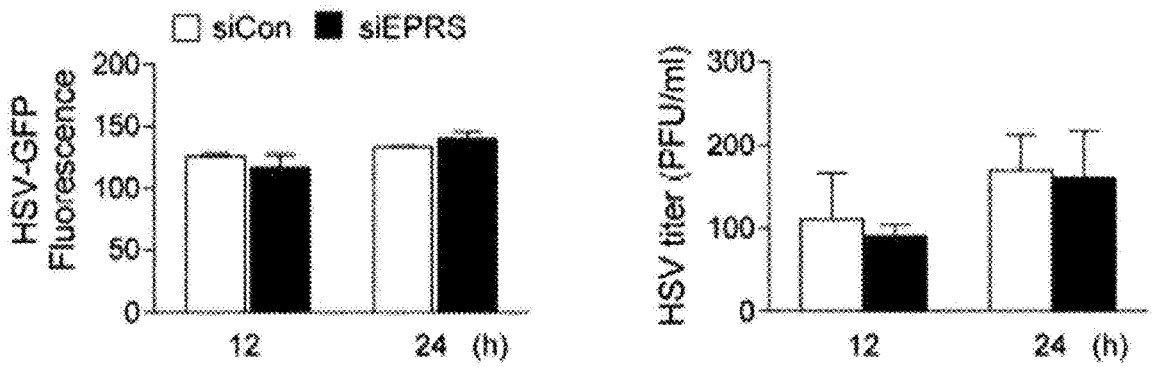

[FIG. 8]
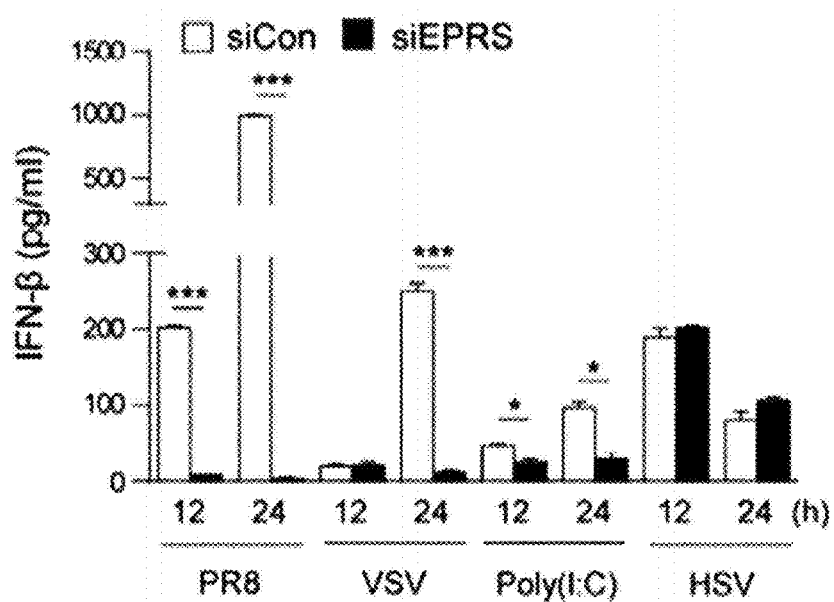
[FIG. 9]
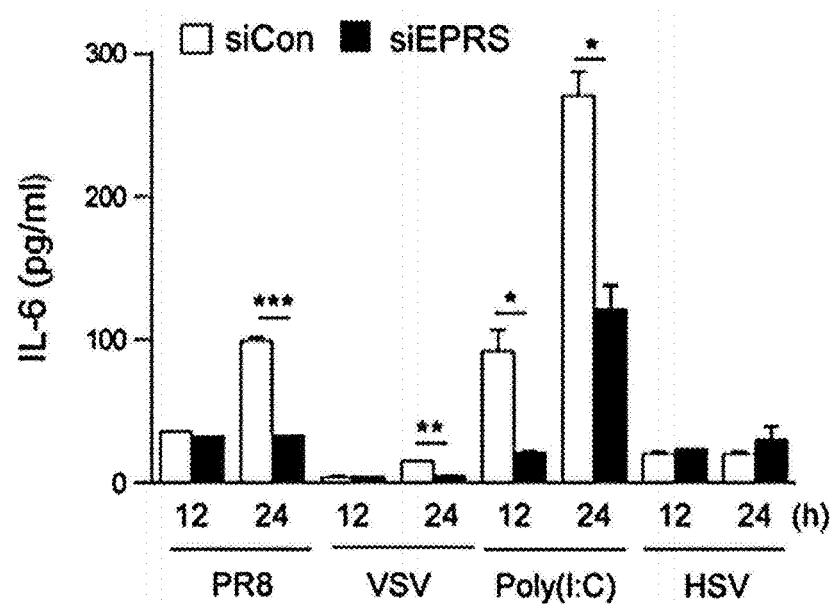

[FIG. 10]
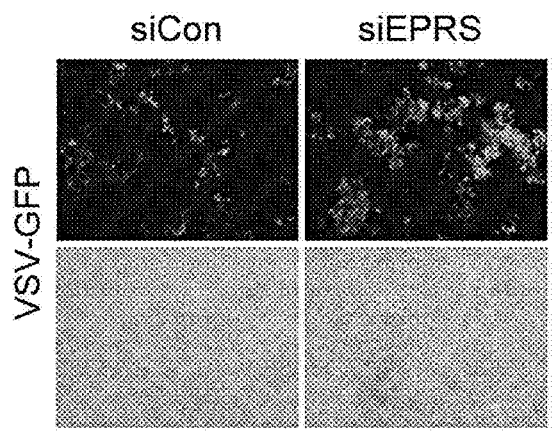
[FIG. 11]
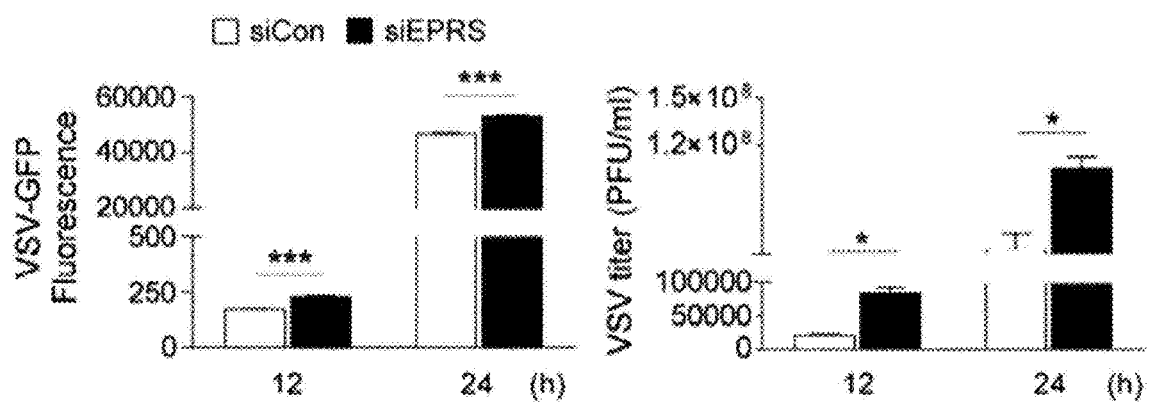
[FIG. 12]
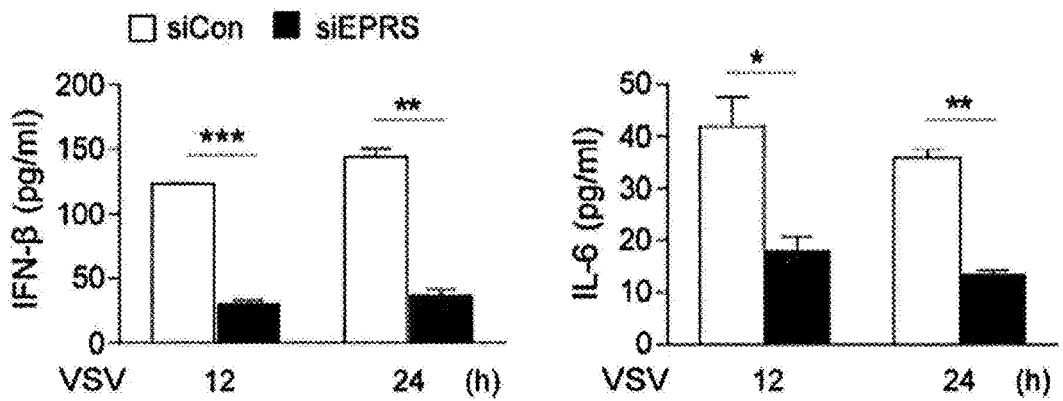

【FIG. 13】
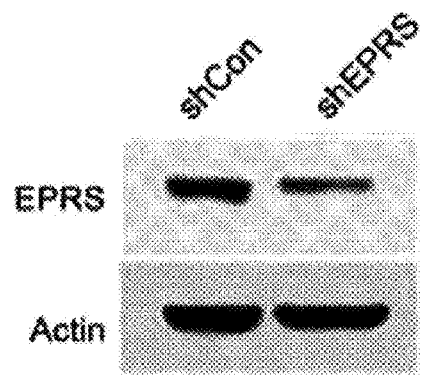
【FIG. 14】
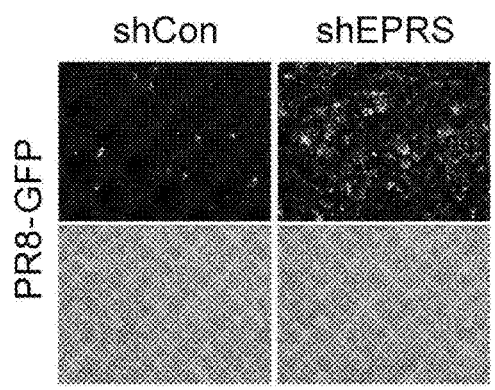
【FIG. 15】
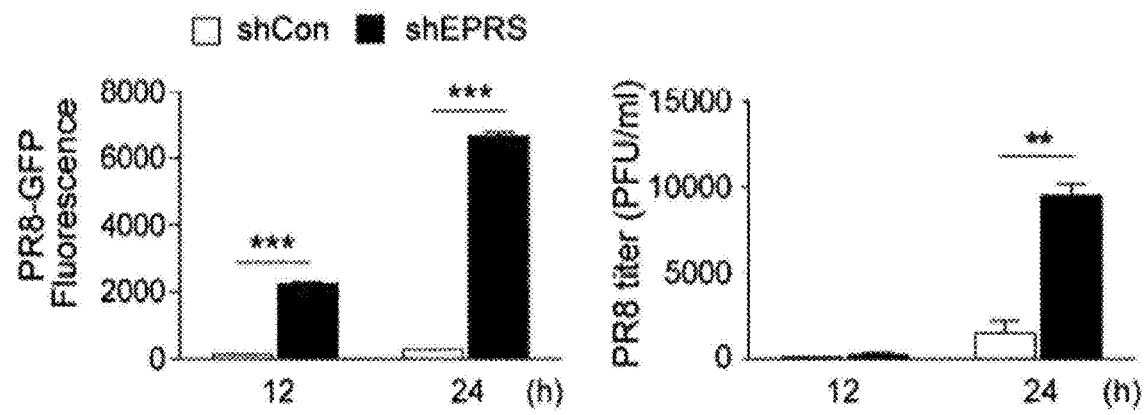

[FIG. 16]
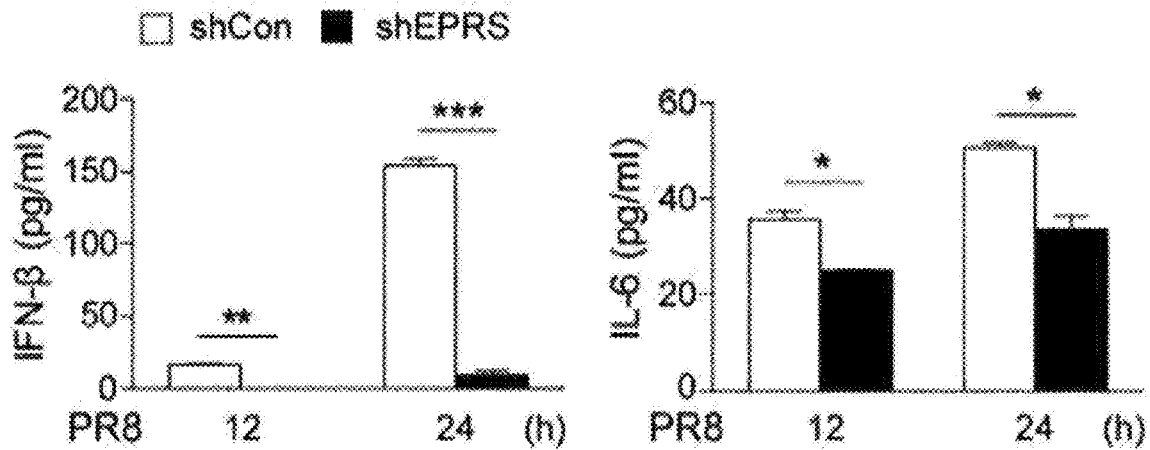
[FIG. 17]
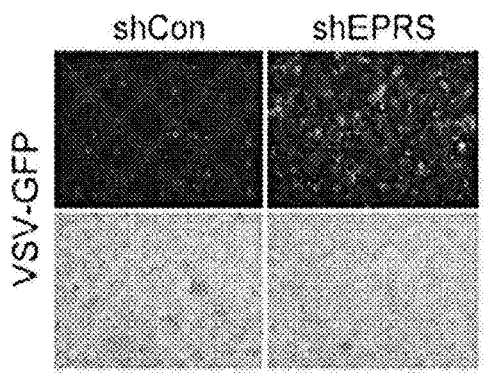
[FIG. 18]
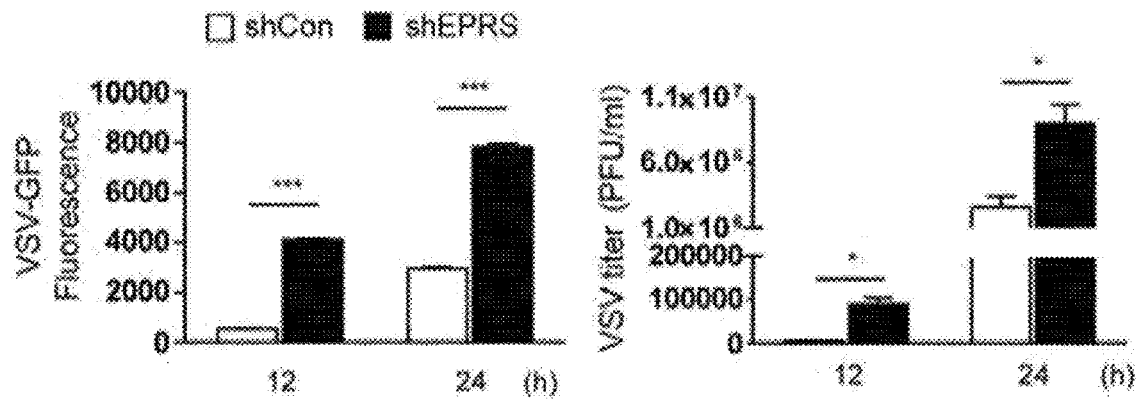

[FIG. 19]
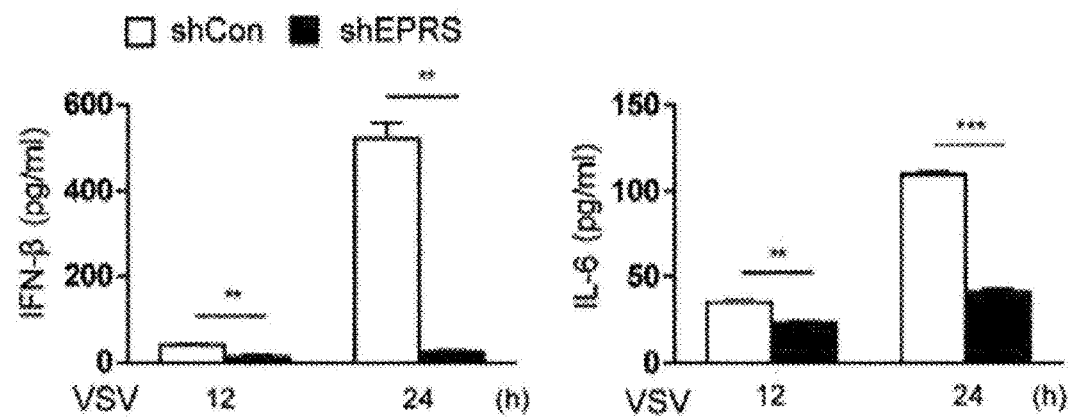
[FIG. 20]
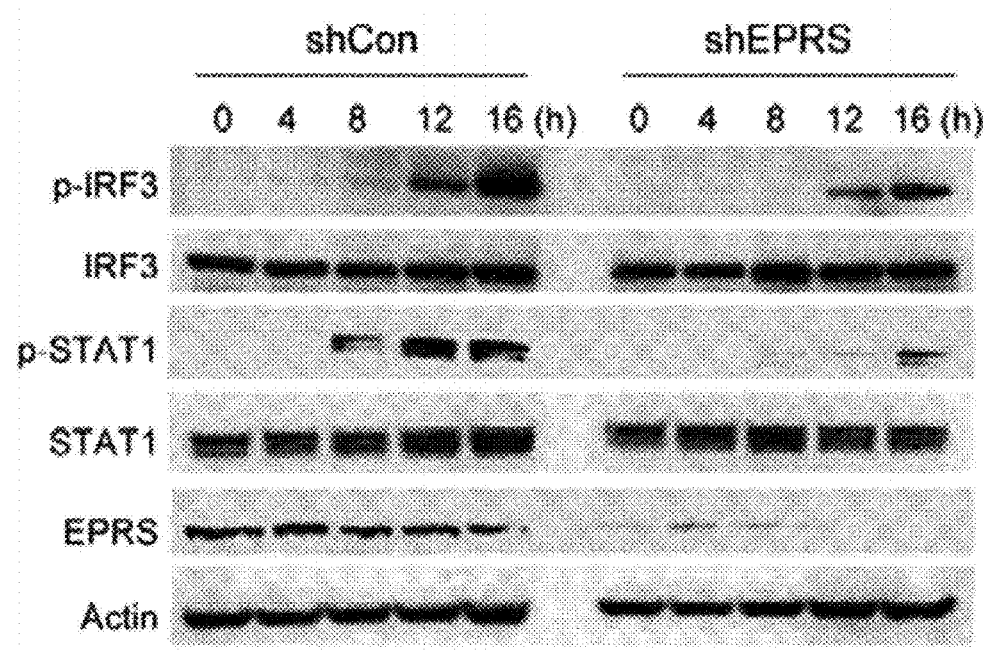

[FIG. 21]
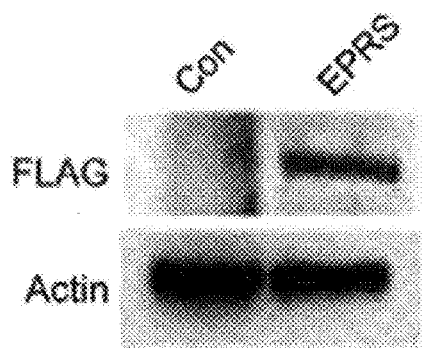
[FIG. 22]
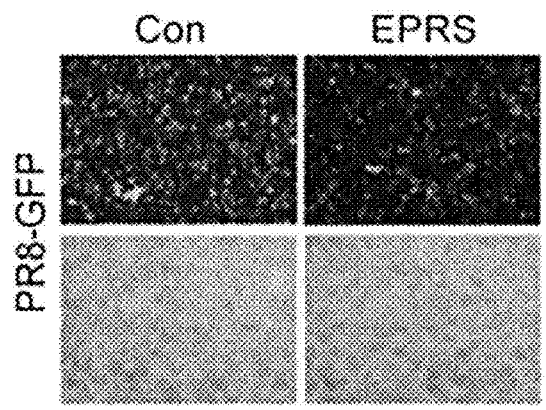
[FIG. 23]
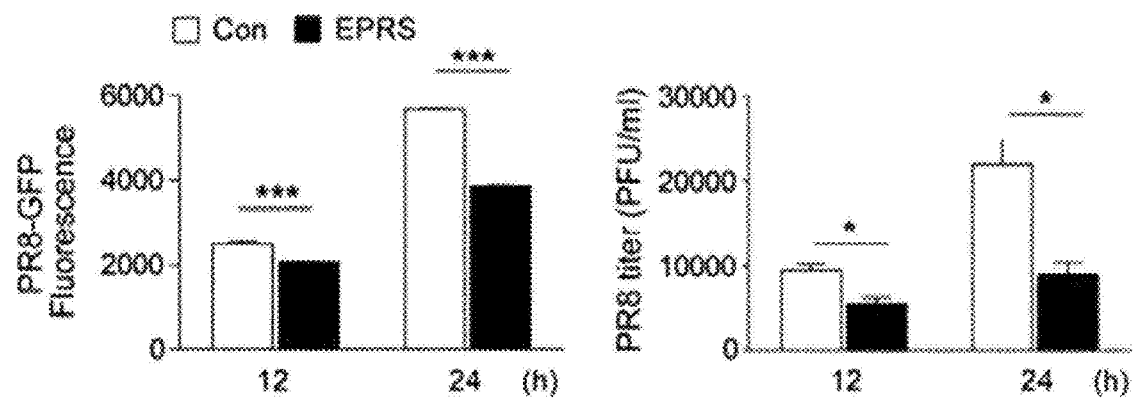

[FIG. 24]
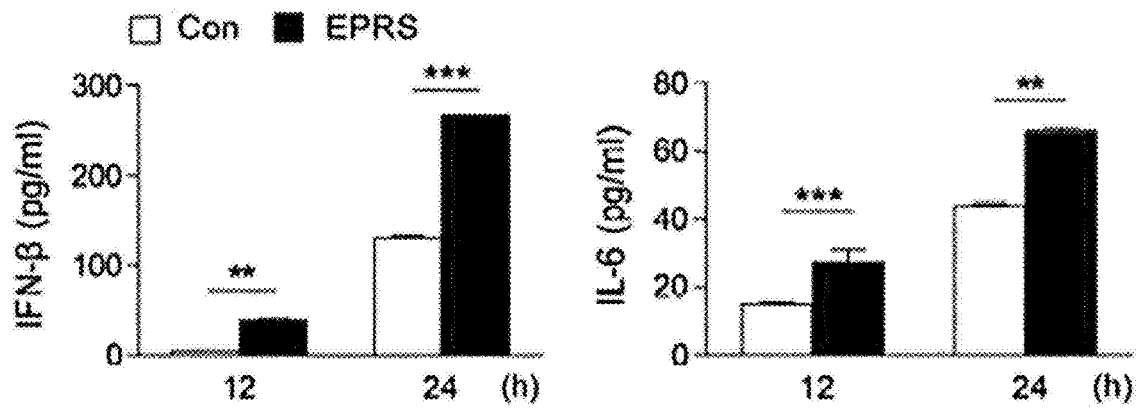
[FIG. 25]
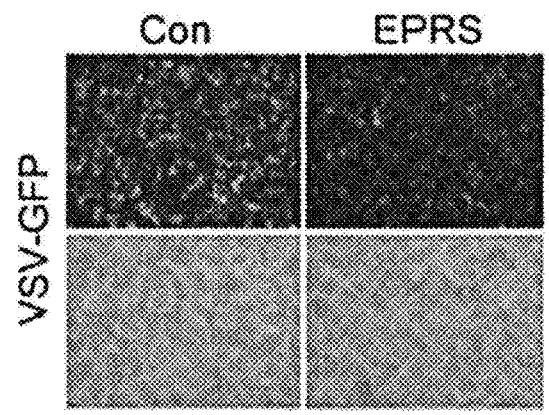
[FIG. 26]
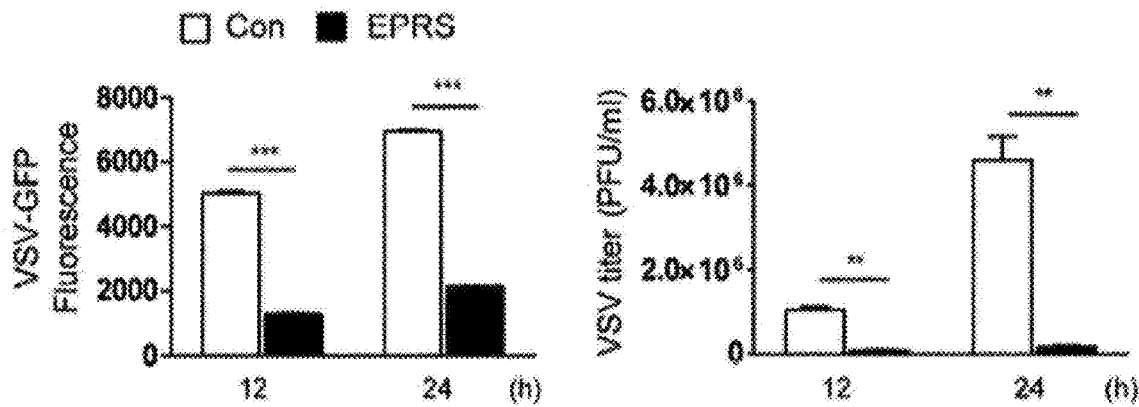

[FIG. 27]
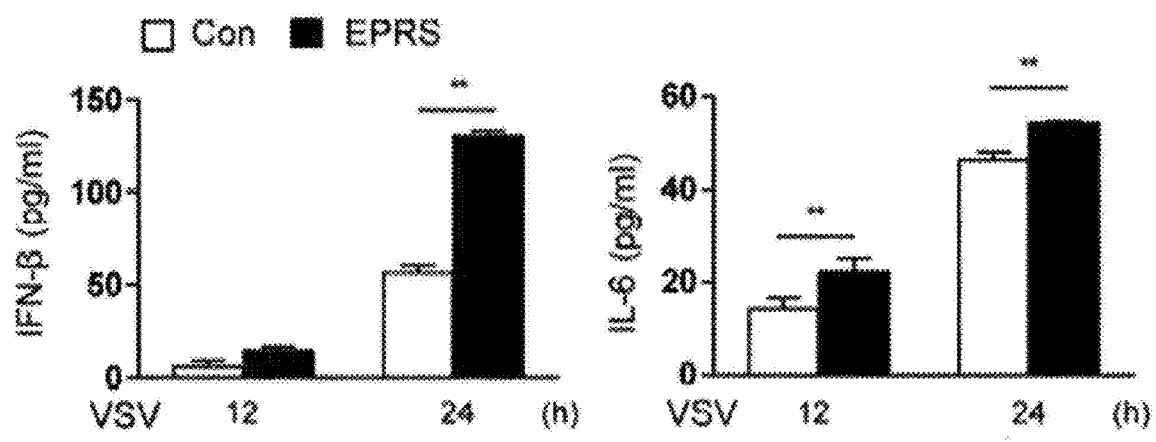

[FIG. 28]
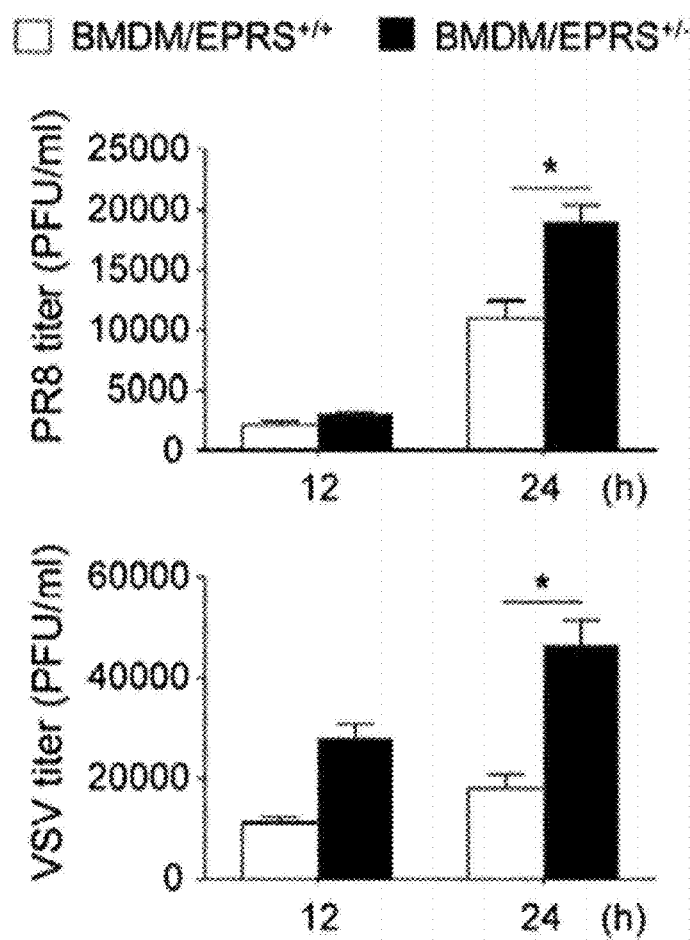

[FIG. 29]
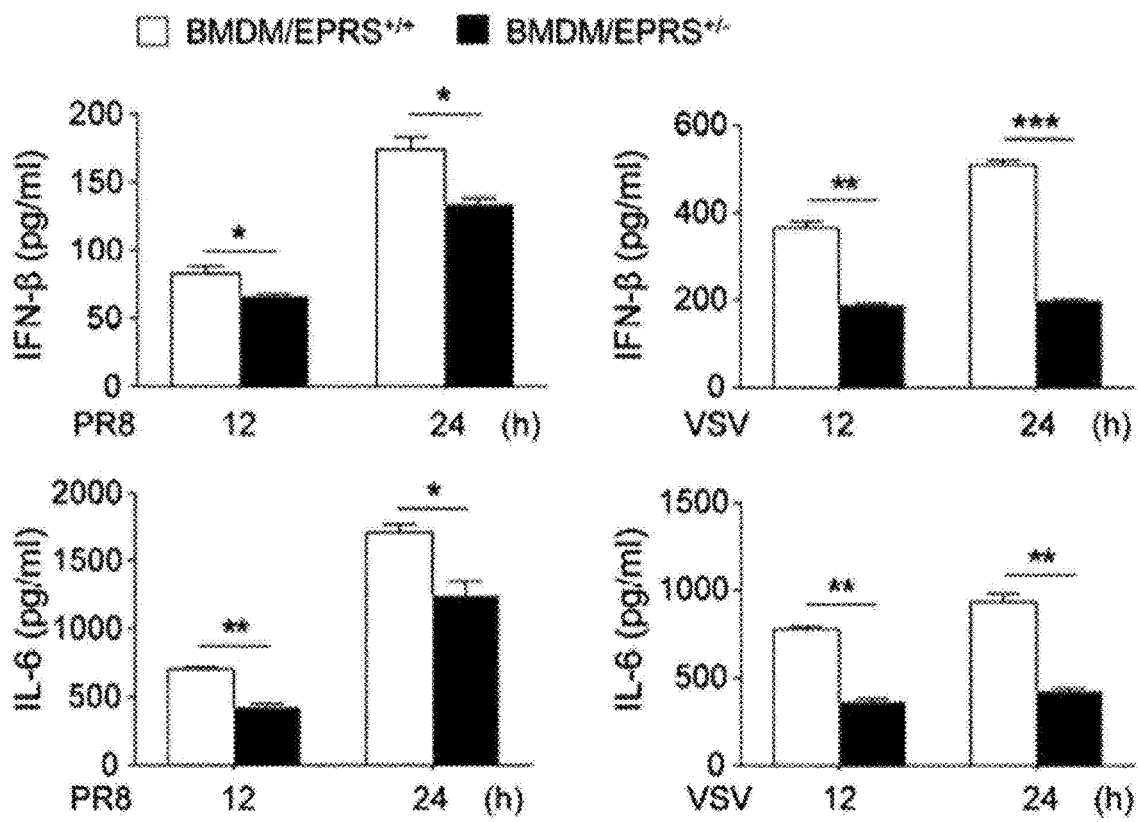

[FIG. 30]
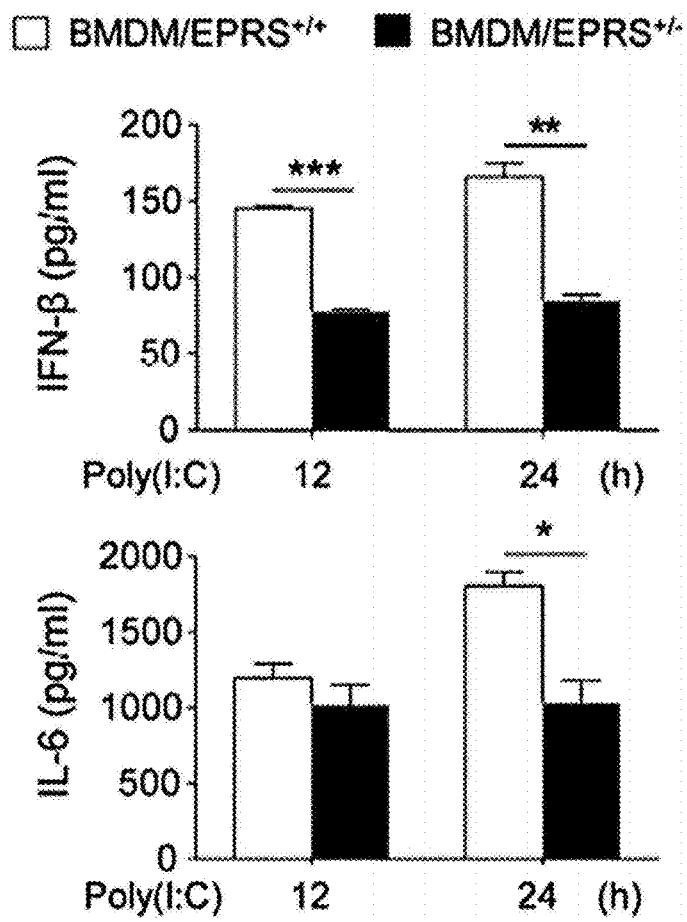

[FIG. 31]
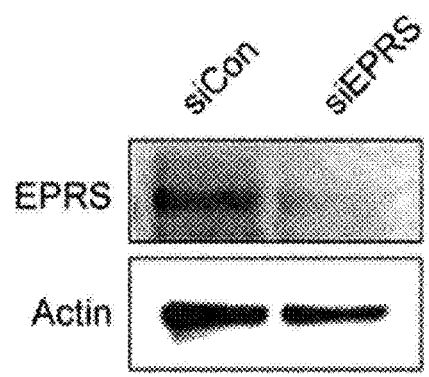
[FIG. 32]
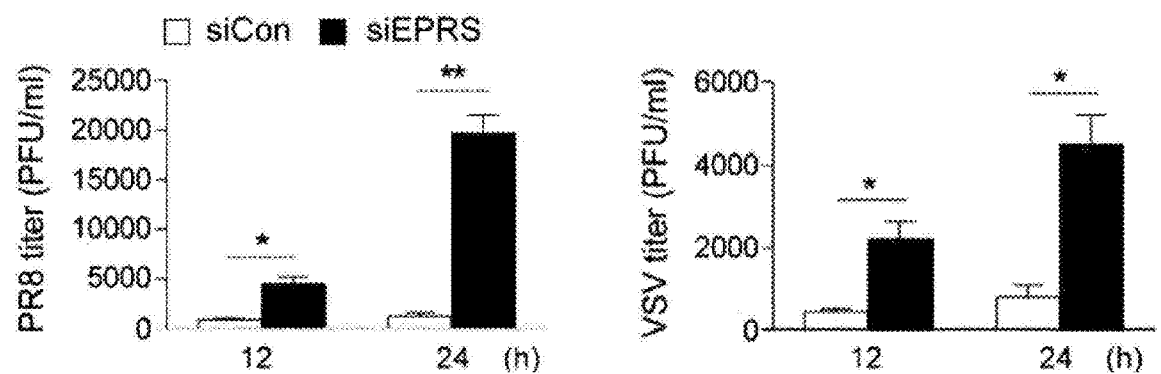

[FIG. 33]
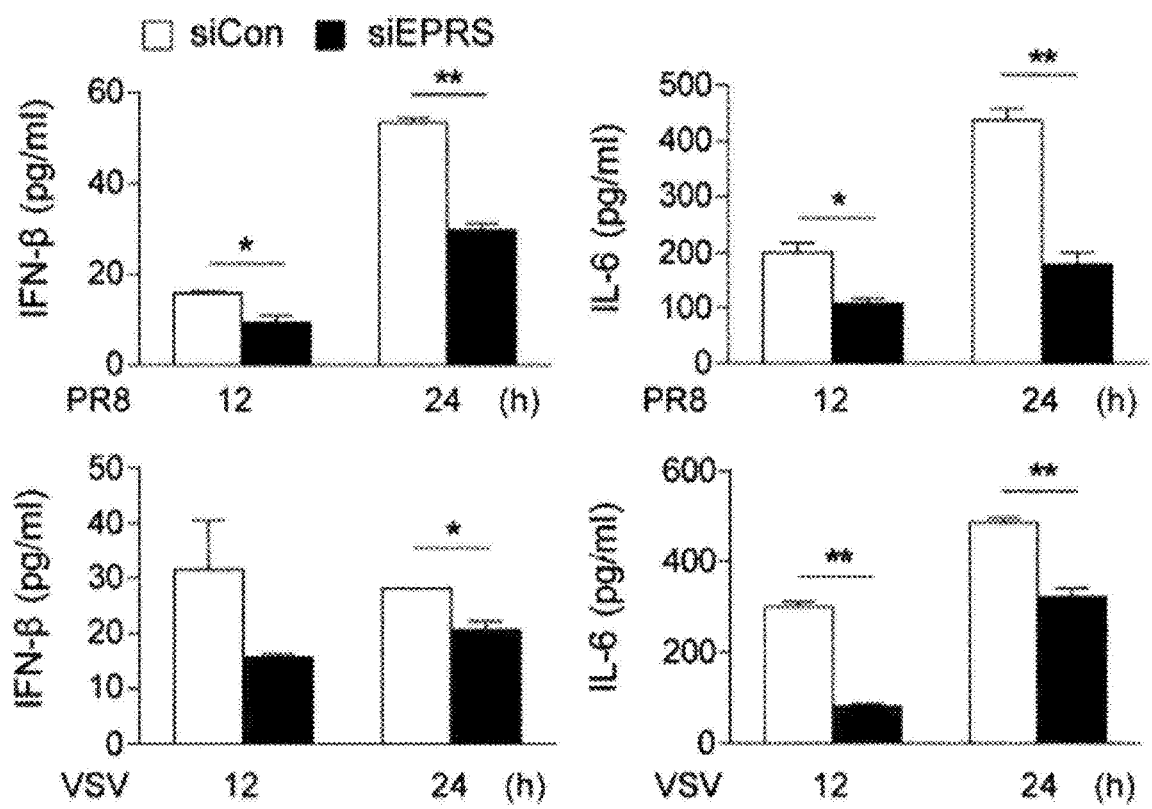

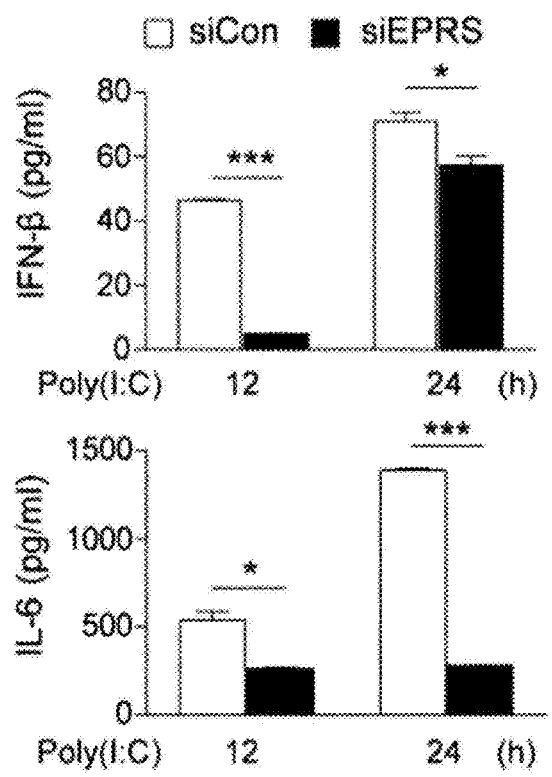
[FIG. 34]

[FIG. 35]
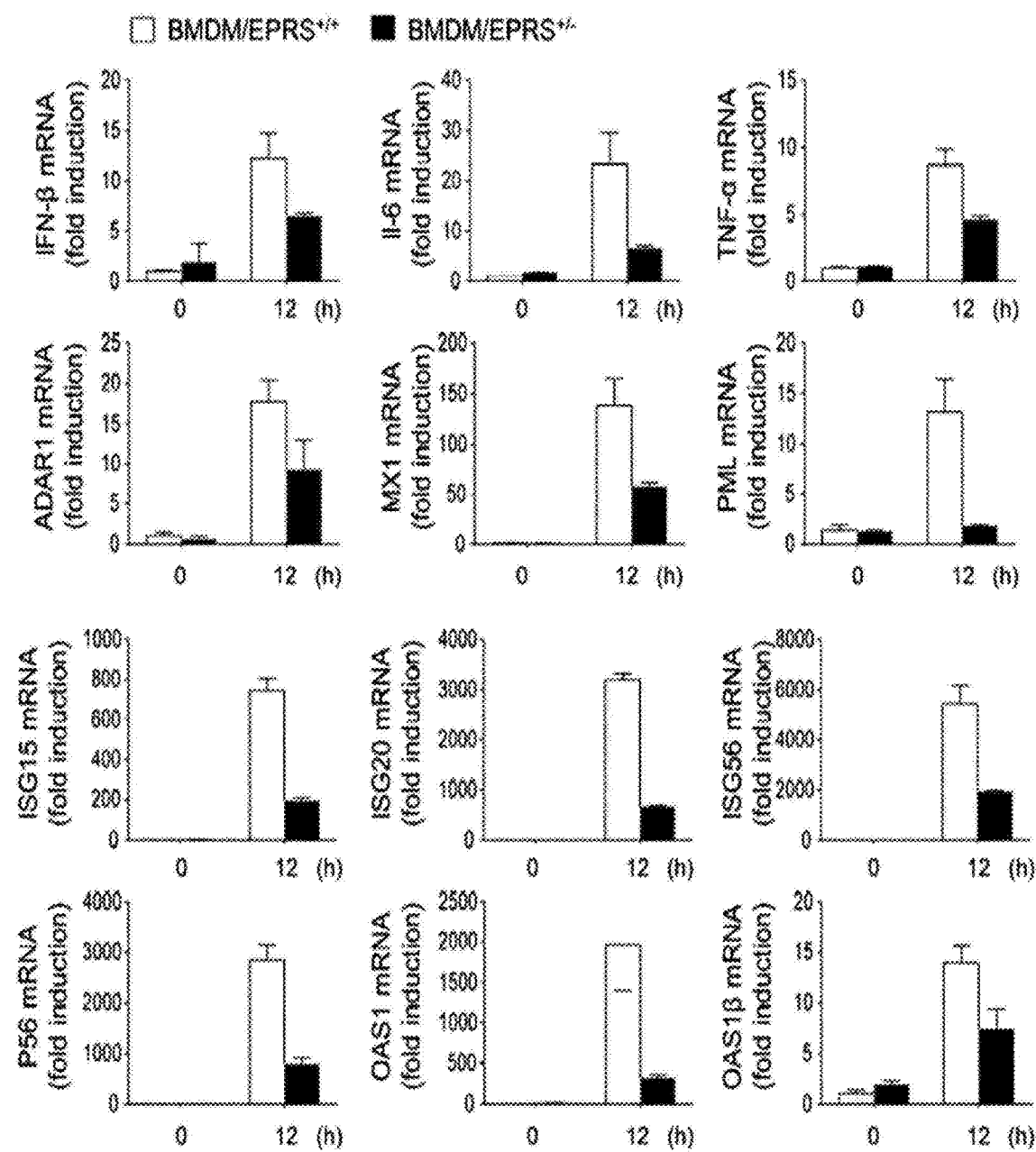

【FIG. 36】
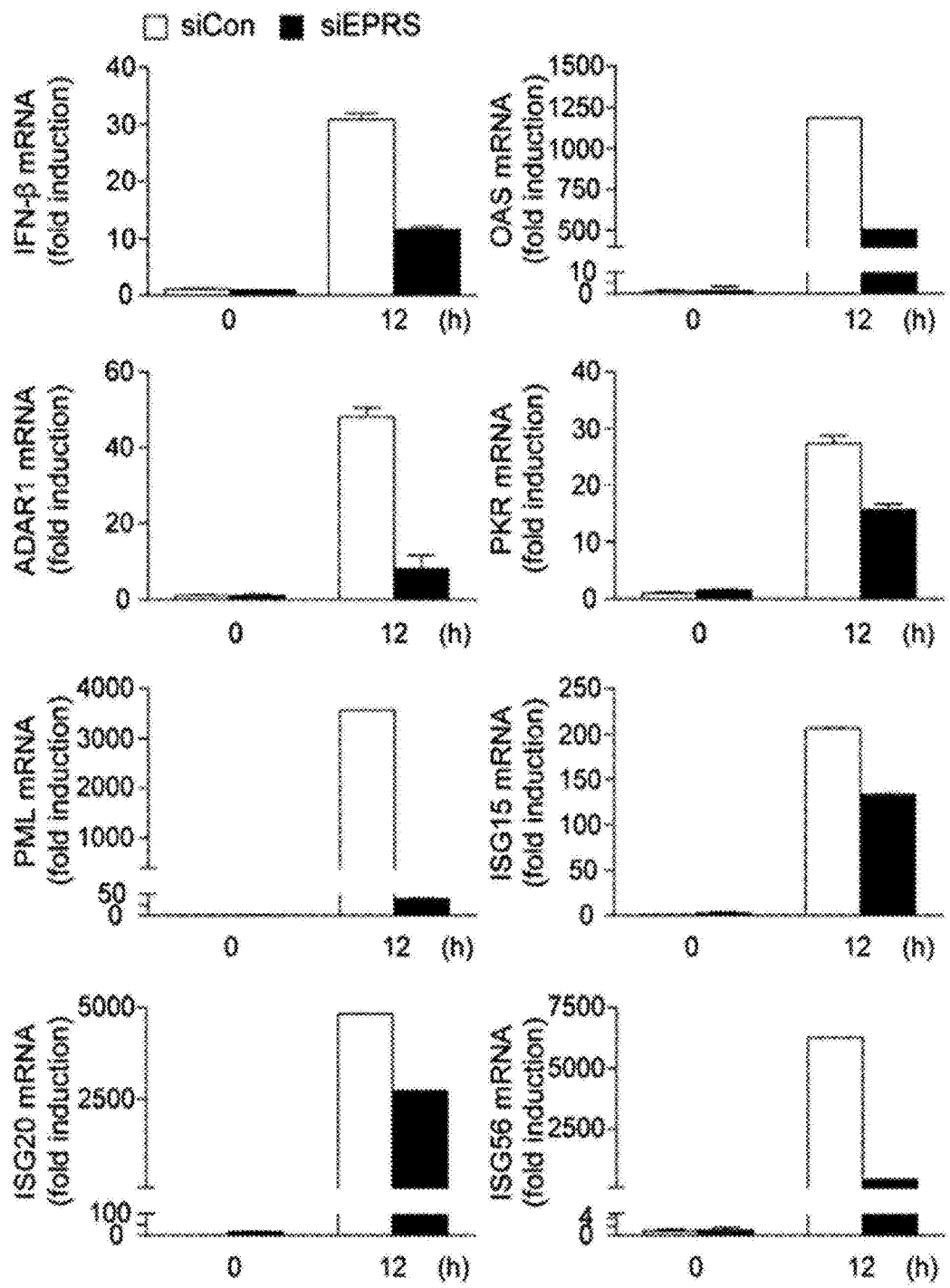

[FIG. 37]
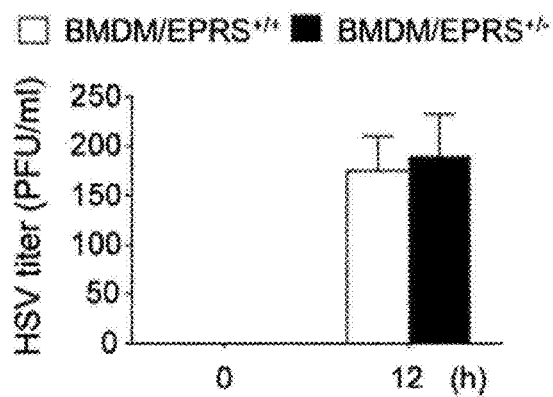
[FIG. 38]
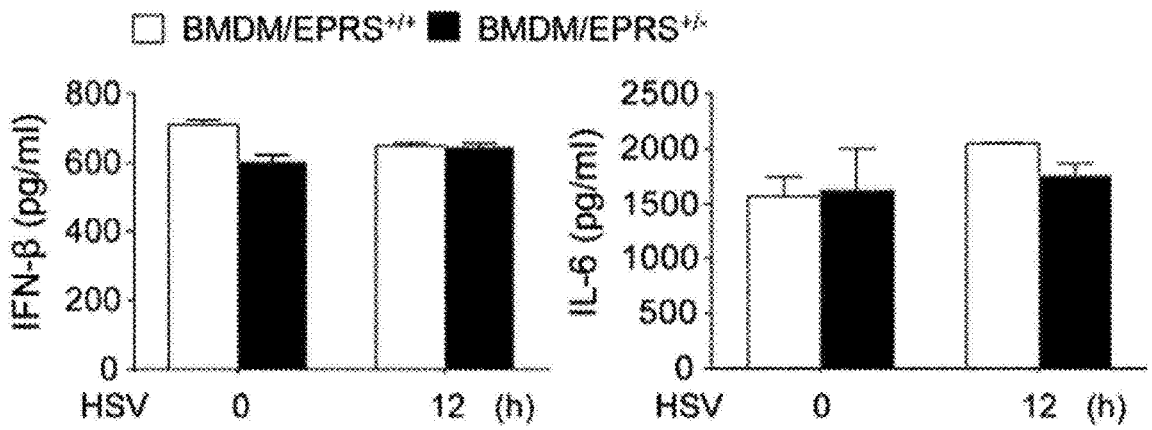

[FIG. 39]
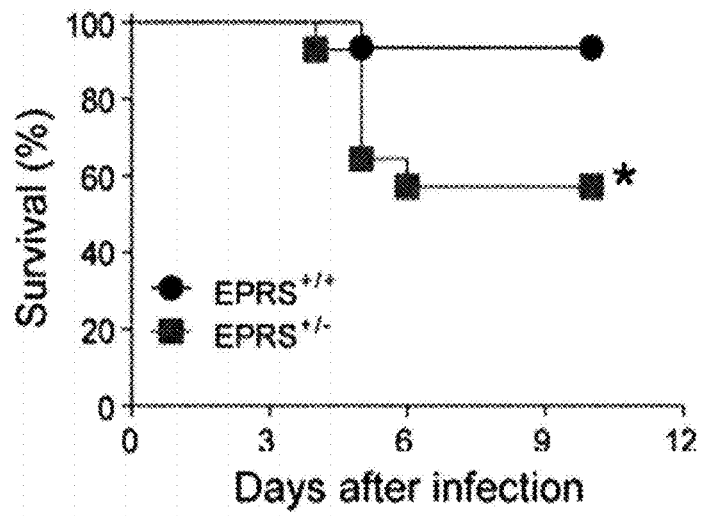
[FIG. 40]
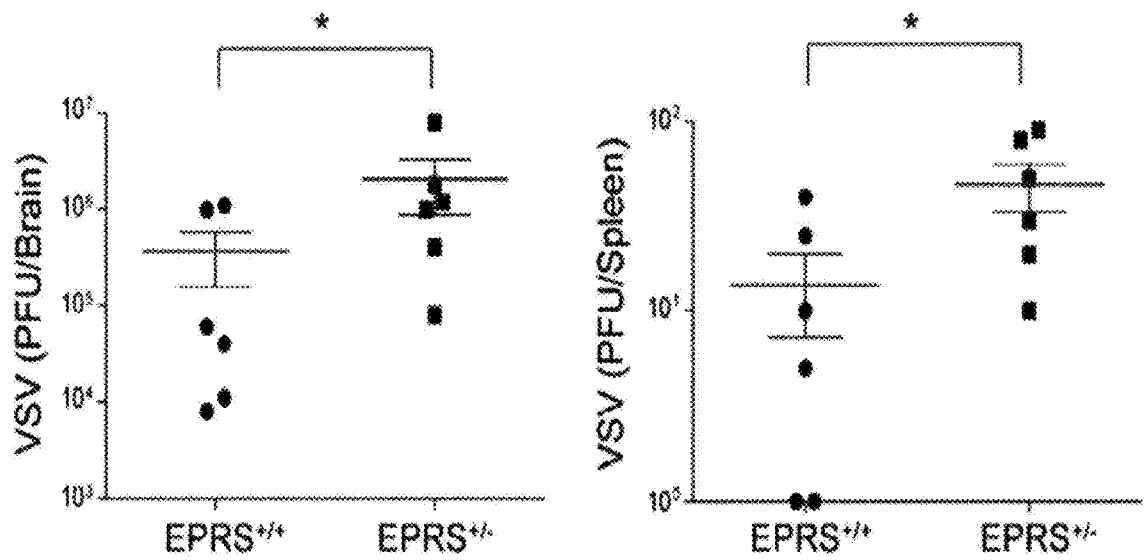

[FIG. 41]
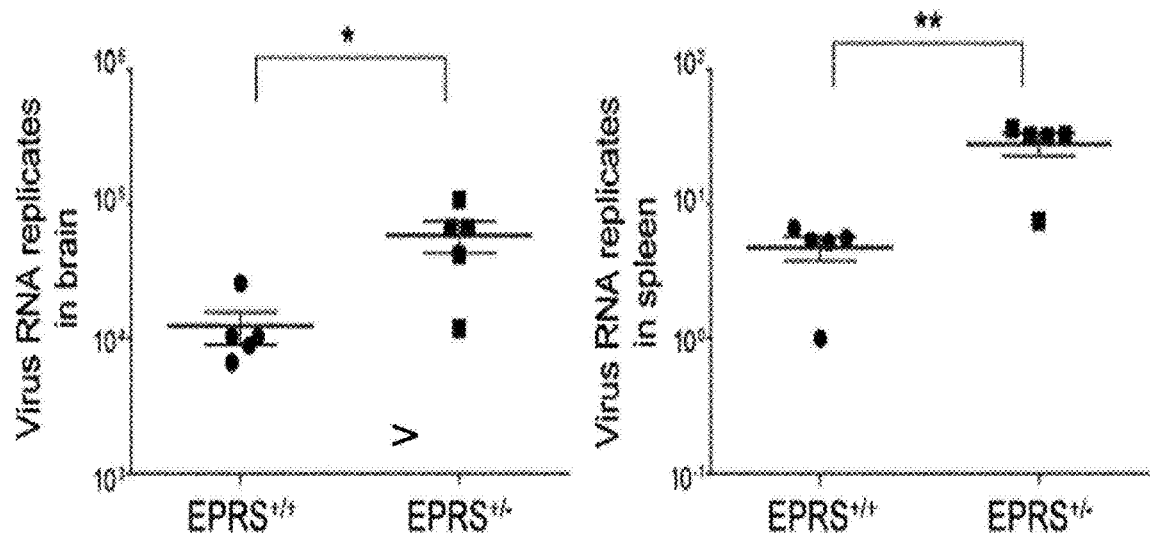
[FIG. 42]
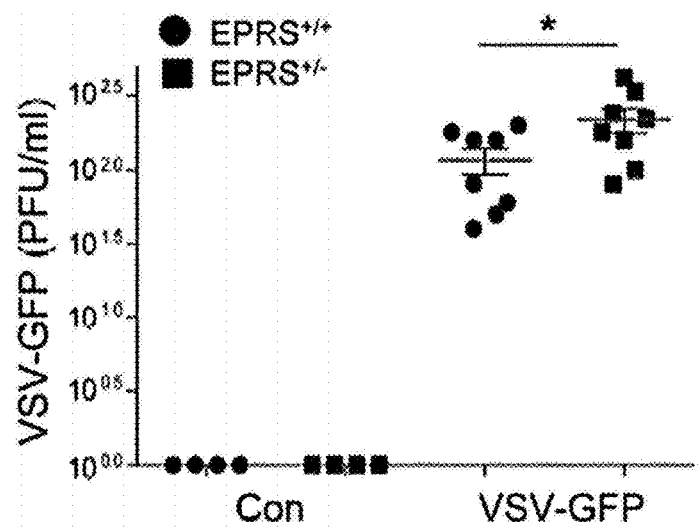

[FIG. 43]
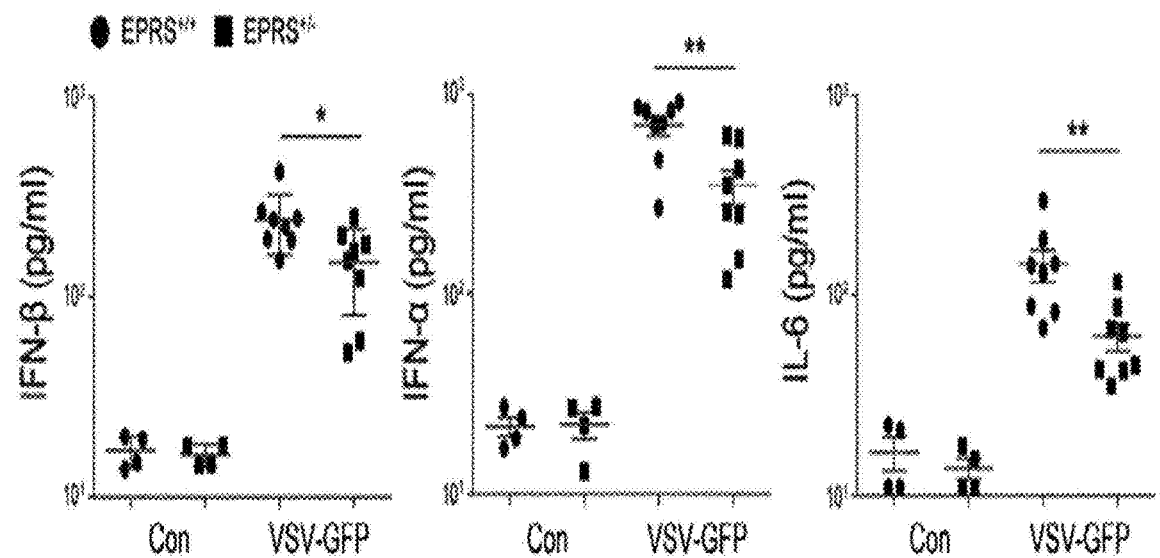
[FIG. 44]
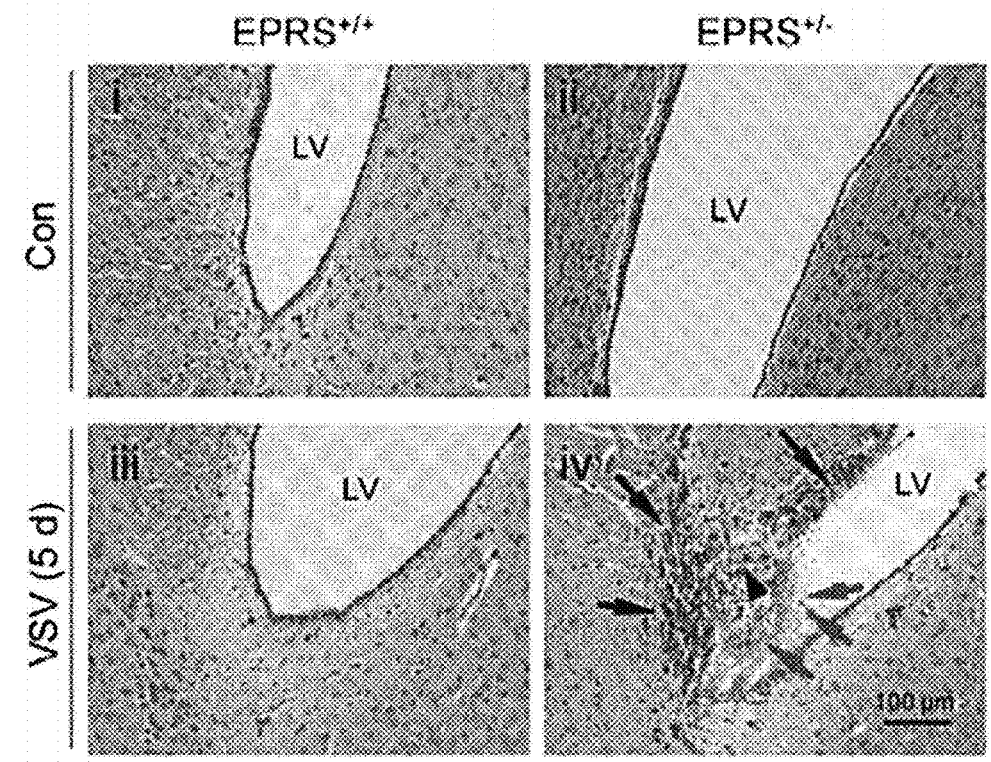

[FIG. 45]
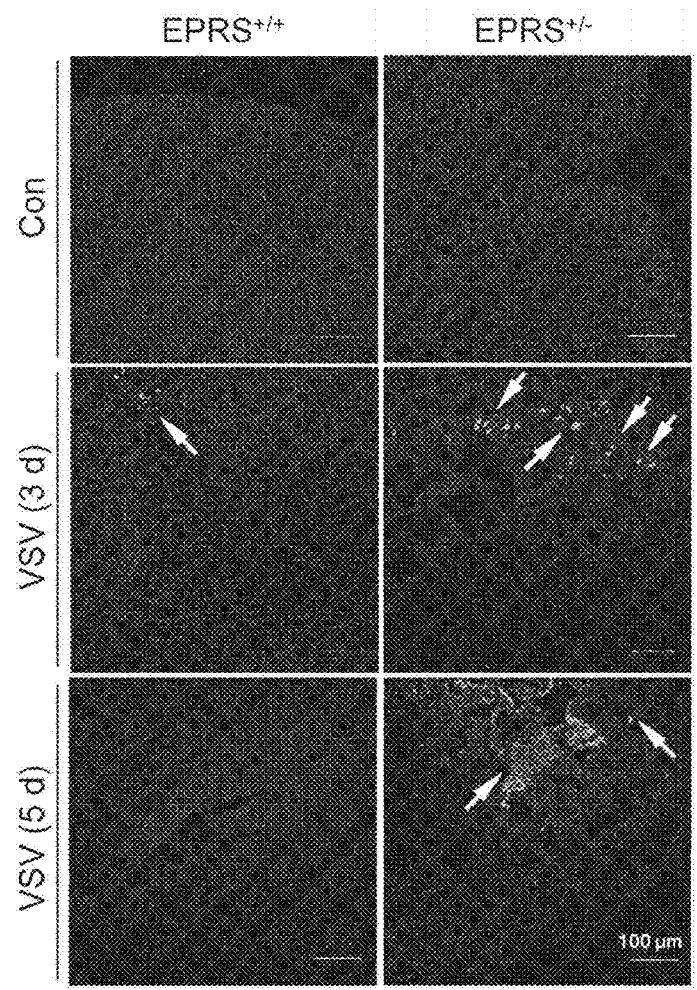

[FIG. 46]
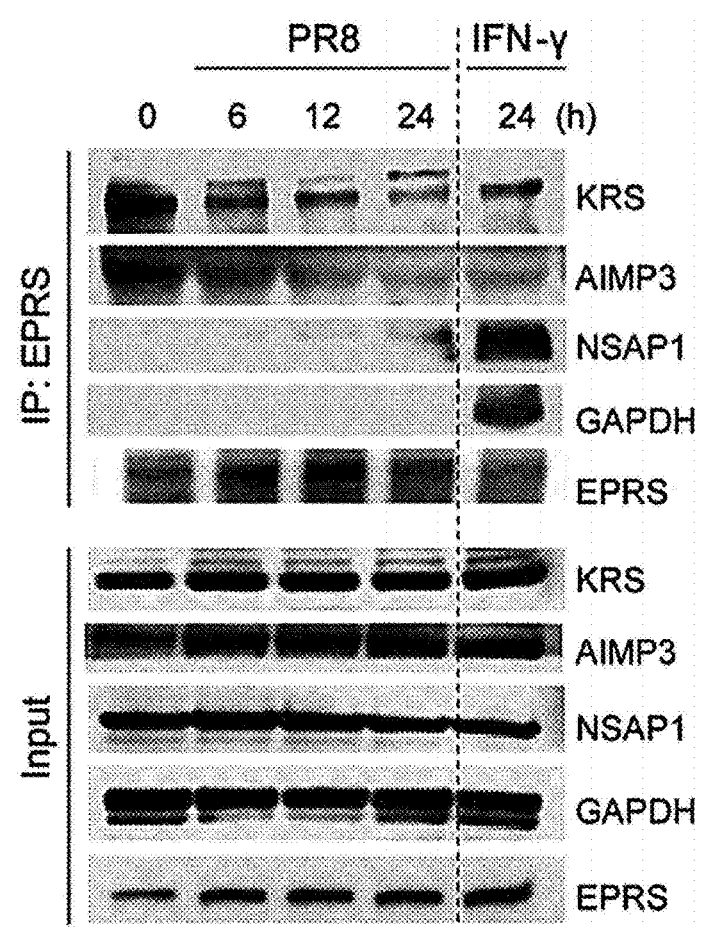

[FIG. 47]
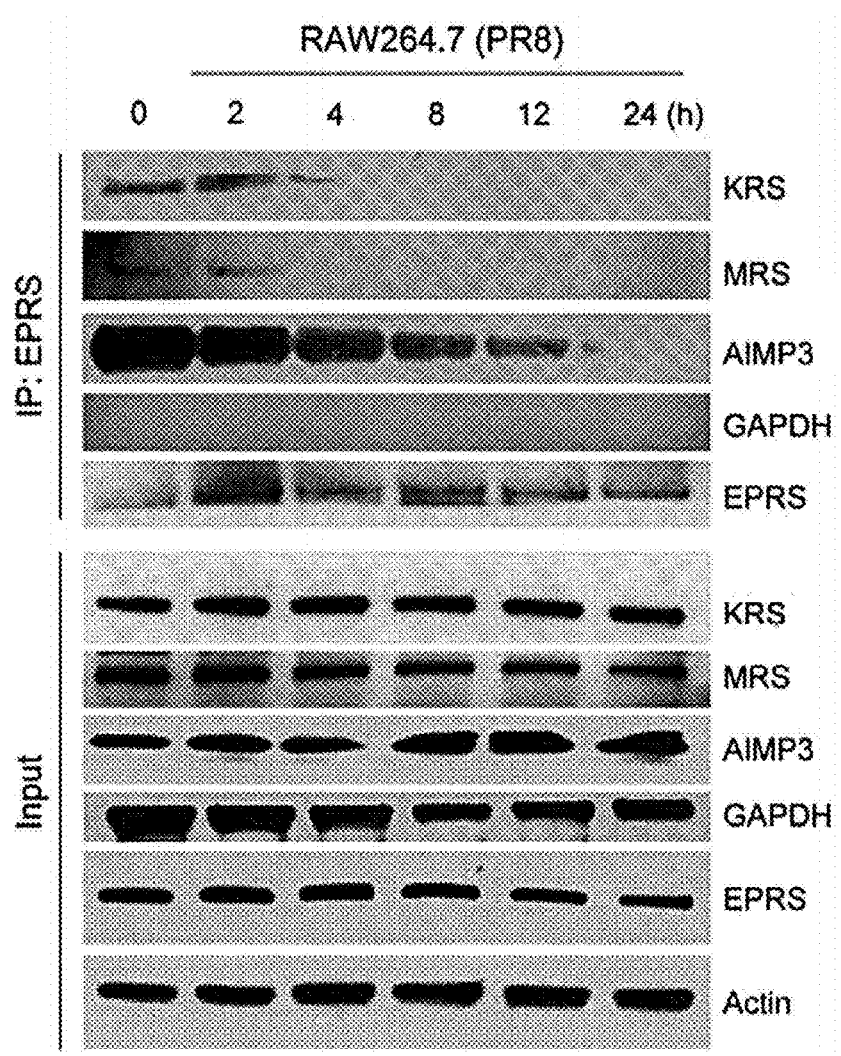

[FIG. 48]
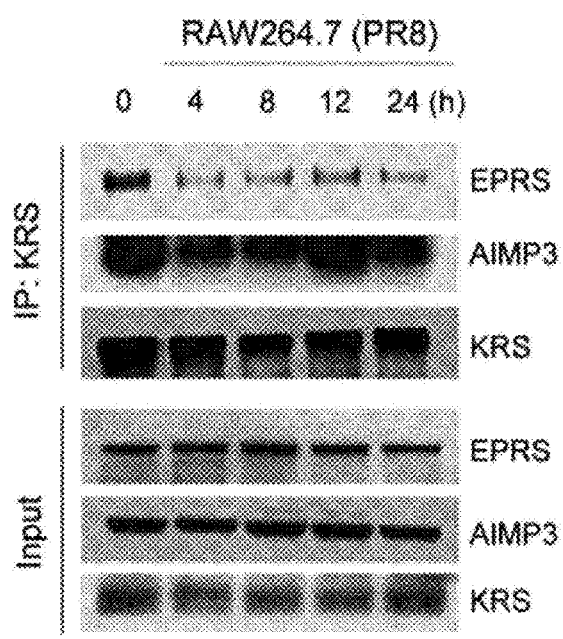

[FIG. 49]
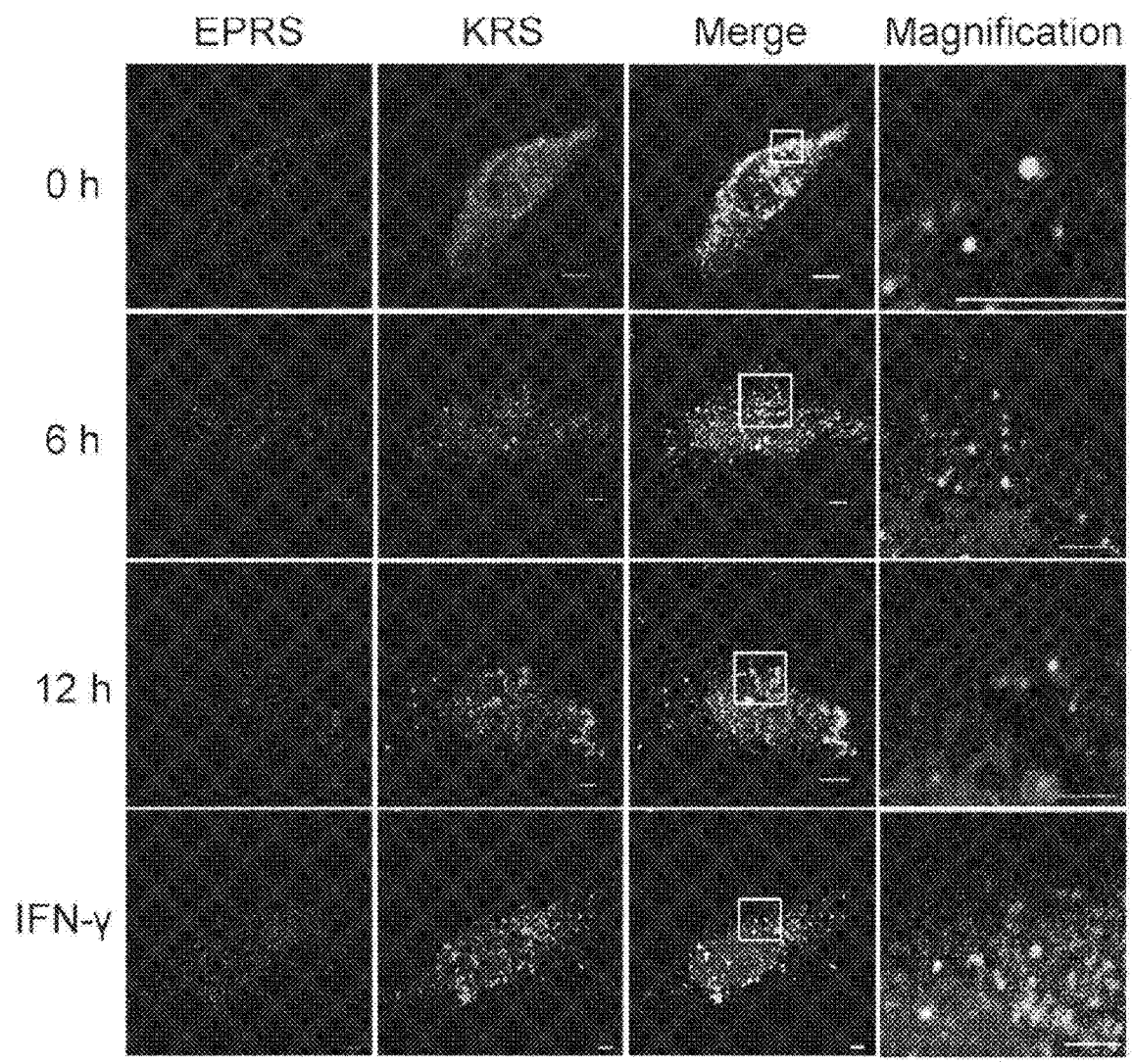

[FIG. 50]
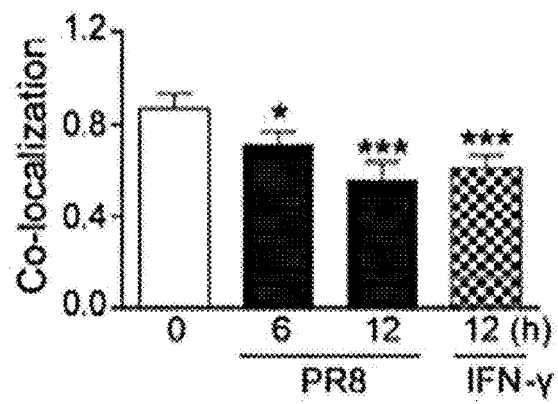
[FIG. 51]
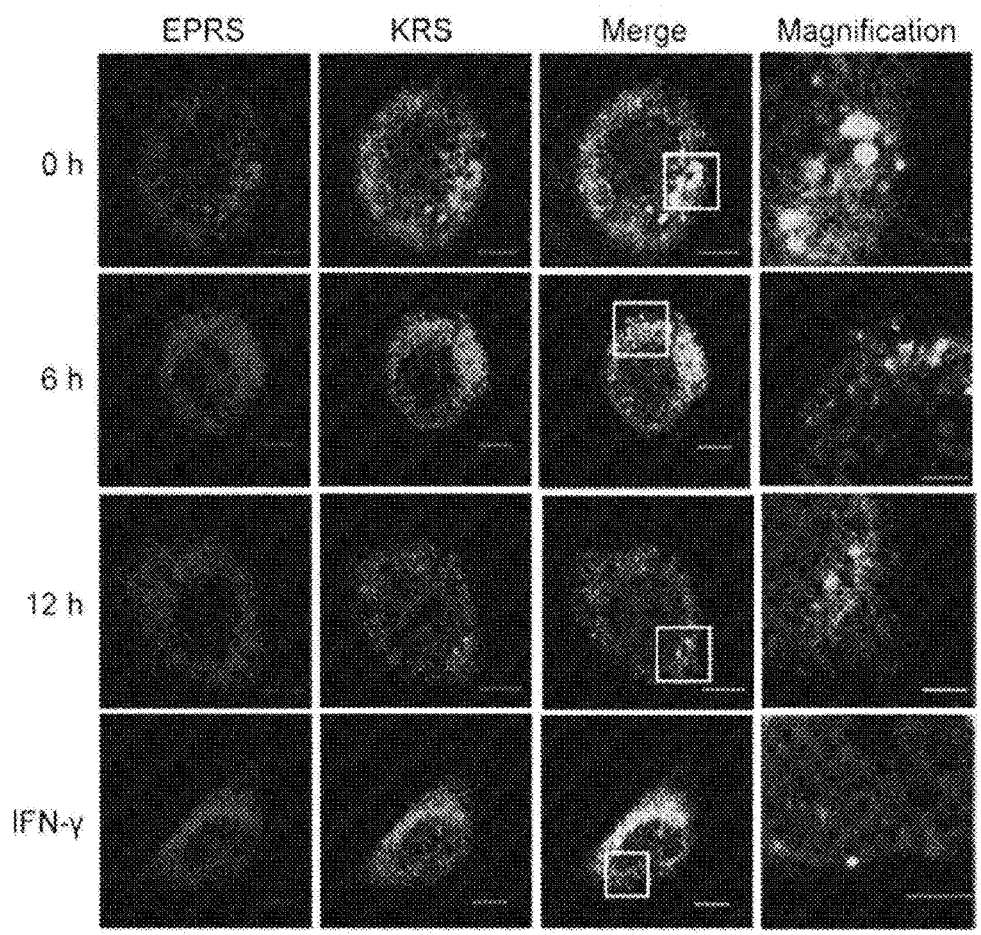

[FIG. 52]
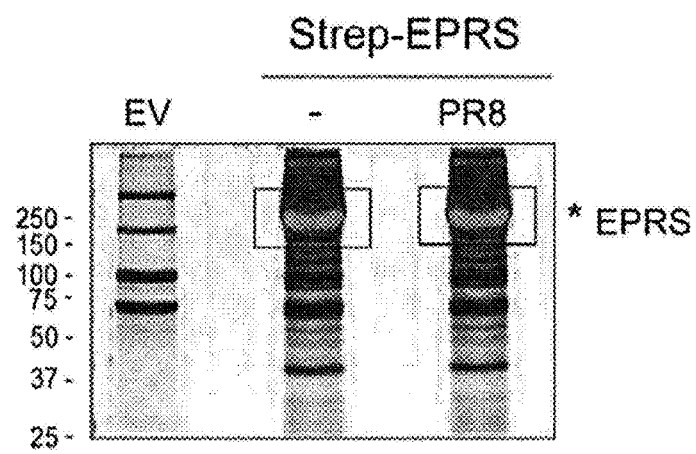

[FIG. 53]
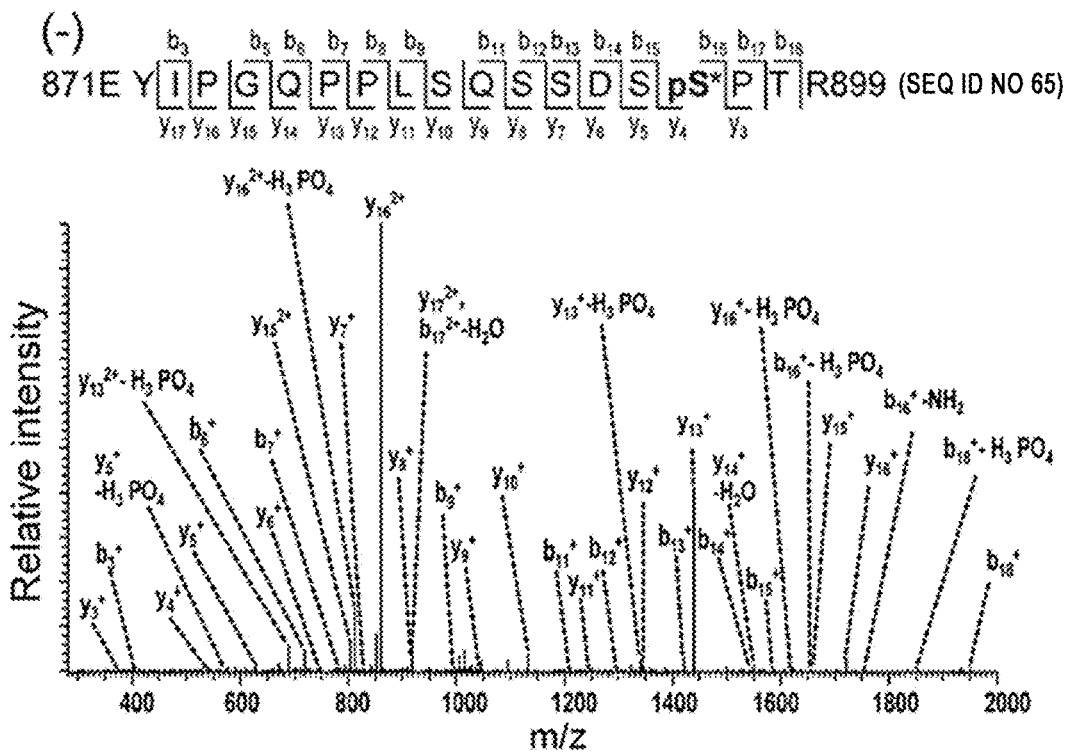
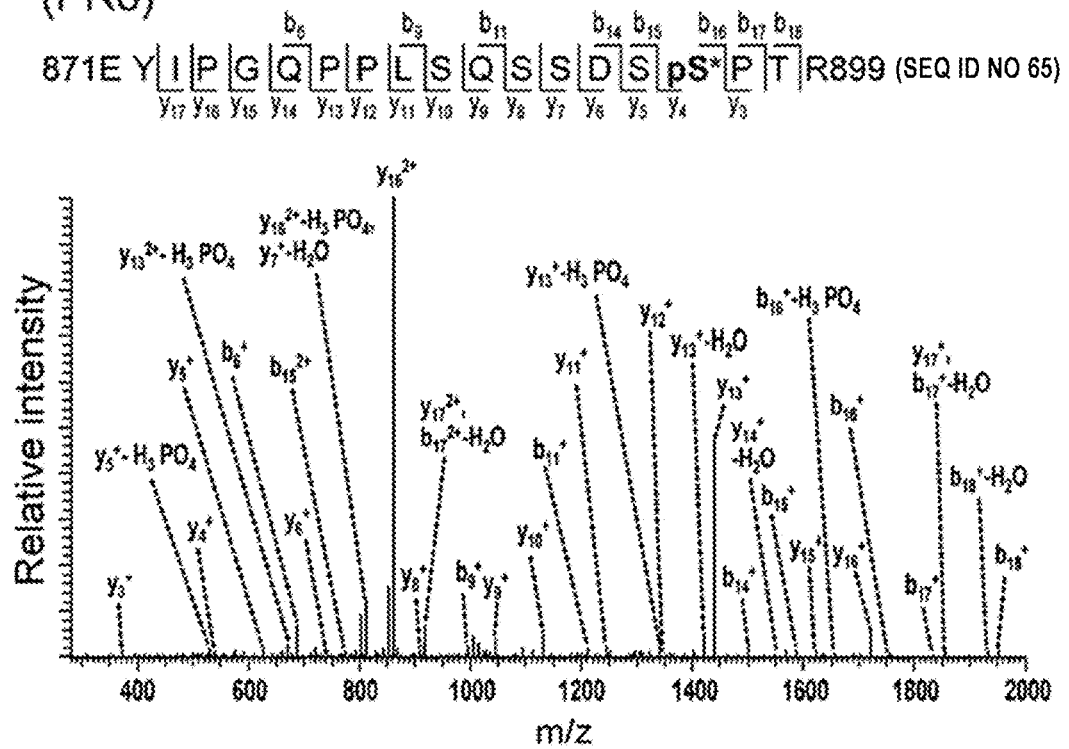

[FIG. 54]
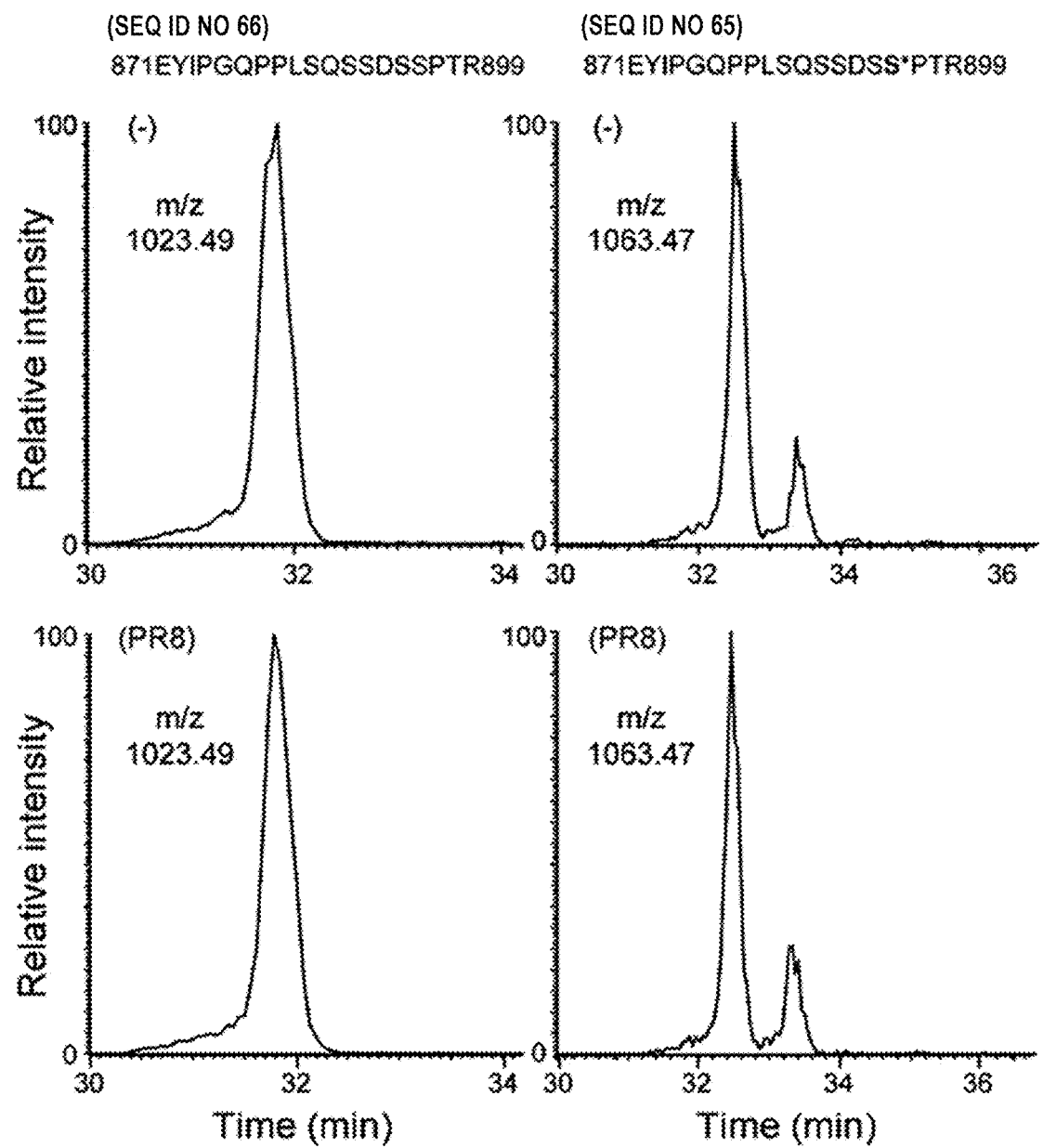

[FIG. 55]
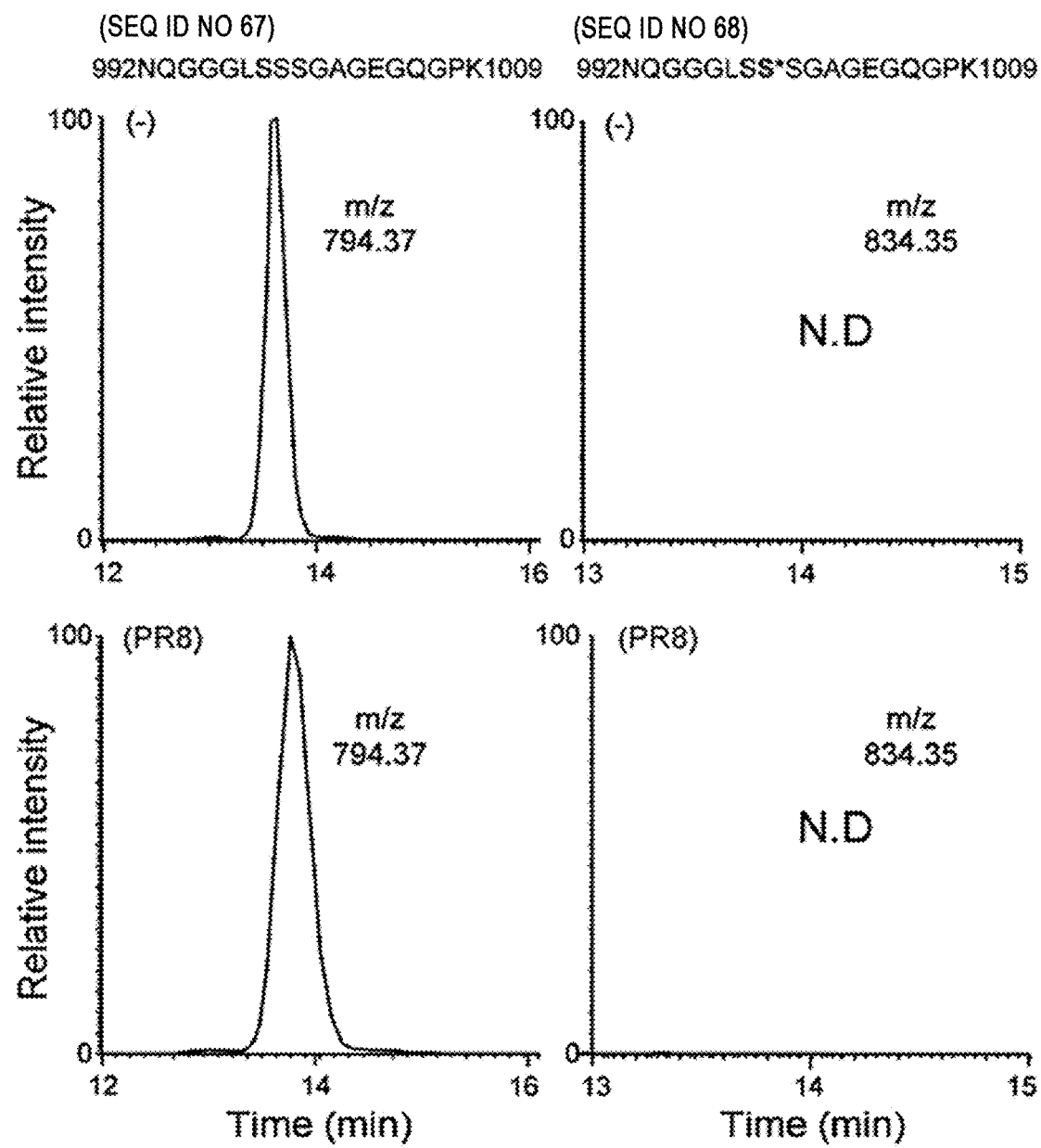

[FIG. 56]
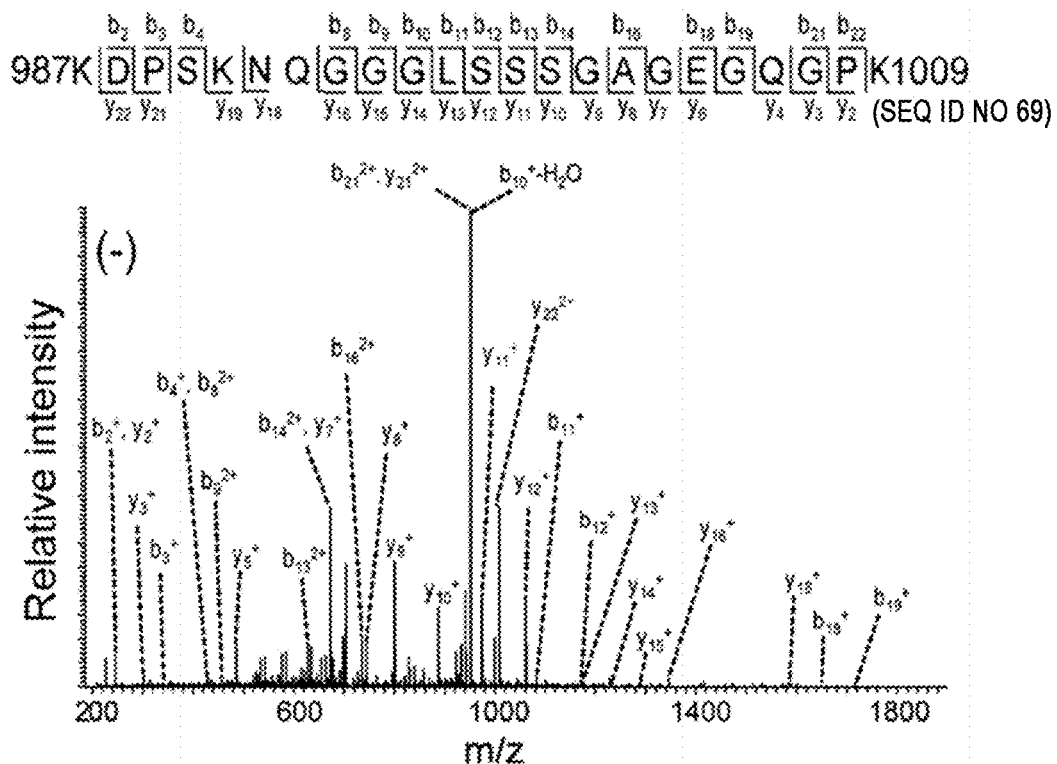
(SEQ ID NO 69)
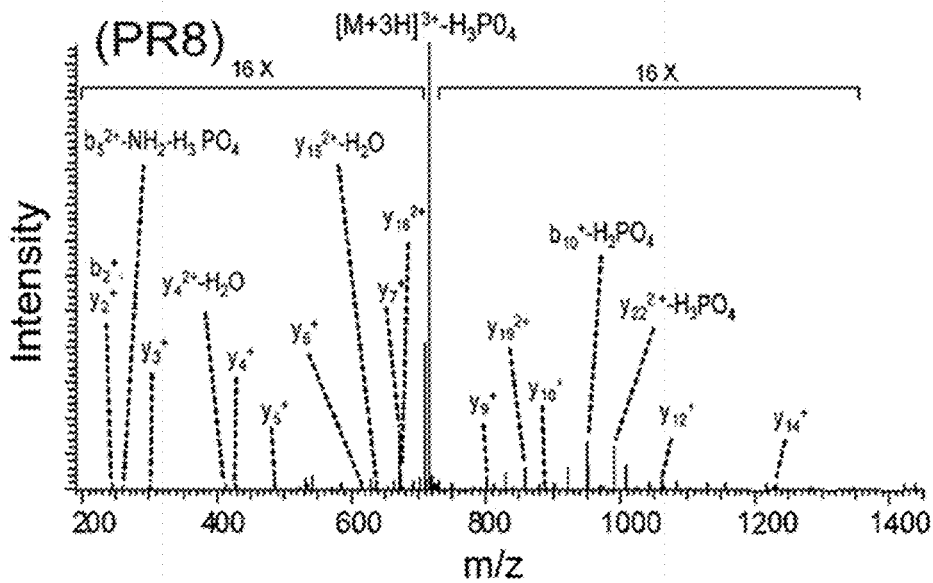
(SEQ ID NO 70)

[FIG. 57]
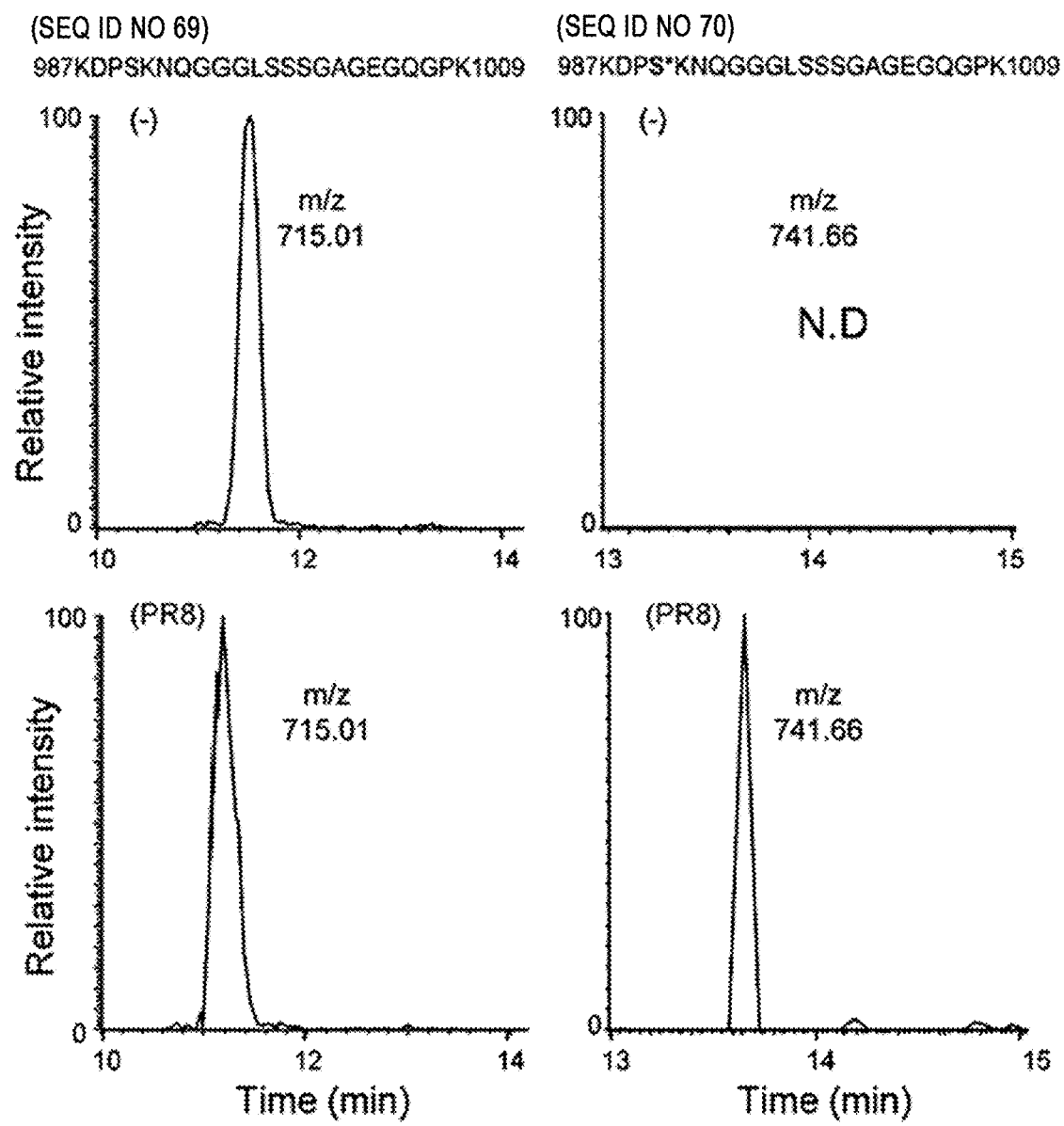

[FIG. 58]
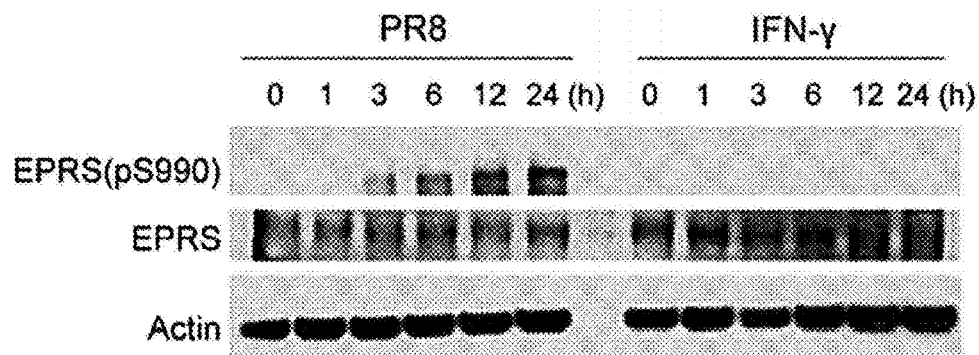
[FIG. 59]
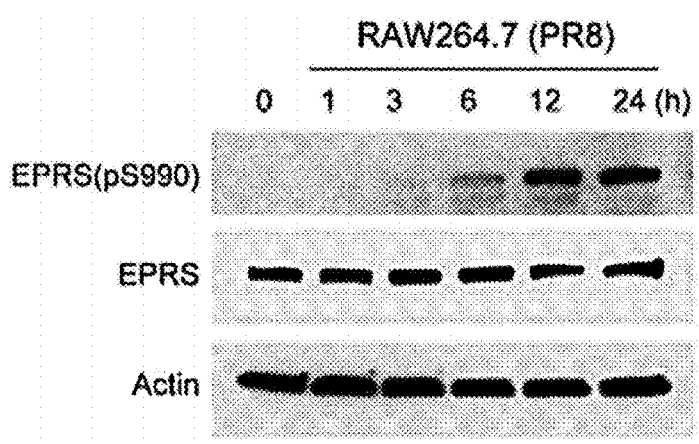
[FIG. 60]
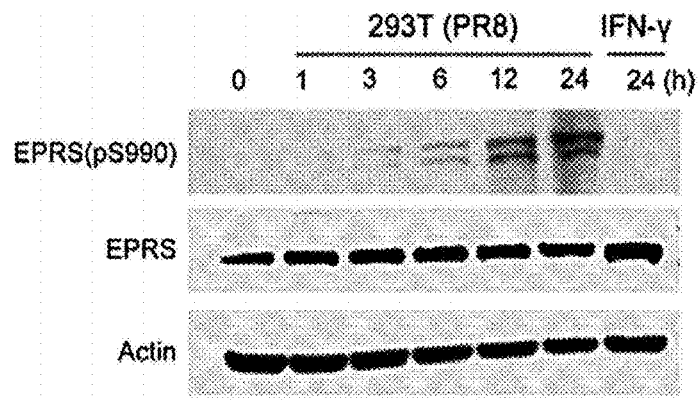

[FIG. 61]
[FIG. 62]
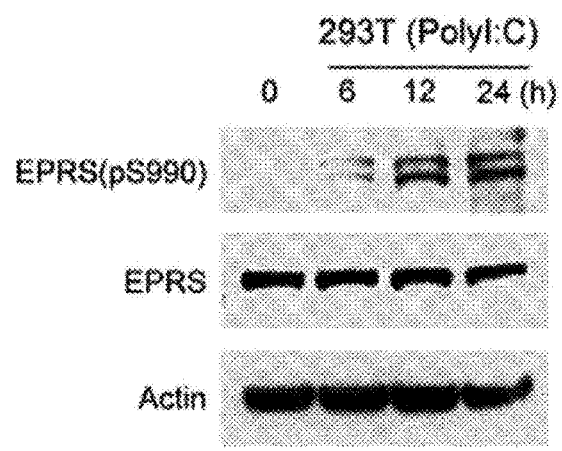
[FIG. 63]
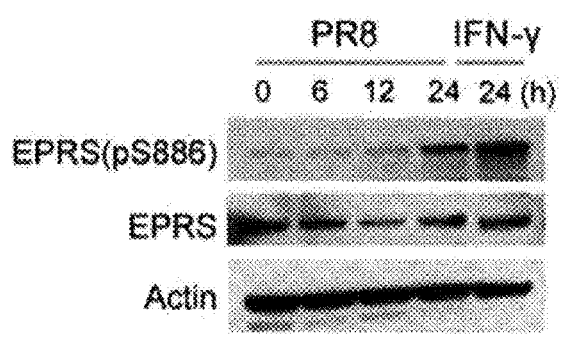

[FIG. 64]
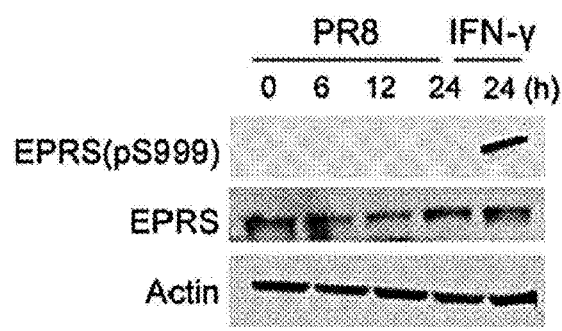
[FIG. 65]
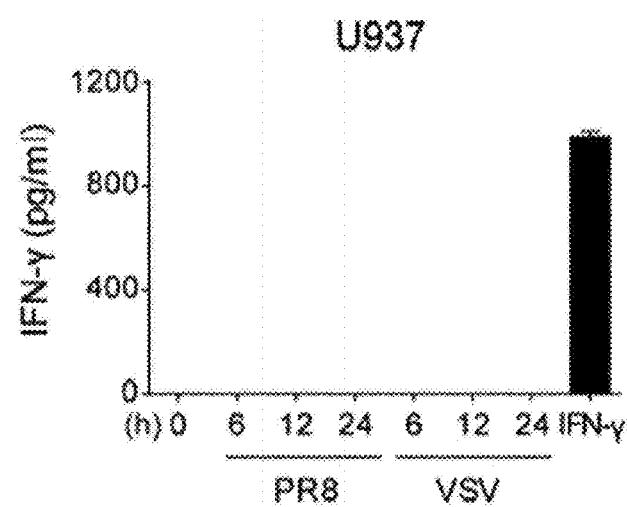

[FIG. 66]
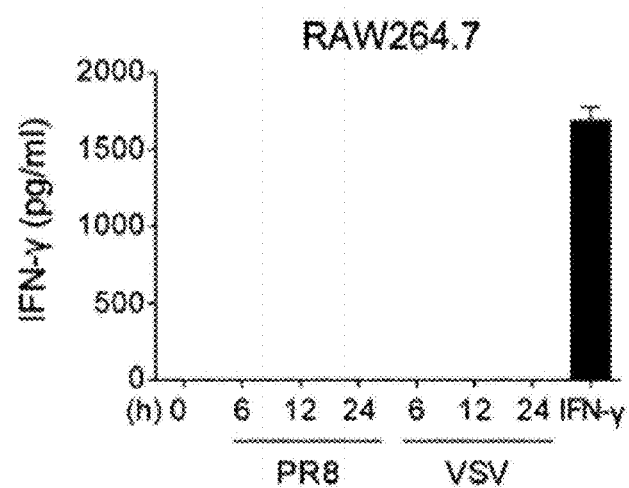
[FIG. 67]
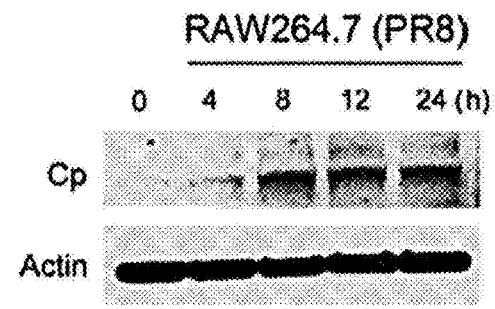

[FIG. 68]
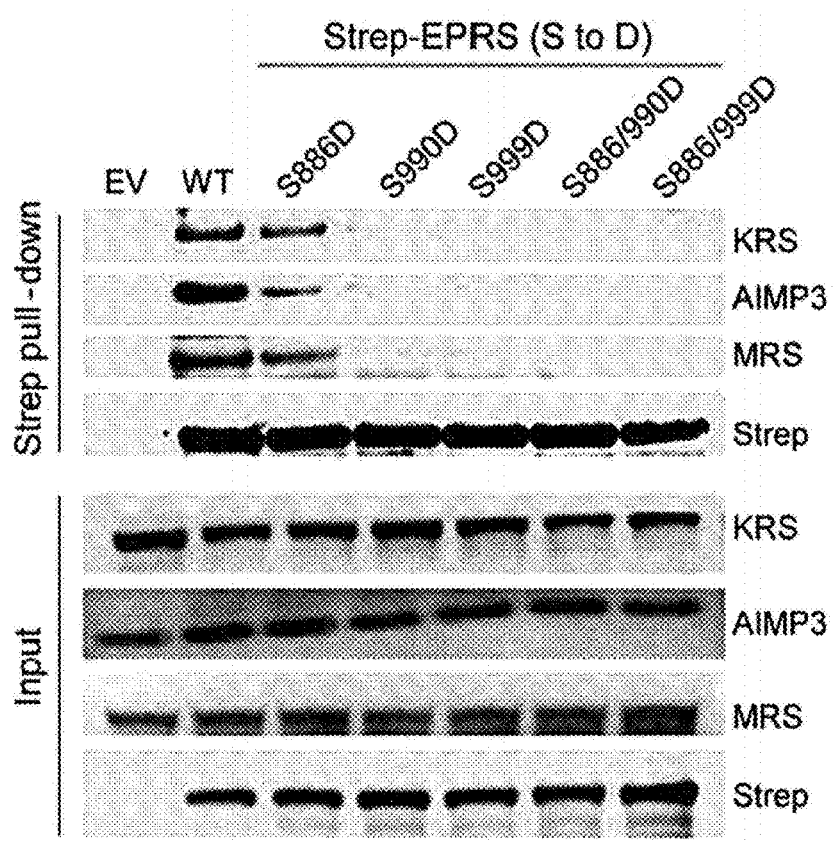
[FIG. 69]
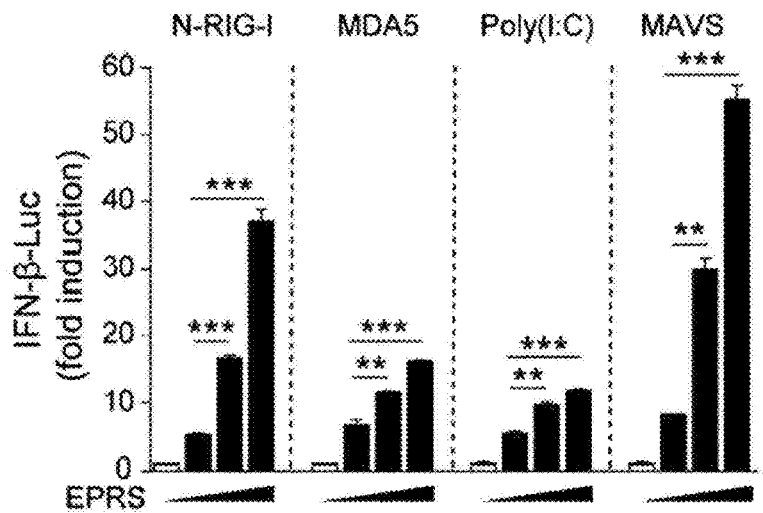

[FIG. 70]
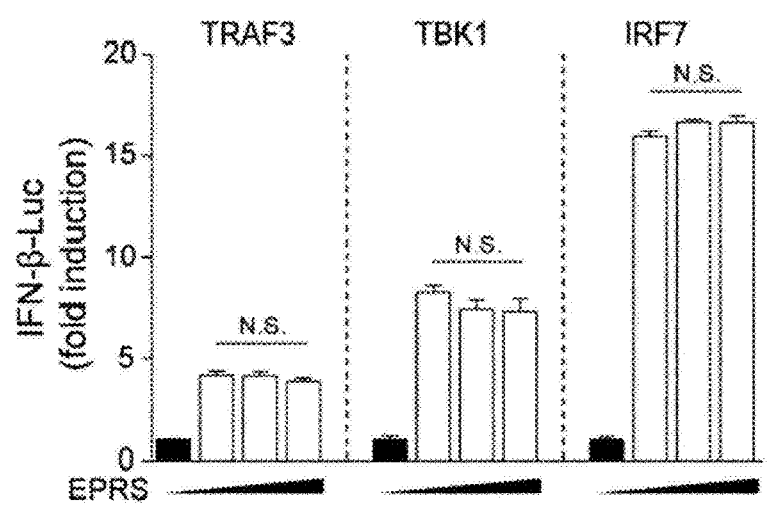
[FIG. 71]
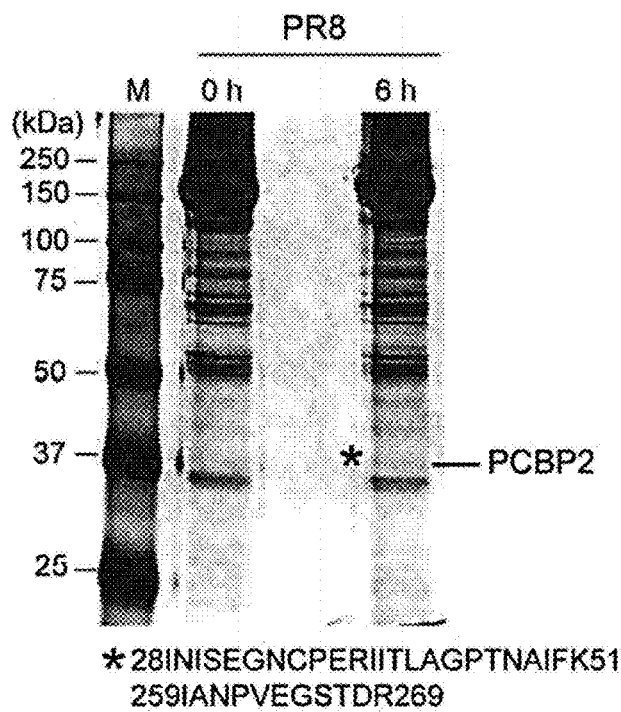
*28INISEGNCPERIITLAGPTNAIFK51
259IANPVEGSTDR269

[FIG. 72]
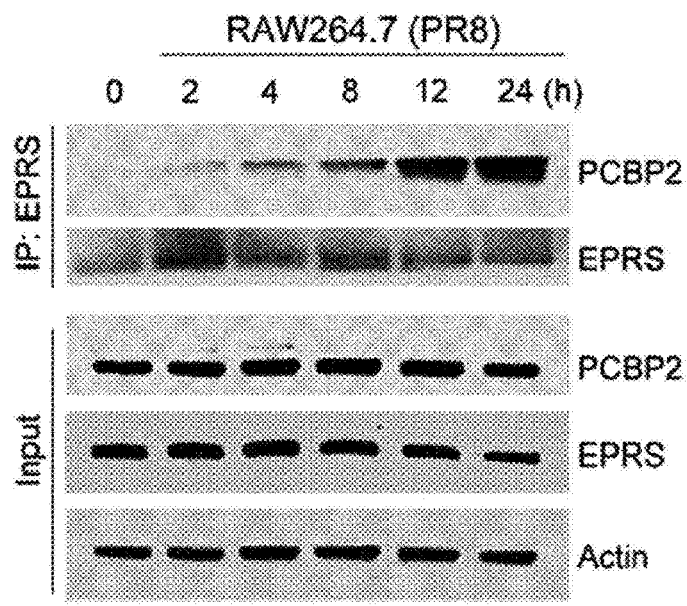
[FIG. 73]
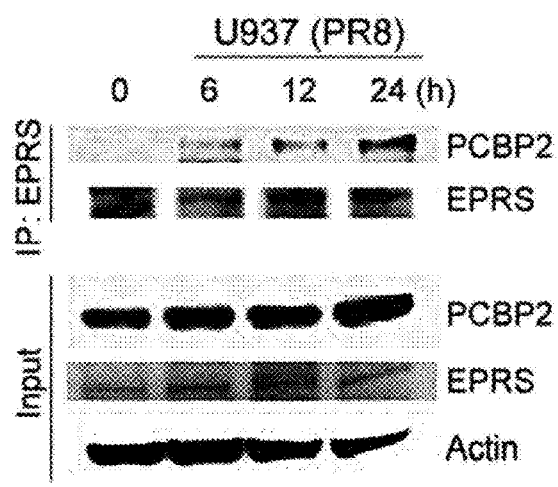

[FIG. 74]
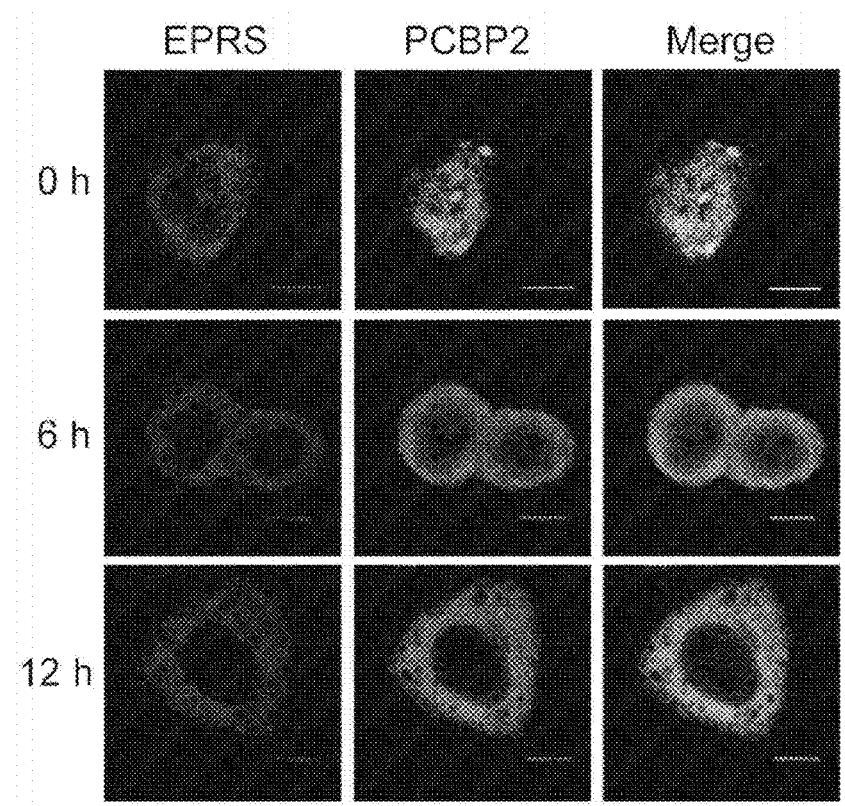

[FIG. 75]
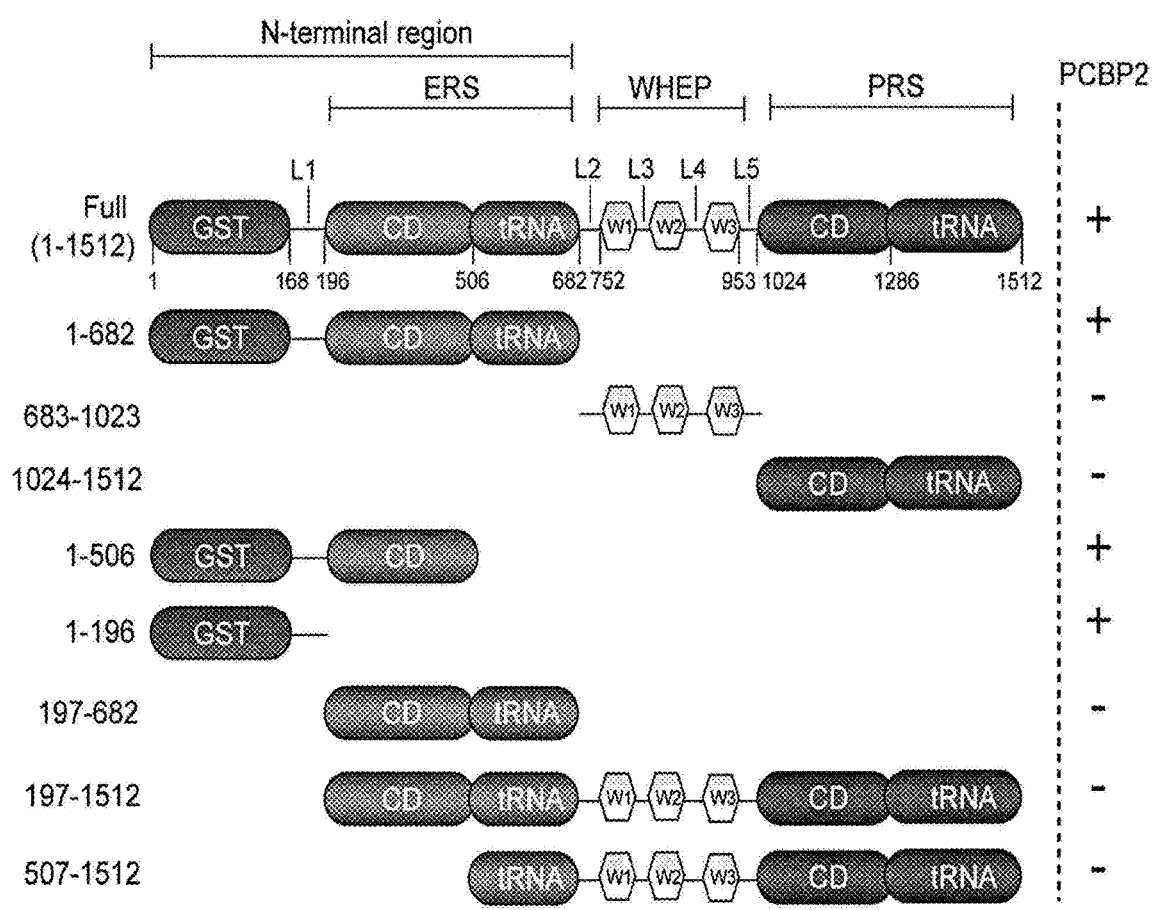

[FIG. 76]
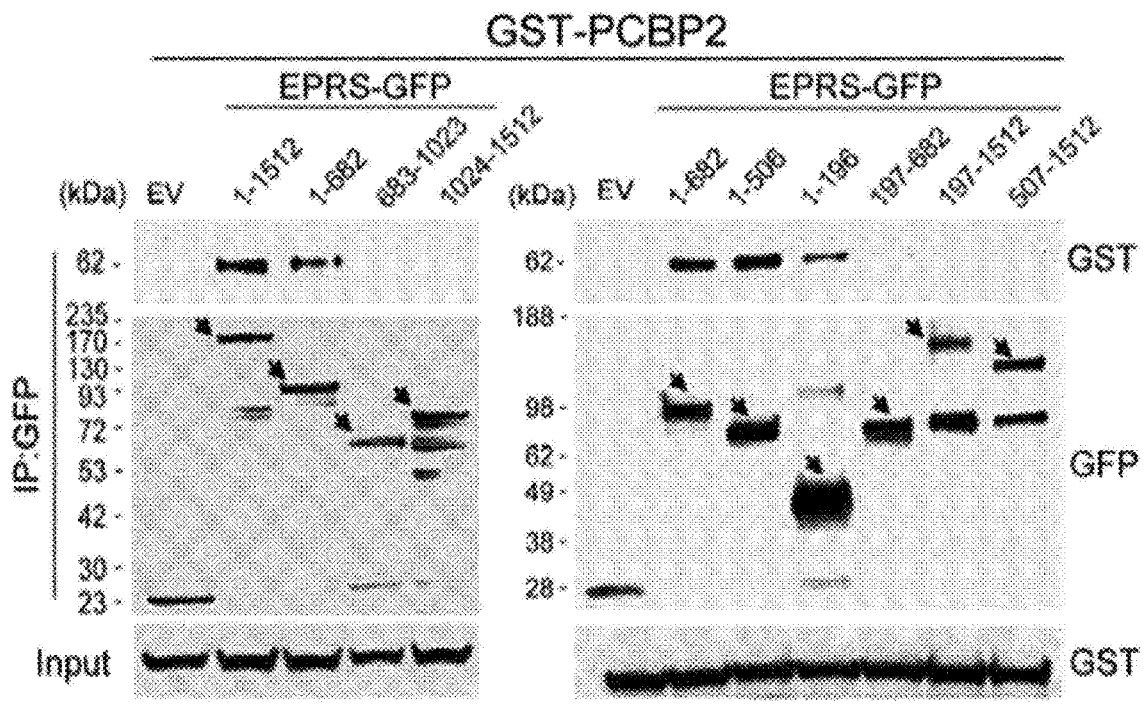
[FIG. 77]
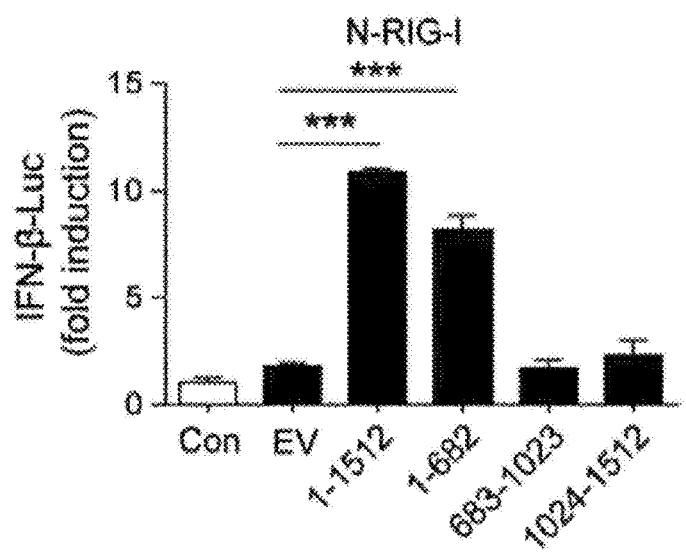

[FIG. 78]
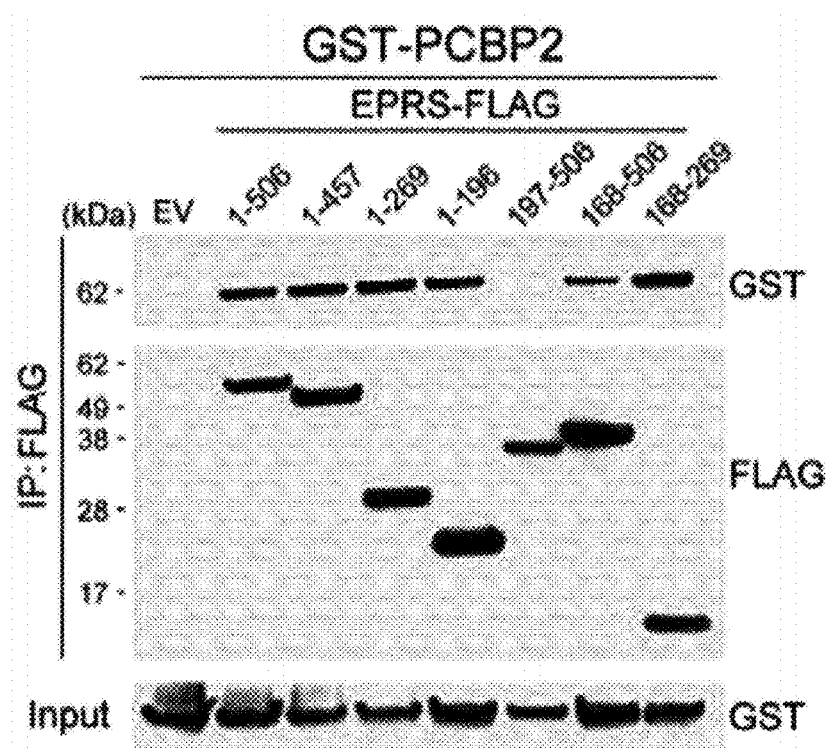
[FIG. 79]
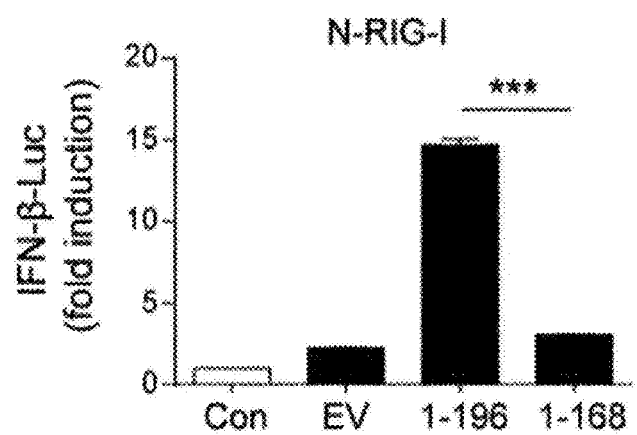

[FIG. 80]
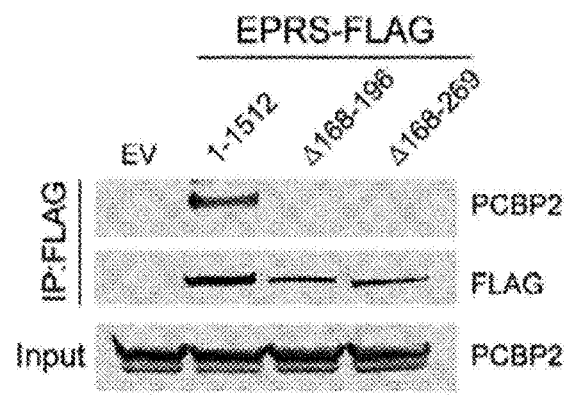
[FIG. 81]
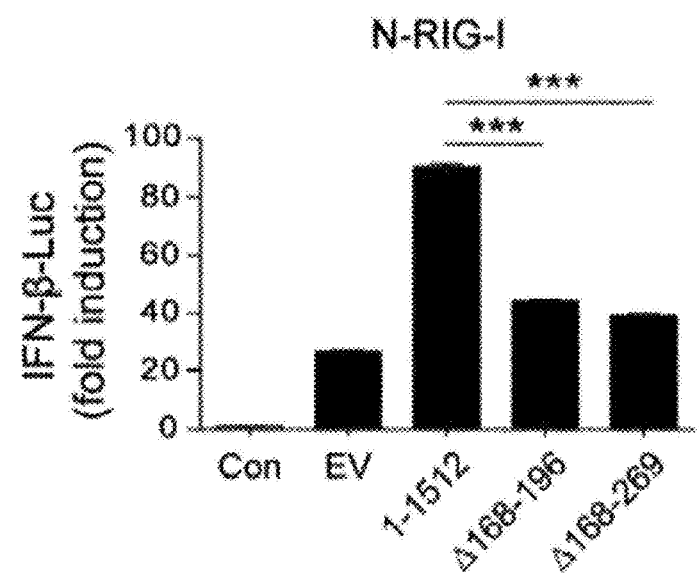

[FIG. 82]
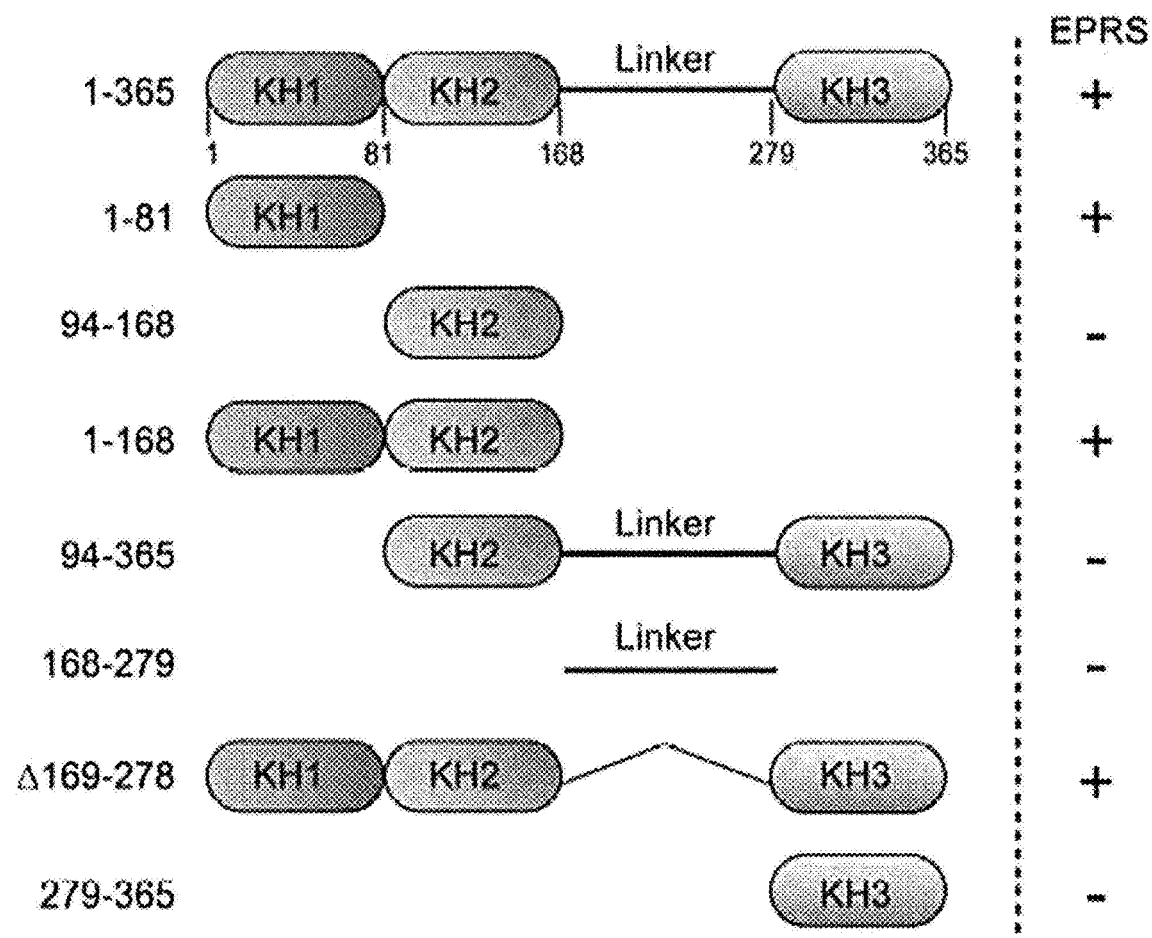

[FIG. 83]
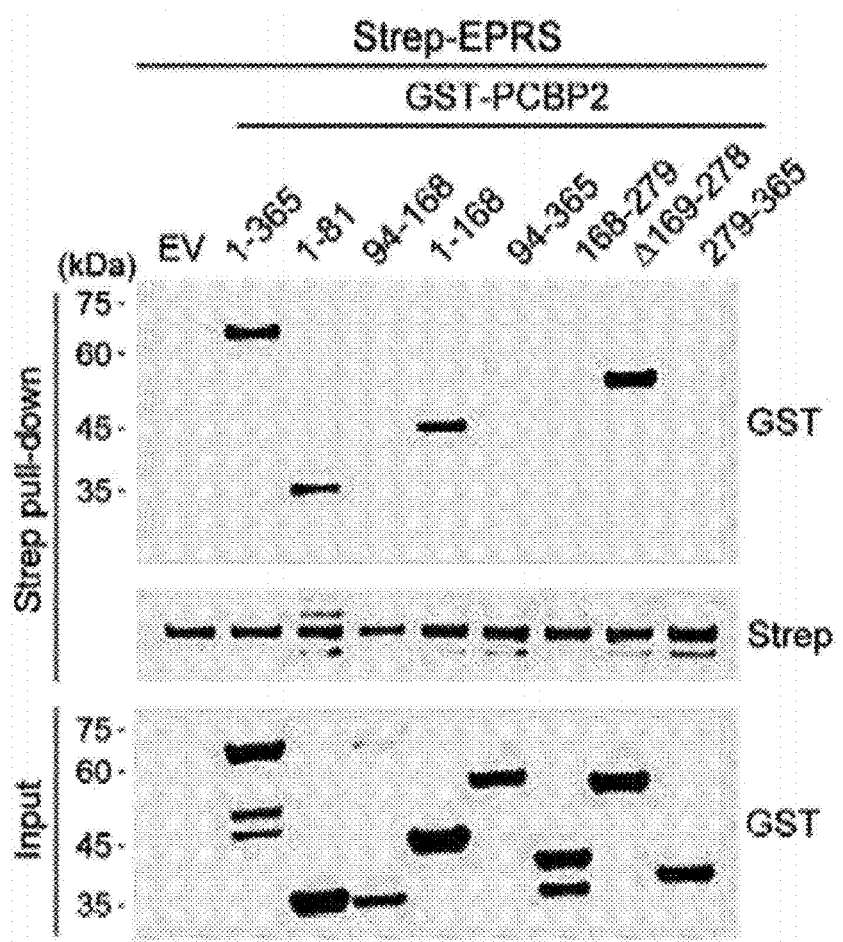

[FIG. 84]
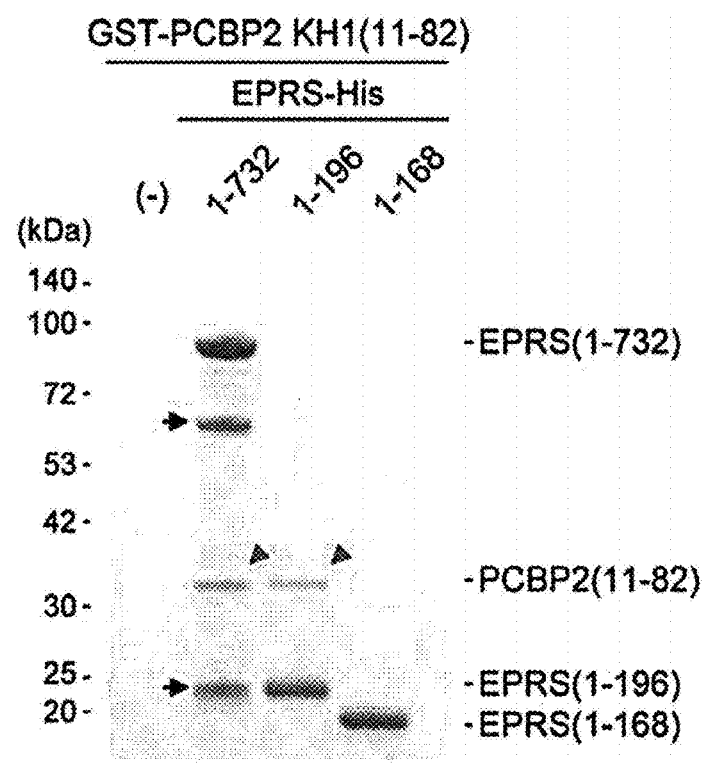

[FIG. 85]
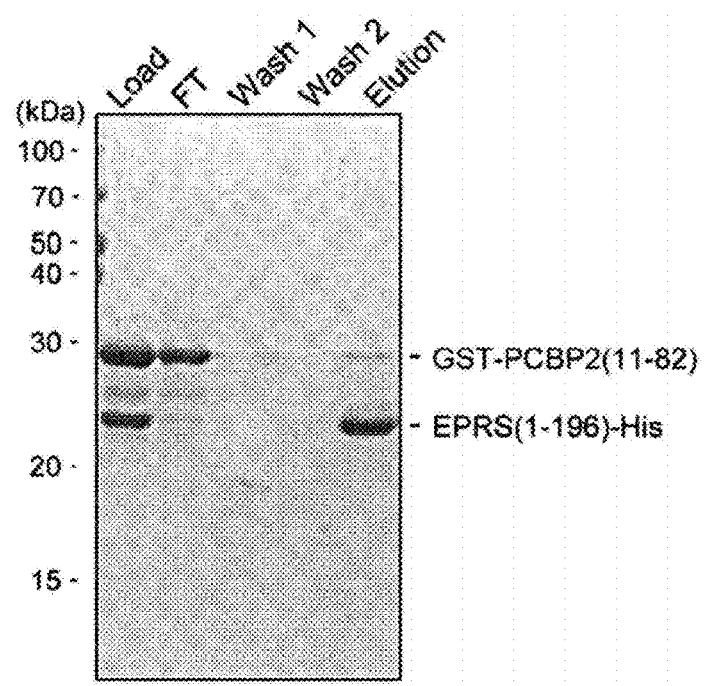

[FIG. 86]
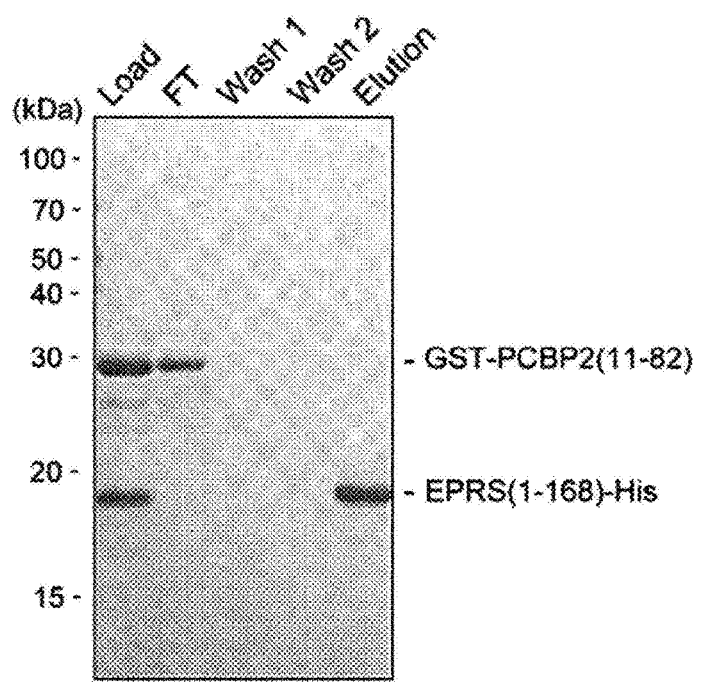

[FIG. 87]
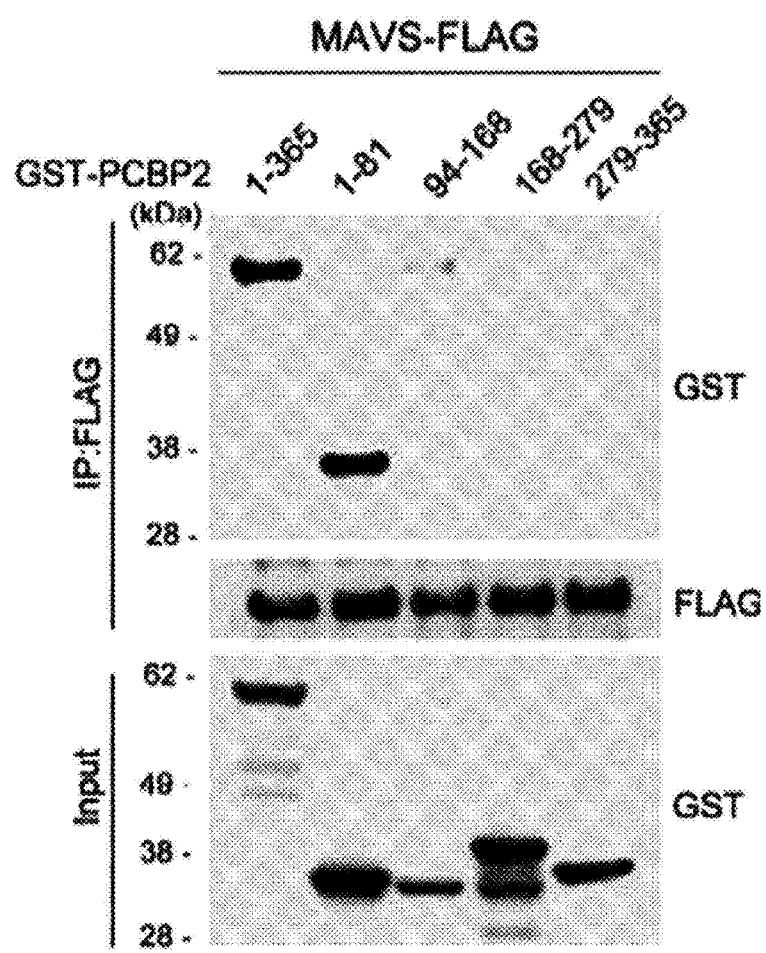

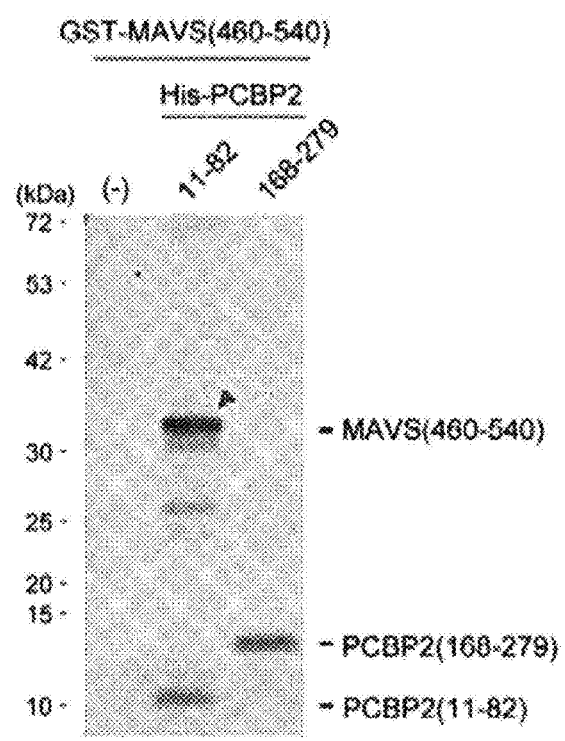
[FIG. 88]

[FIG. 89]
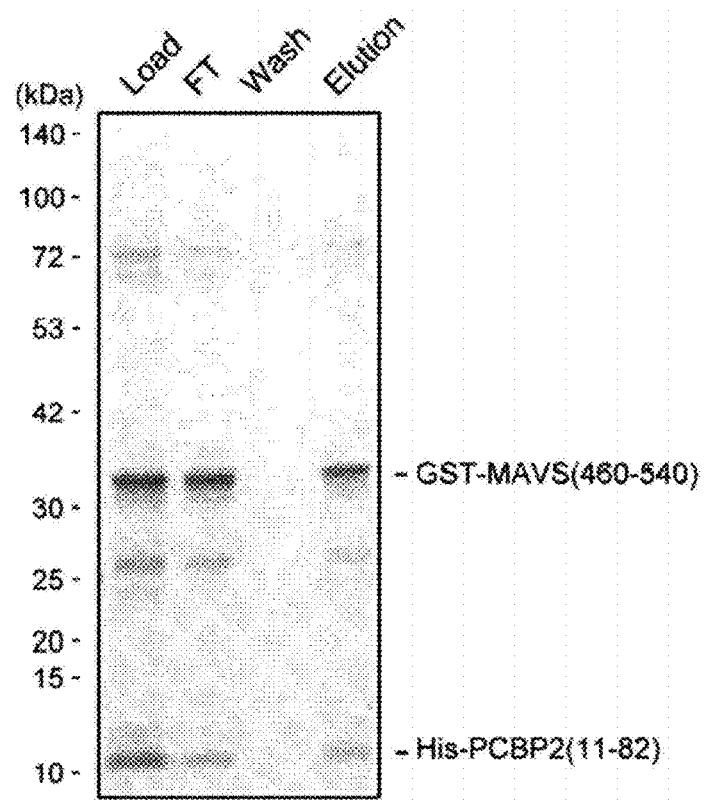

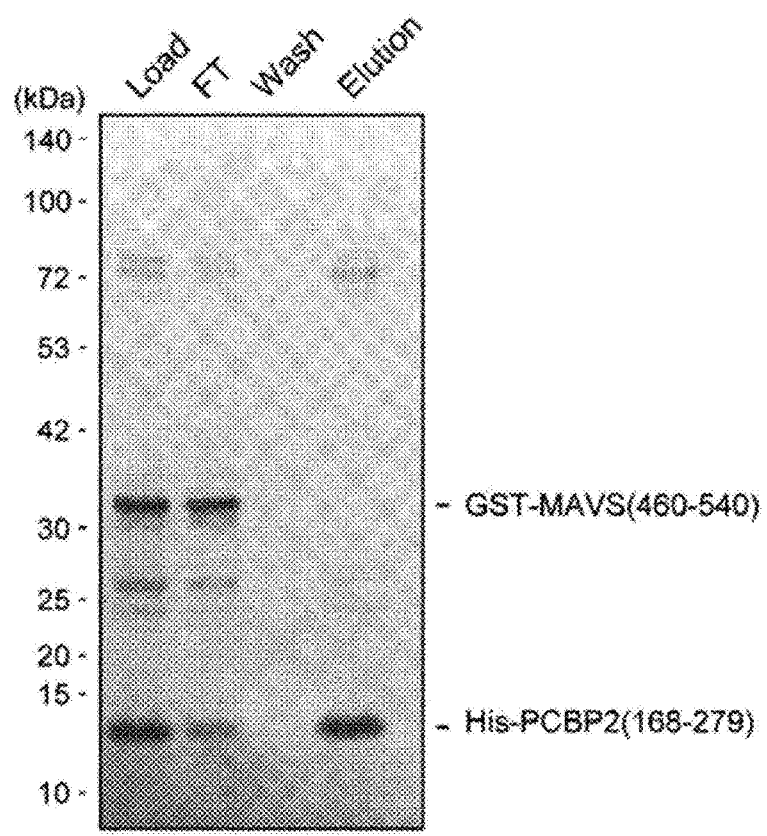
[FIG. 90]

[FIG. 91]
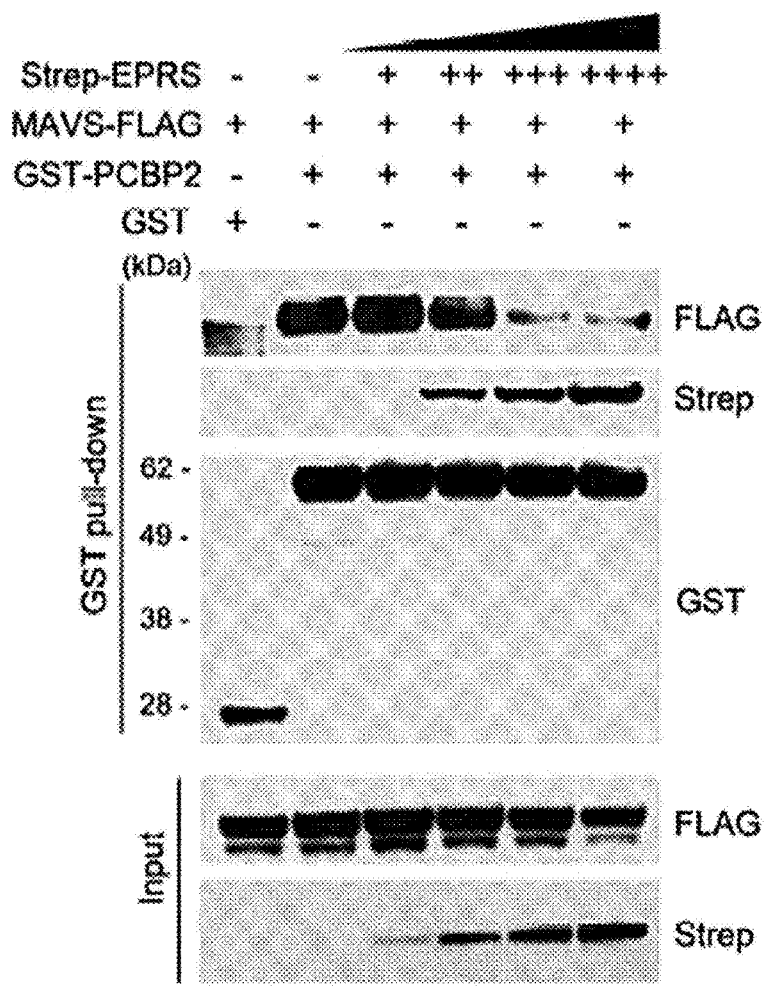

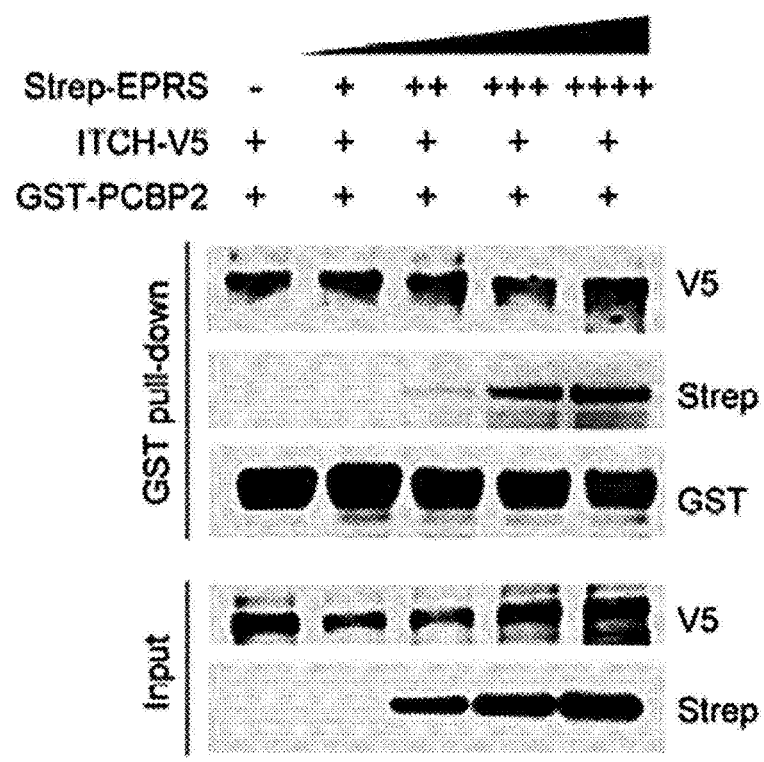
[FIG. 92]

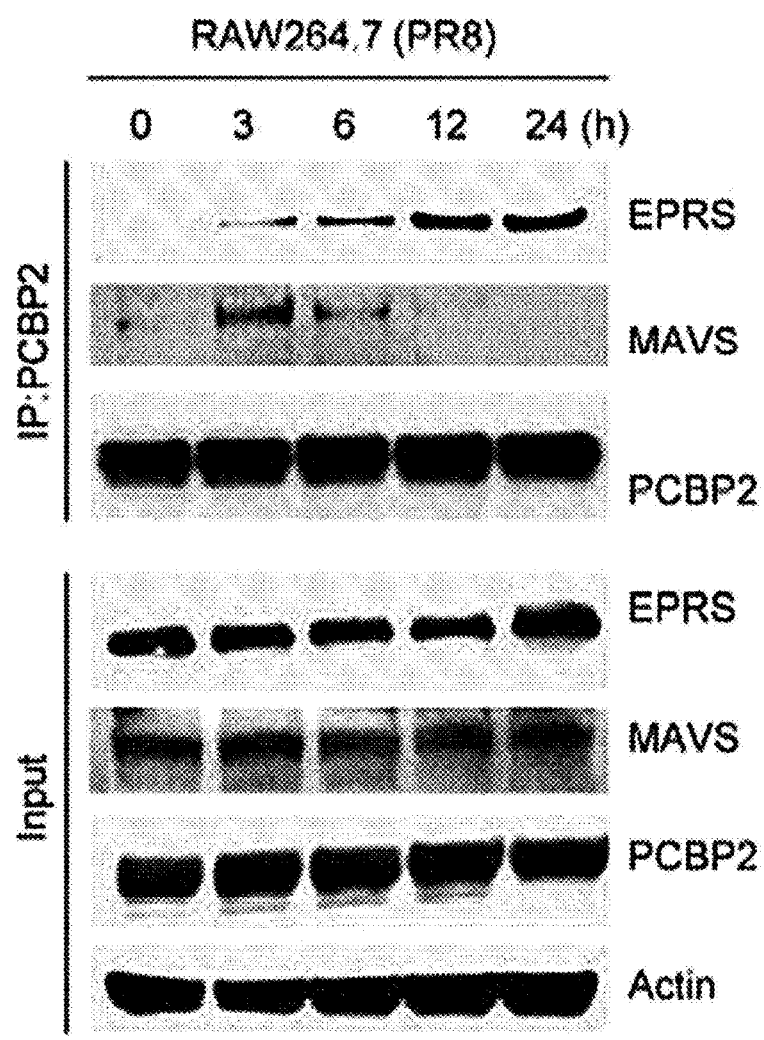
[FIG. 93]

[FIG. 94]
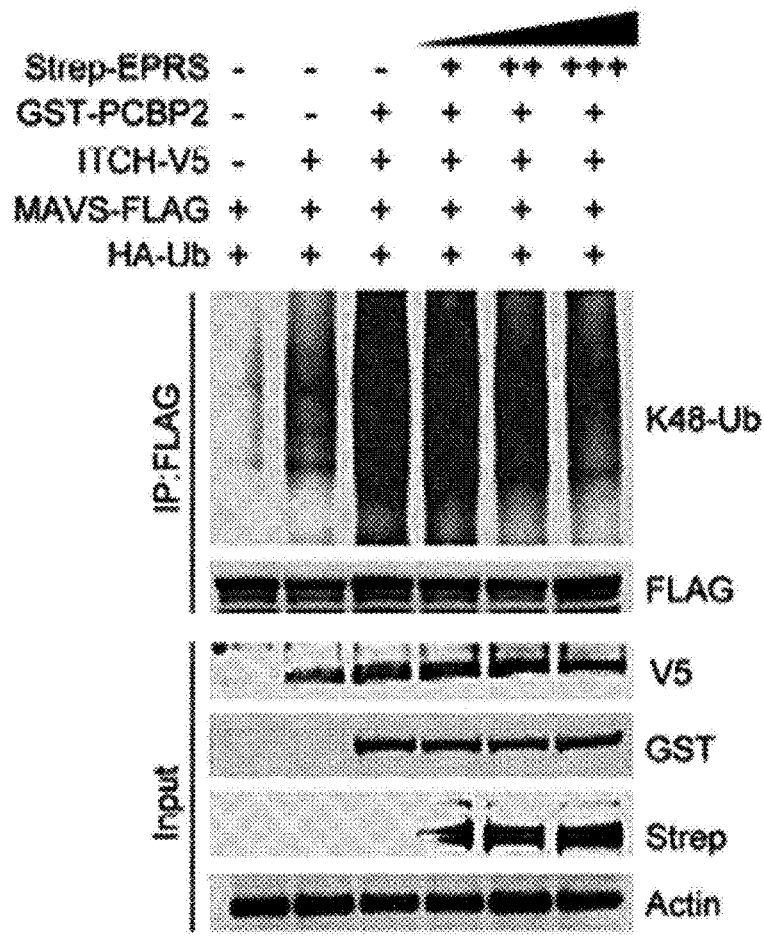

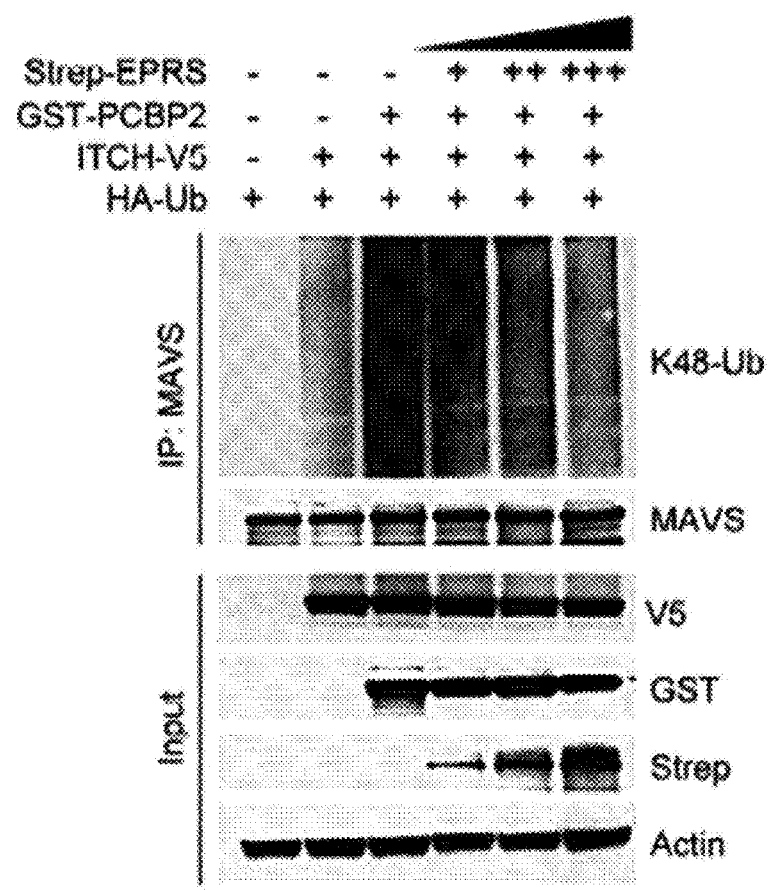
[FIG. 95]

[FIG. 96]
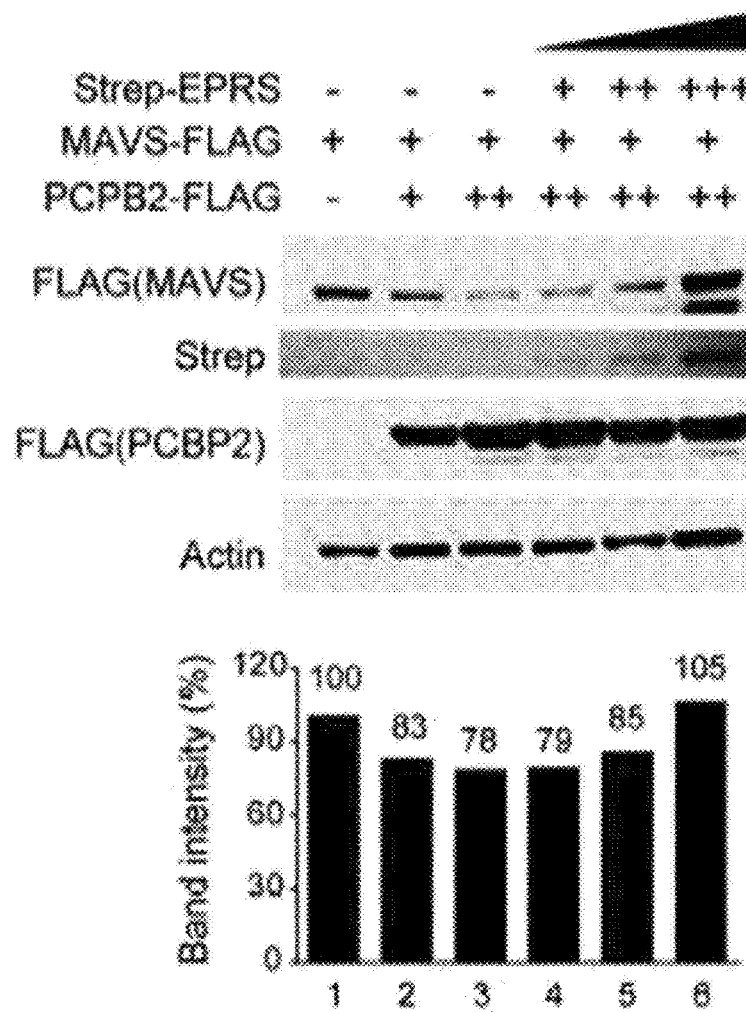

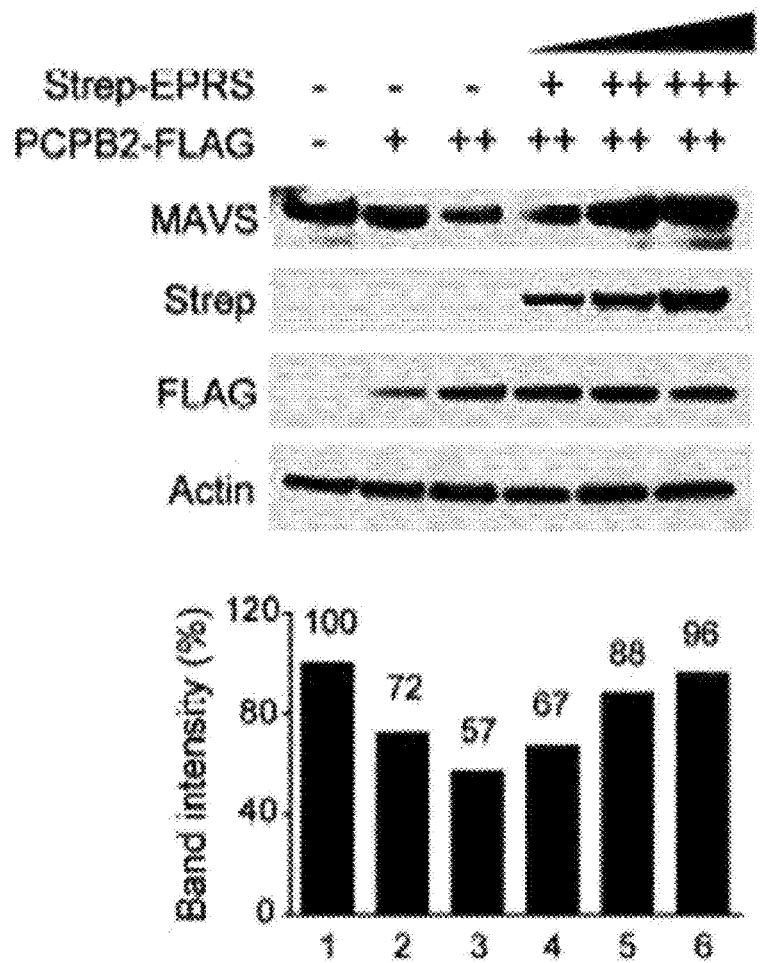
[FIG. 97]

[FIG. 98]
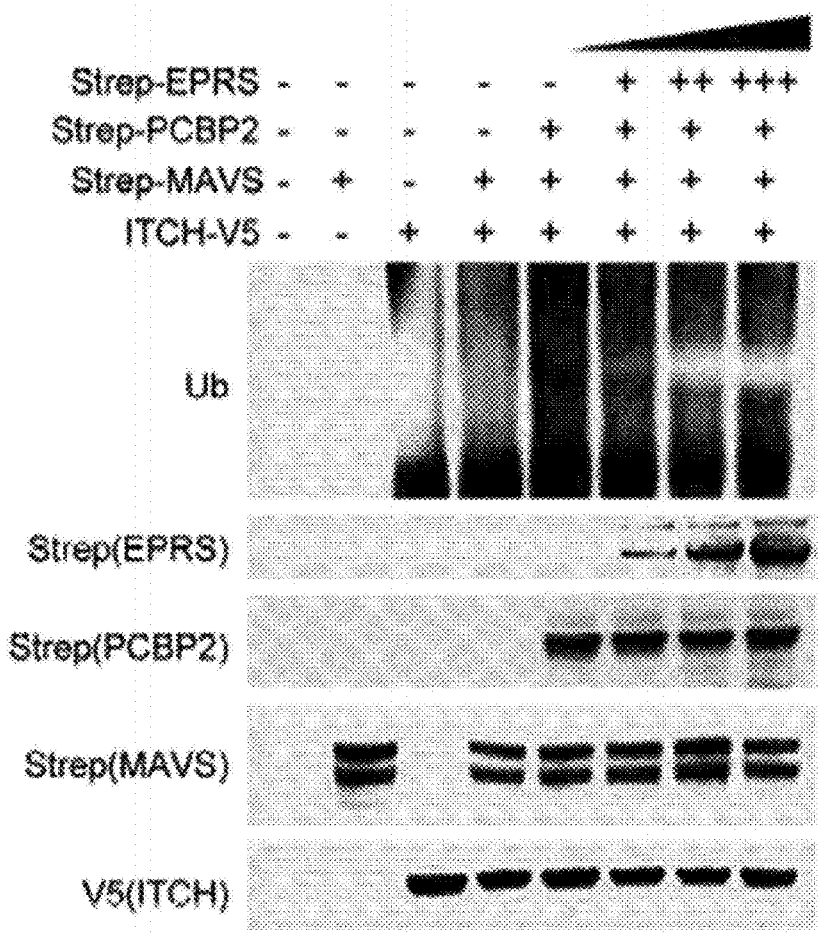

[FIG. 99]
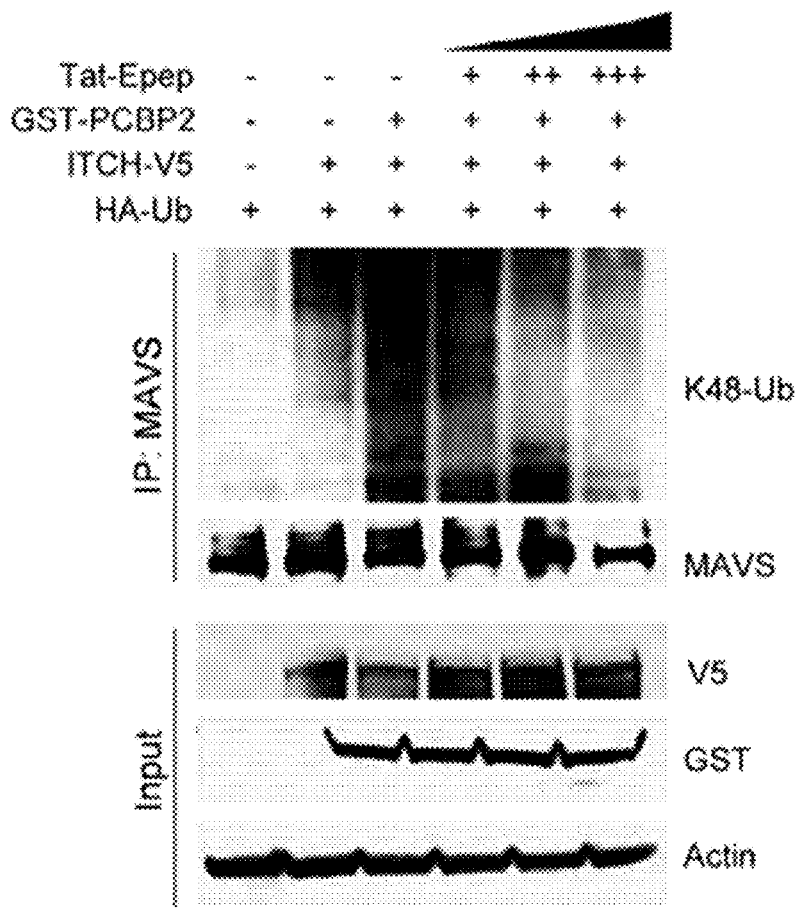
(SEQ ID NO 60)
Tat: YGRKKRRQRRR
(SEQ ID NO 61)
Tat-Epep: YGRKKRRQRRR-GG-DVSTTKARVAPEKKQDVGKFVELPGAEMG

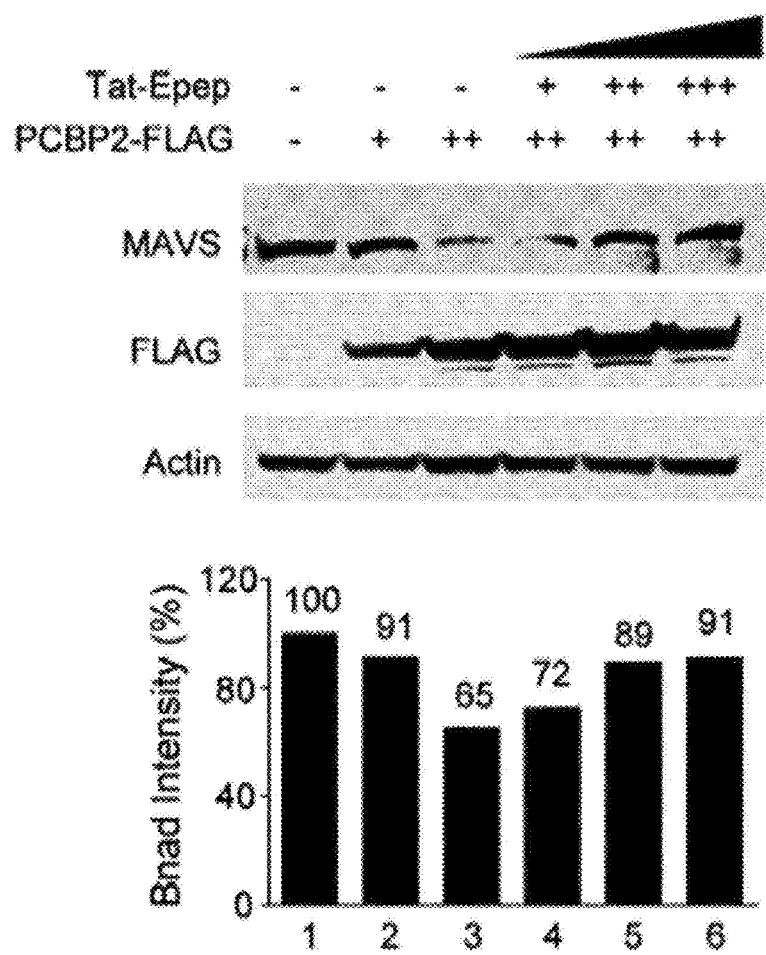
[FIG. 100]

[FIG. 101]
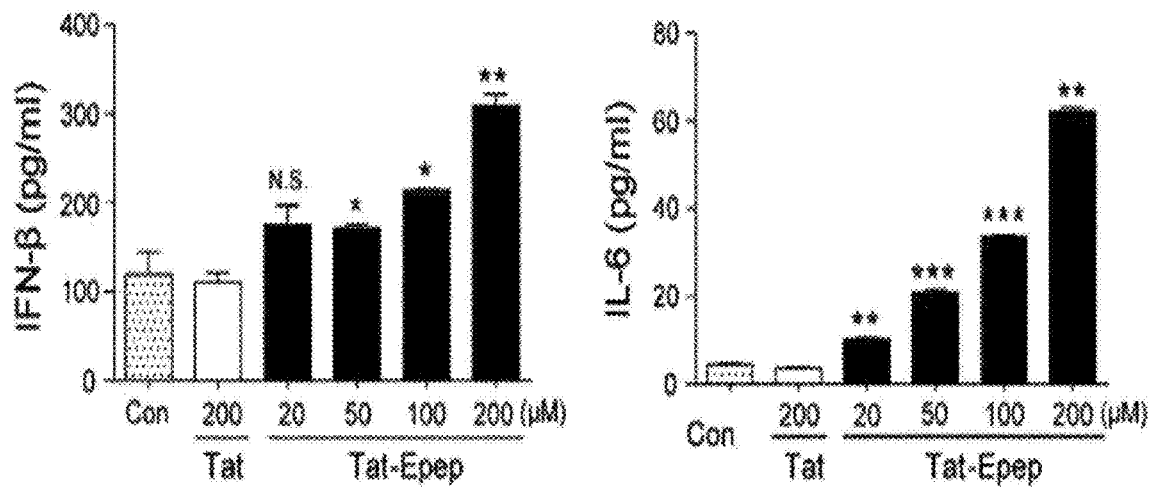
[FIG. 102]
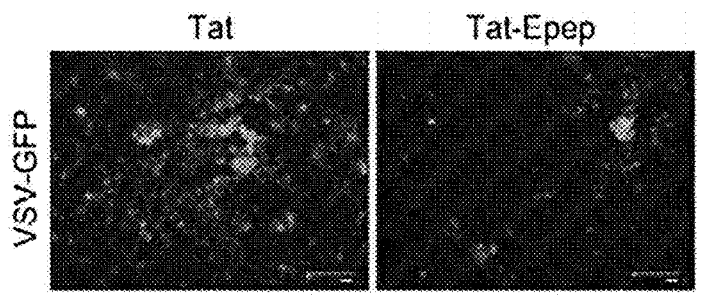

[FIG. 103]
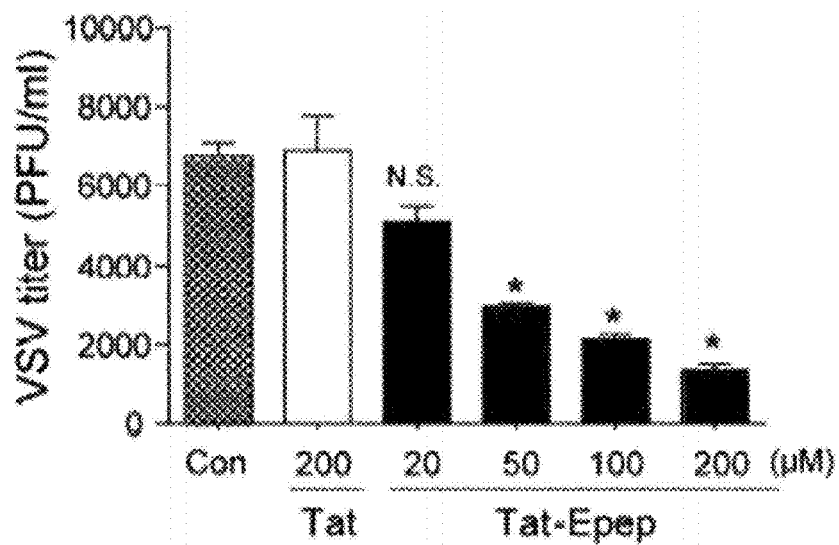
[FIG. 104]
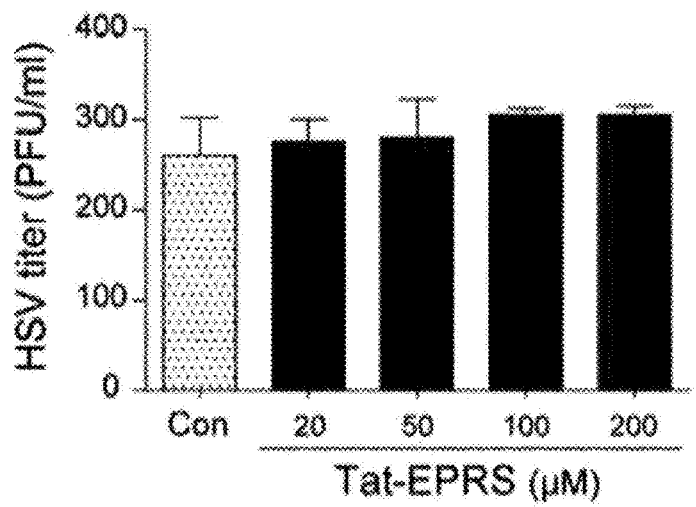

[FIG. 105]
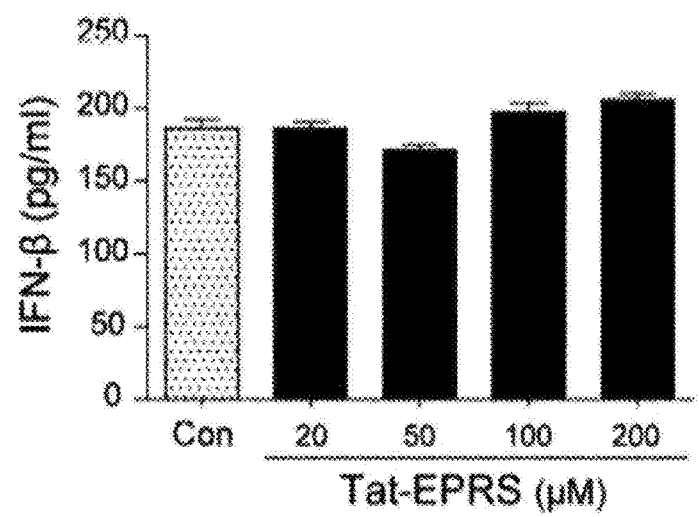
[FIG. 106]
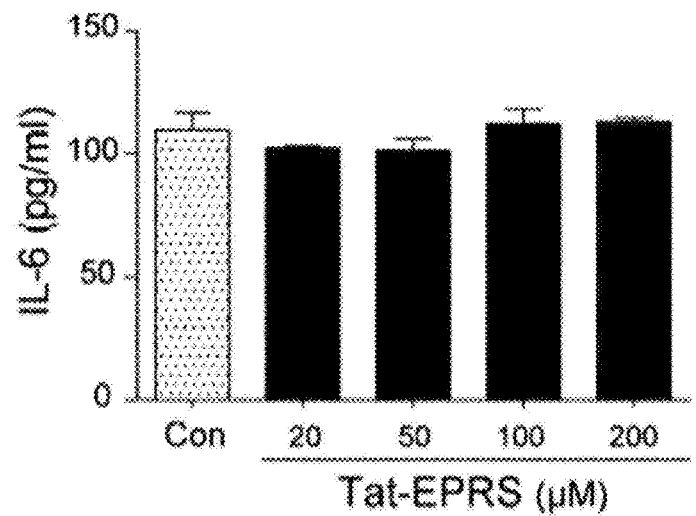

[FIG. 107]
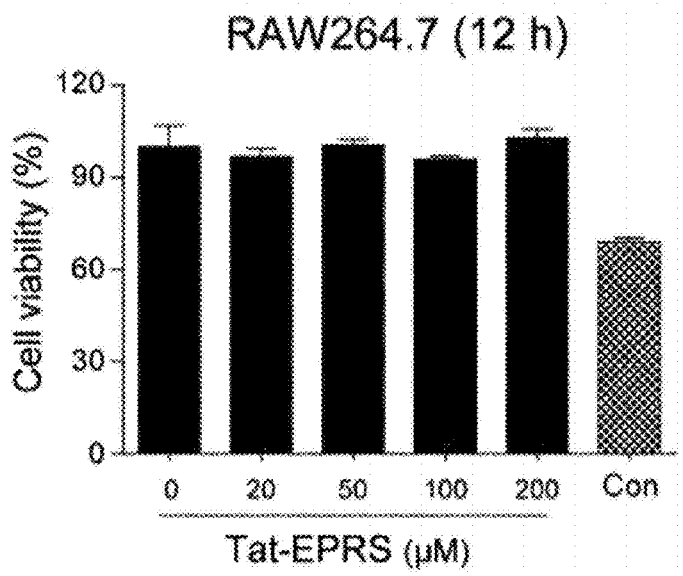
[FIG. 108]
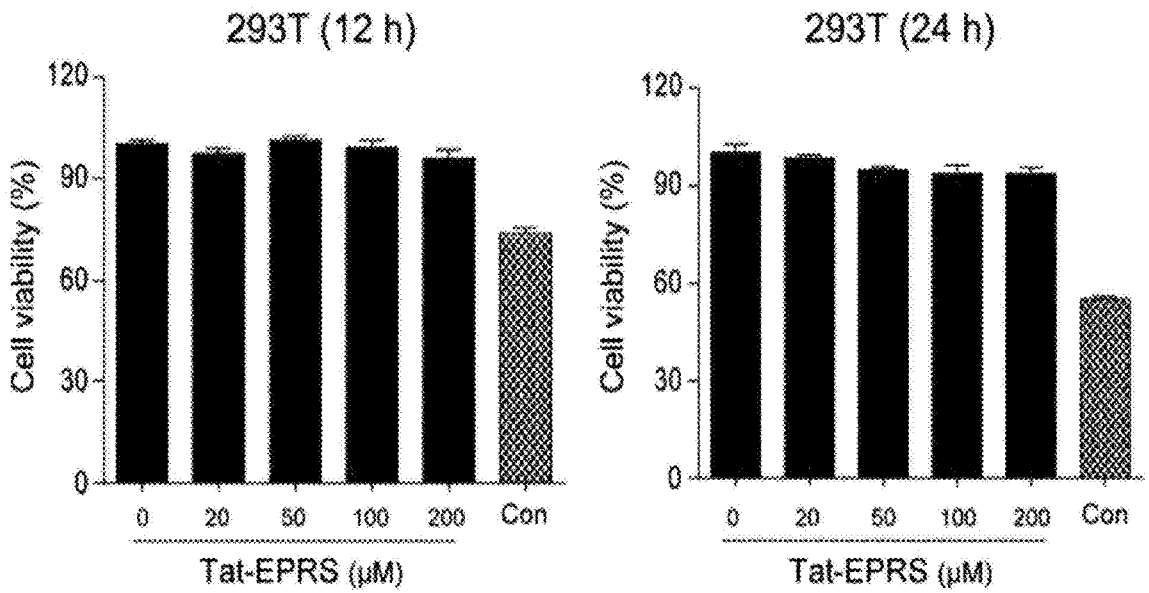

[FIG. 109]
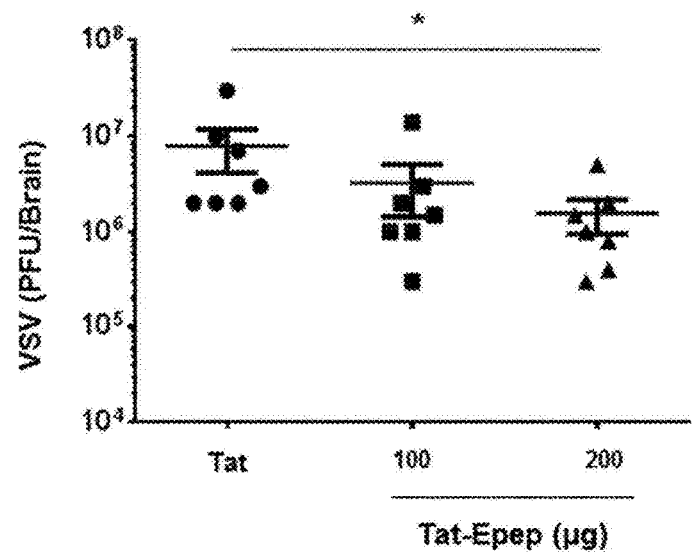
[FIG. 110]
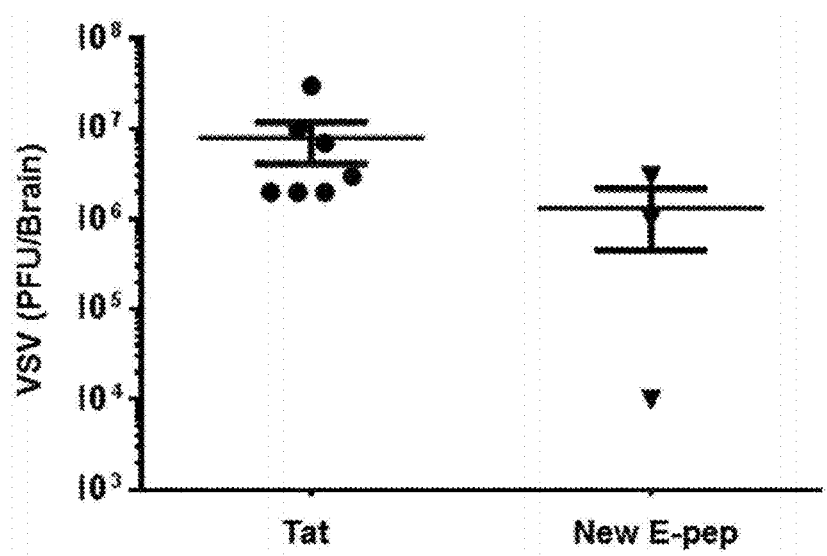

[FIG. 111]
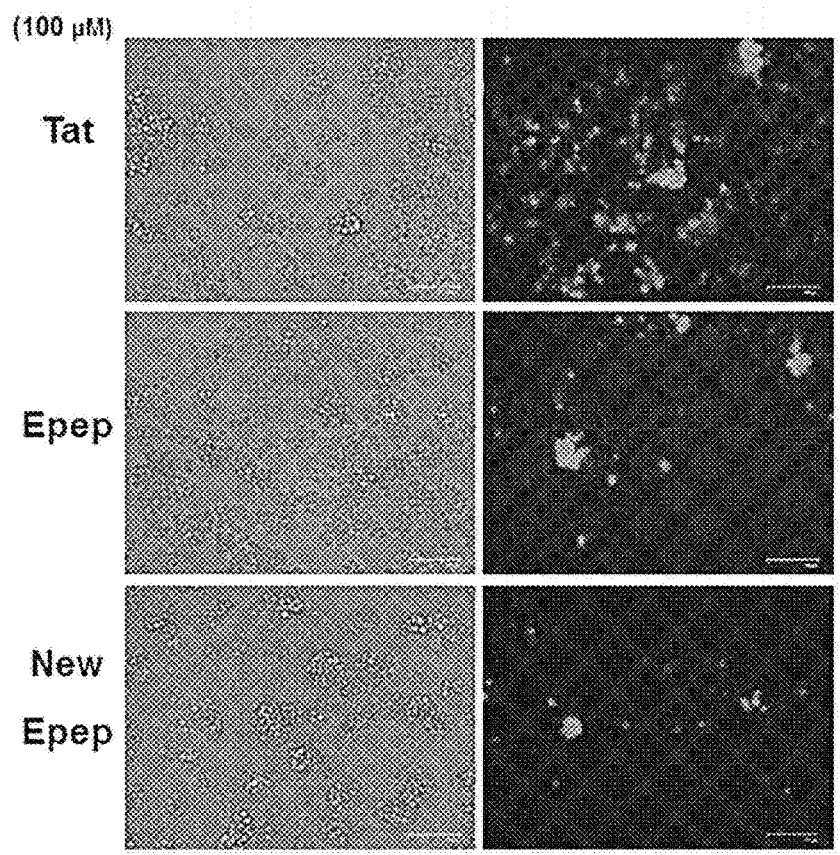
[FIG. 112]
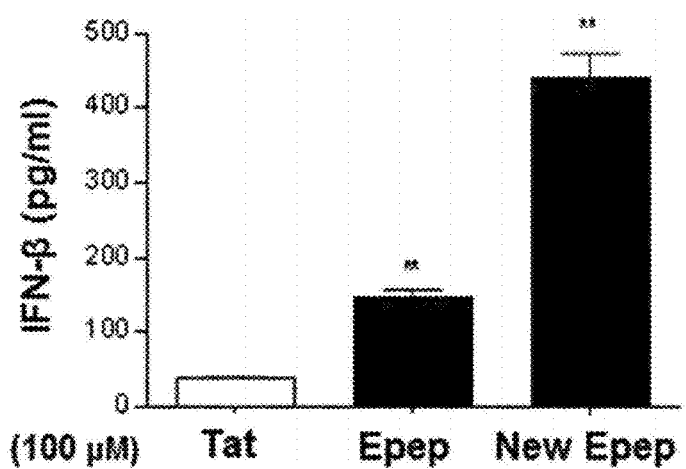

[FIG. 113]
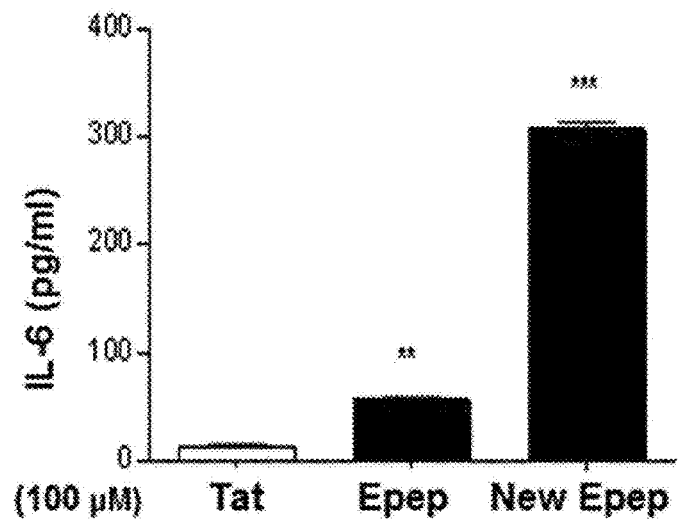
[FIG. 114]
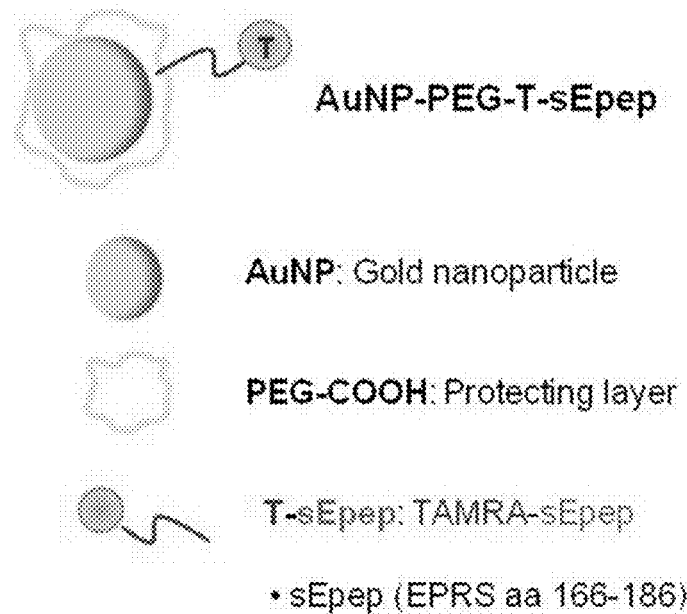

[FIG. 115]
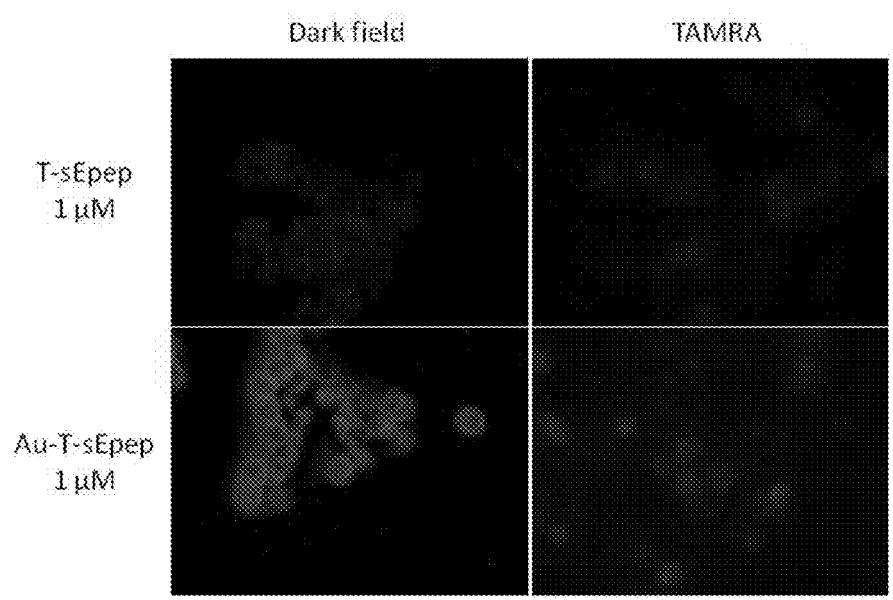

ANTI-RNA VIRUS COMPOSITION COMPRISING EPRS PROTEIN OR FRAGMENT THEREOF

SEQUENCE LISTING SUBMISSION VIA EFS-WEB

A computer readable text file, entitled "105135-5010 SL.txt" created on Sep. 28, 2021 with a file size of 34,062 bytes contains the sequence listing for this application and is hereby incorporated by reference in its entirety.

BACKGROUND OF THE INVENTION

1. Field of the Invention

The present invention relates to an anti-RNA virus composition comprising an EPRS (glutamyl-prolyl-tRNA synthetase) protein or a fragment thereof, a composition for preventing or treating a RNA viral infectious disease, and a method of preventing or treating a RNA viral infectious disease using the composition.

2. Description of the Related Art

Aminoacyl-tRNA synthetases (ARSs) are essential enzymes for catalysis of aminoacylation, and ensure high-fidelity protein synthesis. The catalytic domains of ARSs are highly conserved throughout the three kingdoms. Cytoplasmic ARSs have undergone substantial changes during the evolution of higher eukaryotes, comprising the addition of new domain switches with unique structural characteristics that are neither part of the enzymatic core nor present in prokaryotic homologues. Notably, these appended regions are associated with a broad range of biological functions. Thus, ARSs have been known as a new class of regulatory proteins with roles beyond protein synthesis. The activity of many ARSs in higher eukaryotes appears to be regulated by their presence in a cytoplasmic depot system called the "multi-tRNA synthetase complex (MSC)". The MSC is assembled in most cases via the appended domains and consists of eight tRNA synthetases, comprising glutamyl-prolyl-tRNA syntetase (EPRS), and three ARS-interacting multifunctional proteins (AIMP1/p43, AIMP2/p38, and AIMP3/p38) (Trends Biochem. Sci. 2007, 35: 158-164).

Under conditions of stress, several MSC components, which comprise EPRS, methionyl-tRNA synthetase (MRS), lysyl-tRNA synthetase (KRS), AIMP1, and AIMP2, are released from the complex through post-translational modifications to exert activities during non-translational events such as inflammation, cell metabolism, angiogenesis, and tumorigenesis (Trends Biochem. Sci, 2009, 34: 324-331). Phosphorylation is a critical regulatory mechanism that determines the non-translational function of ARSs in cells. A representative example of this involves EPRS which is the only bifunctional tRNA synthetase. EPRS comprises ERS and PRS, which are coupled together via a linker containing three WHEP domains. EPRS is thought to reside at the exterior of MSC, consistent with its susceptibility to inducible release from MSC. The residues Ser886 and Ser999 located between ERS and PRS domains of EPRS are sequentially phosphorylated following stimulation by IFN-γ, which promotes its dissociation from the MSC. Once EPRS escapes MSC, it associates with nonstructural-protein-1-associated protein 1 (NSAP1), phosphorylated ribosomal protein L13a, and glyceraldehyde-3-phosphate dehydrogenase (GAPDH) to form the IFN-γ-activated inhibitor of translation (GAIT) complex. This regulatory complex binds to distinct 3'-UTRs (untranslated regions) of mRNAs that encode inflammatory proteins such as ceruloplasmin (Cp) and thus suppresses their translation. This specific function is thought to contribute to the resolution of chronic inflammation by controlling the expression of injurious pro-inflammatory molecules generated in response to the initial insults during infection. However, it is noted that IFN-γ is produced in the context of an adaptive immune response during the late phase of infection and is secreted mainly by IL-12-activated natural killer (NK) cells or Th1 cells.

The innate immune response is the first line of defense during the early phase of infection. Antiviral signaling is an essential cellular process that has evolved to respond to viral infection. The signaling is mainly activated by RIG-I-like receptor (RLR) pathways, which comprise the key cytosolic sensors retinoic acid-inducible gene-I (RIG-I) and melanoma differentiation-associated protein 5 (MDA5), which detect viral RNA. These sensors subsequently interact with the central antiviral signaling protein mitochondria antiviral signaling protein (MAVS), which in turn activates the transcription factors NF-κB and IRF3 via the cytosolic kinases IKK and TBK1, respectively. This cascade ultimately leads to induction of type I IFN and other antiviral molecules (Cell, 2006, 124, 783-801). These signaling pathways are finely tuned by positive and negative regulatory mechanisms, which control antiviral responses through a complex network of proteins. Therefore, since RLR pathway is activated by viral RNA, leading to activation of immune response by MAVS, universal antiviral activities against RNA viruses could be achieved by prevention of MAVS degradation.

The present inventors have made intensive efforts to develop an anti-viral composition capable of preventing or treating viral infections, and as a result, they found that one of the MSC components, EPRS protein, or a fragment thereof, protects the central antiviral signaling protein MAVS from its negative regulator poly(rC)-binding protein 2 (PCBP2) via infection-specific modification, and ultimately, it has prophylactic and therapeutic effects on viral infection, thereby completing the present invention.

SUMMARY OF THE INVENTION

An object of the present invention is to provide a composition comprising a glutamyl-prolyl-tRNA synthetase (EPRS) protein or a fragment thereof, wherein the fragment of the EPRS protein comprises an amino acid sequence at positions 168 to 186 in SEQ ID NO: 63.

Another object of the present invention is to provide an EPRS protein or a fragment thereof, wherein the fragment of the EPRS protein comprises an amino acid sequence at positions 168 to 186 in SEQ ID NO: 63.

Still another object of the present invention is to provide a polynucleotide encoding the protein or the fragment thereof.

Still another object of the present invention is to provide a vector comprising the polynucleotide.

Still another object of the present invention is to provide a transformant comprising the polynucleotide or the vector.

Still another object of the present invention is to provide a pharmaceutical composition for preventing or treating a RNA viral infectious disease, the pharmaceutical composition comprising the composition.

Still another object of the present invention is to provide a method of treating a RNA viral infectious disease, comprising administering an EPRS protein, or a fragment thereof, or a composition comprising the EPRS protein or the fragment thereof to a subject.

Still another object of the present invention is to provide a quasi-drug composition for preventing or improving a RNA viral infectious disease, the quasi-drug composition comprising the composition.

Still another object of the present invention is to provide a food composition for preventing or improving a RNA viral infectious disease, the food composition comprising the composition.

Still another object of the present invention is to provide a cosmetic composition for preventing or improving a RNA viral infectious disease, the cosmetic composition comprising the composition.

Still another object of the present invention is to provide a feed composition for preventing or improving a RNA viral infectious disease, the feed composition comprising the composition.

Still another object of the present invention is to provide a method of preventing or inhibiting MAVS protein degradation, comprising administering an EPRS protein, or a fragment thereof, or a composition comprising the EPRS protein or the fragment thereof.

Still another object of the present invention is to provide a method of inhibiting binding of PCBP2 to MAVS, comprising administering an EPRS protein, or a fragment thereof, or a composition comprising the EPRS protein or the fragment thereof to a subject.

BRIEF DESCRIPTION OF THE DRAWINGS

FIG. 1 shows MSC genes (change of over 1.5-fold) upregulated (gray) or downregulated (black) in PR8-infected bronchial epithelial cells.

FIG. 2 shows IFN-β promoter activation induced by EPRS. For luciferase analysis of selected MSC genes, 293T cells were transfected with a plasmid encoding IFN-β promoter, together with a plasmid encoding N-terminal domain of RIG-I (N-RIG-I). Con represents those not transfected with N-RIG-I.

FIG. 3 shows EPRS expression in a variety of virus-infected cell lines.

FIG. 4 shows immunoblot analysis of EPRS expression. RAW246.7 cells were transfected with a non-targeting control siRNA (siCon) or siEPRS.

FIG. 5 shows analysis of viral replication by fluorescence microscopy (fluorescence microscope, upper panel; phase microscope, lower panel). RAW264.7 cells were transfected with siControl (siCon) or siEPRS.

FIG. 6 shows fluorescence analysis and plaque assay at 24 hours after infection with PR8-GFP (MOI=1) or VSV-GFP (MOI=0.5). RAW264.7 cells were transfected with siControl (siCon) or siEPRS.

FIG. 7 shows viral titers after infection with HSV-GFP (MOI=1) RAW246.7 cells were transfected with a non-targeting control siRNA (siCon) or siEPRS.

FIG. 8 shows IFN-β levels in culture supernatants of cells infected with PR8-GFP, VSV-GFP, or HSV-GFP (MOI=1) or treated with poly(I:C) (80 μg). RAW264.7 cells were transfected with siControl (siCon) or siEPRS.

FIG. 9 shows IL-6 levels in culture supernatants of cells infected with PR8-GFP, VSV-GFP, or HSV-GFP (MOI=1) or treated with poly(I:C) (80 μg). RAW264.7 cells were transfected with siControl (siCon) or siEPRS FIG. 10 shows fluorescence microscopic images of 293T cells infected with VSV-GFP (MOI=0.0001) following transfection with siCon or siEPRS for 36 hours.

FIG. 11 shows viral replication in 293T cells infected with VSV-GFP (MOI=0.0001) following transfection with siCon or siEPRS for 36 hours.

FIG. 12 shows IFN-β or IL-6 secretion level in 293T cells infected with VSV-GFP (MOI=0.0001) following transfection with siCon or siEPRS for 36 hours.

FIG. 13 shows immunoblot analysis of EPRS expression in cells infected with PR8-GFP (MOI=1). RAW264.7 cells were introduced with a non-targeting control shRNA (shCon) or EPRS shRNA (shEPRS), and selected using puromycin.

FIG. 14 shows fluorescence microscopic images of cells infected with PR8-GFP (MOI=1). RAW264.7 cells were introduced with a non-targeting control shRNA (shCon) or EPRS shRNA (shEPRS), and selected using puromycin.

FIG. 15 shows PR8 titer in cells infected with PRS-GFP (MOI=1) RAW264.7 cells were introduced with a non-targeting control shRNA (shCon) or EPRS shRNA (shEPRS), and selected using puromycin.

FIG. 16 shows IFN-β or IL-6 secretion level in cells infected with PR8-GFP (MOI=1). RAW264.7 cells were introduced with a non-targeting control shRNA (shCon) or EPRS shRNA (shEPRS), and selected using puromycin.

FIG. 17 shows fluorescence microscopic images of stable EPRS-depleted cells infected with VSV-GFP RAW264.7 cells were introduced with a non-targeting control shRNA (shCon) or EPRS shRNA (shEPRS), and selected using puromycin.

FIG. 18 shows VSV titer in stable EPRS-depleted cells infected with VSV-GFP. RAW264.7 cells were introduced with a non-targeting control shRNA (shCon) or EPRS shRNA (shEPRS), and selected using puromycin.

FIG. 19 shows IFN-β or IL-6 secretion level in stable EPRS-depleted cells infected with VSV-GFP RAW264.7 cells were introduced with a non-targeting control shRNA (shCon) or EPRS shRNA (shEPRS), and selected using puromycin.

FIG. 20 shows immunoblot analysis of phosphorylation or inactivation of IRF3 and STAT1, and expression of EPRS and actin. RAW264.7 cells expressing EPRS-specific shRNA (shEPRS) or control shRNA (shCon) were infected with PR8-GFP at the indicated time.

FIG. 21 shows immunoblot analysis of EPRS expression. RAW264.7 cells were transfected with FLAG-tagged empty vector (Con) or EPRS-FLAG (EPRS) plasmid, and selected using puromycin.

FIG. 22 shows fluorescence microscopic analysis of PR8-GFP-infected empty vector (Con) or EPRS knock-in RAW264.7 cells.

FIG. 23 shows fluorescence analysis and plaque assay of PR8-GFP-infected, empty vector (Con) or EPRS knock-in RAW264.7 cells.

FIG. 24 shows IFN-β or IL-6 secretion of PR8-GFP-infected, empty vector (Con) or EPRS knock-in RAW264.7 cells.

FIG. 25 shows fluorescence microscopic images of VSV-GFP (MOI=0.5)-infected, EPRS-overexpressing cells. RAW264.7 cells were transfected with a FLAG-tagged empty vector (Con) or EPRS-FLAG (EPRS) plasmid, and selected using puromycin.

FIG. 26 shows VSV titer in VSV-GFP (MOI=0.5)-infected, EPRS-overexpressing cells. RAW264.7 cells were transfected with a FLAG-tagged empty vector (Con) or EPRS-FLAG (EPRS) plasmid, and selected using puromycin.

FIG. 27 shows IFN-β or IL-6 secretion level in VSV-GFP (MOI=0.5)-infected, EPRS-overexpressing cells RAW264.7 cells were transfected with a FLAG-tagged empty vector (Con) or EPRS-FLAG (EPRS) plasmid, and selected using puromycin.

FIG. 28 shows viral titers assessed by plaque analysis. BMDMs of EPRS$^{+/+}$ and EPRS$^{+/-}$ mice were infected with VSV-GFP (MOI=5) and PR8-GFP (MOI=3).

FIG. 29 shows IFN-β and IL-6 levels in culture supernatants at 12 or 24 hours after viral infection. BMDMs of EPRS$^{+/+}$ and EPRS$^{+/-}$ mice were infected with VSV-GFP (MOI=5) and PR8-GFP (MOI=3).

FIG. 30 shows IFN-β and IL-6 levels in culture supernatants at 12 or 24 hours after poly(I:C) treatment. BMDMs of EPRS$^{+/+}$ and EPRS$^{+/-}$ mice were treated with poly(I:C) (40 μg).

FIG. 31 shows immunoblot analysis of EPRS expression in BMDMs. BMDMs were transfected with a non-targeting control siRNA (siCon) or siEPRS for 36 hours.

FIG. 32 shows viral titers assessed by plaque analysis at 12 and 24 hours after infection. BMDMs were infected with PR8-GFP (MOI=3) or VSV-GFP (MOI=5).

FIG. 33 shows IFN-β and IL-6 levels assessed by ELISA at 12 and 24 hours after infection. BMDMs were infected with PR8-GFP (MOI=3) or VSV-GFP (MOI=5).

FIG. 34 shows IFN-β and IL-6 levels in BMDM culture supernatants treated with 40 μg of poly(I:C).

FIG. 35 shows expression of IFN-β, IL-6, and other IFN-related anti-viral genes in BMDMs derived from EPRS$^{+/+}$ and EPRS$^{+/-}$ mice at 12 hours after infection with VSV-GFP.

FIG. 36 shows whether IFN-β mRNA or IFN-related anti-viral gene expression in virus-infected cells is induced. RAW264.7 cells were transfected with siCon or siEPRS for 36 hours, and then infected with PR8-GFP (MOI=1) for 12 hours. The genes shown in the graphs were normalized against gapdh expression and presented as fold induction.

FIG. 37 shows viral titers (assessed by plaque analysis) in cell culture supernatants after infection with HSV-GFP. BMDMs derived from EPRS$^{+/+}$ and EPRS$^{+/-}$ mice were infected with HSV-GFP (MOI=2).

FIG. 38 shows IFN-β or IL-6 secretion level in cell culture supernatants after infection with HSV-GFP. BMDMs derived from EPRS$^{+/+}$ and EPRS$^{+/-}$ mice were infected with HSV-GFP (MOI=2).

FIG. 39 shows a survival rate for 10 days of age- and sex-matched EPRS$^{+/+}$ (n=15) and EPRS$^{+/-}$ (n=14) mice after intravenous administration of VSV-Indiana (2×10$^8$ pfu/mouse).

FIG. 40 shows viral loads in brain and spleen tissues of EPRS$^{+/+}$ and EPRS$^{+/-}$ mice (n=6), assessed by plaque assay at day 5 after infection.

FIG. 41 shows viral loads determined by qPCR of VSV transcripts (n=5).

FIG. 42 shows viral loads assessed by plaque assay. Sera were collected from EPRS$^{+/+}$ and EPRS$^{+/-}$ mice (n=8) at 12 hours after infection with VSV-GFP (2×10$^8$ pfu/mouse), and used in the assay.

FIG. 43 shows IFN-β, IFN-α, and IL-6 levels determined by ELISA. Sera were collected from EPRS$^{+/+}$ and EPRS$^{+/-}$ mice (n=8) at 12 hours after infection with VSV-GFP (2×10$^8$ pfu/mouse), and used in the assay.

FIG. 44 shows neural parenchyma obtained from H&E-stained sections of brain tissue from EPRS$^{+/+}$ and EPRS$^{+/-}$ mice (n=4) at 5 days after infection with VSV-Indiana (i-iii). Glial nodule formation by reactive microglial cells and mononuclear cells in brain parenchyma is indicated by black arrows, and perivascular cuffing is indicated by arrowhead. Disruption of the ependymal lining (red arrows, iv) at the lateral ventricle (LV), a result of massive infiltration of mononuclear cells, was observed. Con represents a non-viral infected sample.

FIG. 45 shows results of immunohistochemical analysis, stained with anti-VSV-G antibody, of brain sections (n=4) at days 3 and 5 after infection with VSV-Indiana. Nuclei were stained with DAPI. VSV-positive GFP signals were indicated by white arrows. Con represents a non-viral infected sample.

FIG. 46 shows results of endogenous co-IP, with anti-EPRS antibody, followed by immunoblot analysis with anti-KRS and anti-AIMP3 (a MSC component) antibodies, and anti-NSAP1 and anti-GAPDH (GAIT complex components) antibodies, after infection of U937 cells with PR8-GFP (MOI=3) or treatment with IFN-γ (500 units/mL).

FIG. 47 shows EPRS release from the MSC components, induced by viral infection. IP of cell lysates of RAW264.7 cells infected with PR8-GFP (MOI=1) was performed using anti-EPRS antibody, followed by immunoblot analysis with anti-KRS, anti-MRS, anti-AIMP3, and anti-GAPDH antibodies.

FIG. 48 shows EPRS release from the MSC components, induced by viral infection. IP of cell lysates of RAW264.7 cells infected with PR8-GFP (MOI=1) was performed using anti-KRS antibody, followed by immunoblot analysis with anti-EPRS and anti-AIMP3 antibodies.

FIG. 49 shows confocal microscopy for assessing whether colocalization of endogenous EPRS (red) and KRS (green) is detected or not. Cells were infected with PR8 (MOI=5) for 6 or 12 hours, or treated with IFN-γ (1,000 units/mL) for 12 hours. Scale bars, 10 μm.

FIG. 50 shows colocalization index of EPRS and KRS.

FIG. 51 shows confocal microscopy of endogenous EPRS (red) and KRS (green) expression in HeLa cells infected with PR8 (MOI=5) for 6 or 12 hours, which were compared with those treated with IFN-γ (1,000 units/mL) for 12 hours. Scale bars, 10 μm (enlarged image: 2 μm).

FIG. 52 shows silver staining of Strep-EPRS purified by Strep precipitation from 293T cells infected with or 293T cells (−) not infected with PR8-GFP (MOI=5). EPRS protein was marked by *. EV, Strep-tagged empty vector.

FIG. 53 shows MS/MS spectrum of a doubly charged EPRS peptide EYIPGQPPLSQSSDSpS*PTR (MH+= 2125.93, z=2+, SEQ ID NO: 65) obtained under non-infected (−, upper panel) and PR8-infected (PR8, lower panel) conditions. The peptides comprise a S886-phosphorylation site (marked by *). Fragment ions were labeled according to the nomenclature for peptide fragmentation in the mass spectrometry.

FIG. 54 shows extracted ion chromatogram (XIC) of a doubly charged EYIPGQPPLSQSSDSSPTR (MH+= 2044.96, z=2+, SEQ ID NO: 66) peptide derived from non-phosphorylated (left) and phosphorylated (right) EPRS by tryptic digestion under non-infected (−, upper panel) and infected (PR8, lower panel) conditions. The phosphorylated residue is marked by *, and N.D. represents not detected.

FIG. 55 shows XIC (Extracted ion chromatogram) of a doubly charged NQGGGLSSSGAGEGQGPK (MH+= 1586.72, z=2+, SEQ ID NO: 67) peptide (left) derived from non-phosphorylated EPRS and a doubly charged NQGGGLSS*SGAGEGQGPK (SEQ ID NO: 68) peptide (right) derived from phosphorylated EPRS by tryptic digestion under non-infected (−, upper panel) and infected (PR8, lower panel) conditions. The phosphorylated residue is marked by *, and N.D. represents not detected.

FIG. 56 shows MS/MS spectrum of triply charged EPRS peptides, KDPSKNQGGGLSSSGAGEGQGPK [MH+=

2142.02, z=3+, SEQ ID NO: 69; non-infected condition (−, left panel)] and KDPpS*KNQGGGLSSSGAGEGQGPK [MH+=2222.99, z=3+, SEQ ID NO: 70. PR8-infected condition (PR8, right panel)]. The latter comprises the Ser990-phosphorylation site (marked by *).

FIG. 57 shows XIC (Extracted ion chromatogram) of a triply charged KDPSKNQGGGLSSSGAGEGQGPK (MH+= 2142.02, z=3+, SEQ ID NO: 69) peptide derived from non-phosphorylated (left) and phosphorylated (right) EPRS by tryptic digestion under non-infected (−, upper panel) and infected (PR8, lower panel) conditions. The phosphorylated residue is marked by *, and N.D. represents not detected.

FIG. 58 shows immunoblot analysis of EPRS phosphorylated at Ser990 in U937 cells infected with PR8-GFP or treated with IFN-γ.

FIG. 59 shows immunoblot analysis of EPRS phosphorylated at Ser990 in RAW264.7 cells infected with PR8-GFP (MOI=1).

FIG. 60 shows immunoblot analysis of EPRS phosphorylated at Ser990 in 293T cells infected with PR8-GFP (MOI=5).

FIG. 61 shows immunoblot analysis of EPRS phosphorylated at Ser990 in 293T cells infected with VSV-GFP (MOI=0.001).

FIG. 62 shows immunoblot analysis of EPRS phosphorylated at Ser9) in cells transfected with 2 μg of poly(I:C).

FIG. 63 shows immunoblot analysis of EPRS phosphorylated at Ser886 in U937 cells infected with PR8-GFP or treated with IFN-γ.

FIG. 64 shows immunoblot analysis of EPRS phosphorylated at Ser999 in U937 cells infected with PR8-GFP or treated with IFN-γ.

FIG. 65 shows IFN-γ secretion levels in U937 cells infected with PR8-GFP or VSV-GFP. As a positive control, cells treated with IFN-γ (1000 units/mL) for 24 hours were used.

FIG. 66 shows IFN-γ secretion levels in RAW264.7 cells infected with PR8-GFP or VSV-GFP. As a positive control, cells treated with IFN-γ (1.000 units/mL) for 24 hours were used.

FIG. 67 shows immunoblot analysis of Cp expression in RAW264.7 cells infected with PR8-GFP.

FIG. 68 shows release of Ser99) phosphomimetic EPRS from MSC, 293T cells were transfected with an empty vector (EV), Strep-EPRS WT, or three phosphomimetic forms, followed by Strep precipitation and immunoblot analysis with anti-KRS, anti-AIMP3, and anti-MRS antibodies.

FIG. 69 shows IFN-β promoter activation in 293T cells transfected with N-RIG-I. MDA5, poly(I:C), or MAVS, together with an EPRS-FLAG plasmid (0 ng, 50 ng, 200 ng, or 800 ng).

FIG. 70 shows IFN-β promoter activation in 293T cells transfected with TRAF3, TBK1, or IRF7, together with an EPRS-FLAG plasmid (0 ng, 50 ng, 200 ng, or 800 ng).

FIG. 71 shows silver staining of Strep-EPRS complexes purified from 293T cells at 24 hours after transfection with a Strep-EPRS plasmid, followed by infection for 6 hours with PR8-GFP (MOI=5). The protein marked by * represents PCBP2 (38 kDa). The sequence represents a peptide identified by mass spectrometry.

FIG. 72 shows interaction between EPRS and PBP2 in PR8-infected RAW264.7 cells, assessed by immunoprecipitation with anti-EPRS antibody and immunoblot analysis with anti-PCBP2 antibody.

FIG. 73 shows interaction between EPRS and PBP2 in PR8-infected U937 cells, assessed by immunoprecipitation with anti-EPRS antibody and immunoblot analysis with anti-PCBP2 antibody.

FIG. 74 shows confocal analysis of endogenous EPRS (red) and PCBP2 (green) expression in HeLa cells infected with PR8 virus (MOI=5). Scale bars, 10 μm.

FIG. 75 shows an illustration of EPRS used in the present invention and fragments thereof. Whether of EPRS binds to PCBP2 or not is represented by (+ or −). GST, GST-like domain; L, linker; CD, catalytic domain; tRNA, tRNA-binding domain; W, WHEP domain.

FIG. 76 shows whether EPRS or fragments thereof interact with PCBP2. 293T cells were transfected with an empty vector (EV), PCBP2 or EPRS plasmid.

FIG. 77 shows luciferase reporter assay of IFN-β promoter activation. 293T cells were transfected with expression plasmids comprising N-RIG-I, IFN-β promoter, and TK-Renilla, together with EV or indicated EPRS plasmids.

FIG. 78 shows whether EPRS or fragments thereof interact with PCBP2 293T cells were transfected with an empty vector (EV), PCBP2 or EPRS plasmid.

FIG. 79 shows luciferase reporter assay of IFN-β promoter activation. 293T cells were transfected with expression plasmids comprising N-RIG-I, IFN-β promoter, and TK-Renilla, together with EV or indicated EPRS plasmids.

FIG. 80 shows whether EPRS or fragments thereof interact with PCBP2. 293T cells were transfected with an empty vector (EV). PCBP2 or EPRS plasmid.

FIG. 81 shows luciferase reporter assay of IFN-β promoter activation. 293T cells were transfected with expression plasmids comprising N-RIG-I, IFN-β promoter, and TK-Renilla, together with EV or indicated EPRS plasmids.

FIG. 82 shows illustration of PCBP2 constructs. Whether PCBP2 binds to EPRS or not was represented.

FIG. 83 shows that PCBP2 KH1 is essential for interaction with EPRS. The interaction with PCBP2 was examined by Strep precipitation of lysates of 293T cells expressing Strep-EPRS and various forms of GST-PCBP2, followed by immunoblot analysis with anti-GST antibody.

FIG. 84 shows in vitro precipitation analyzing whether EPRS (aa 1-732, aa 1-196, and aa 1-168) and PCBP2 KH1 (aa 11-82) domain are directly bound. Black arrows represent protein fragments derived from EPRS during purification. N-terminal sequences of the marked bands were identified as MRFDD (aa 234-238) and MVTFI (aa 565-569) sequences of EPRS. Red arrowheads represent PCBP2 KH1 domain.

FIG. 85 shows interaction between EPRS and PCBP2. Purified His-tagged EPRS (aa 1-196) was mixed with GST-fused PCBP2 KH1 (aa 11-82). After precipitation of His-tag, proteins were subjected to SDS-PAGE, followed by Coomassie Brilliant Blue staining. FT represents a flow-through fraction.

FIG. 86 shows interaction between EPRS and PCBP2. Purified His-tagged EPRS (aa 1-186) was mixed with GST-fused PCBP2 KH1 (aa 11-82). After precipitation of His-tag, proteins were subjected to SDS-PAGE, followed by Coomassie Brilliant Blue staining. FT represents a flow-through fraction.

FIG. 87 shows interaction between PCBP2 KH1 domain and MAVS. The interaction with PCBP2 was confirmed by co-IP of lysates of 293T cells transfected with MAVS and various PCBP2 plasmids with anti-FLAG antibody, followed by immunoblot analysis with anti-GST antibody.

FIG. 88 shows in vitro precipitation assay of the interaction between PCBP2 KH1 domain and MAVS. The arrowhead represents MAVS protein.

FIG. 89 shows interaction between MAVS and PCBP2. Purified GST-fused MAVS (aa 460-540) was mixed with His-tagged PCBP2 KH1 (aa 11-82). The protein mixture was loaded onto Ni-NTA agarose beads, followed by elution with an imidazole elution buffer. FT represents a flow-through fraction.

FIG. 90 shows interaction between MAVS and PCBP2. Purified GST-fused MAVS (aa 460-540) was mixed with His-tagged PCBP2 linker (aa 168-279). The protein mixture was loaded onto Ni-NTA agarose beads, followed by elution with an imidazole elution buffer. FIT represents a flow-through fraction.

FIG. 91 shows interaction between MAVS (first panel) or EPRS (second panel) and PCBP2, confirmed by GST precipitation and immunoblot analysis with anti-FLAG or anti-Strep antibody 293T cells were transfected with MAVS and PCBP2, and treated with various amounts of EPRS.

FIG. 92 shows GST precipitation for assessing interaction between PCBP2 and ITCH (first panel) or EPRS (second panel).

FIG. 93 shows endogenous interaction between PCBP2 and EPRS or MAVS. Endogenous PCBP2 was immunoprecipitated with anti-PCBP2 antibody from cell lysate of PR8-infected RAW264.7 cells, followed by immunoblotting with anti-EPRS (first panel) or anti-MAVS (second panel) antibody.

FIG. 94 shows immunoblot analysis of exogenous MAVS with anti-K48 Ub antibody, wherein the exogenous MAVS is immunoprecipitated from lysates of 293T cells expressing various combinations of EPRS, PCBP2, ITCH, and Ub after treatment of 293T cells with MG-132.

FIG. 95 shows immunoblot analysis of endogenous MAVS with anti-K48 Ub antibody, wherein the endogenous MAVS is immunoprecipitated from lysates of 293T cells expressing various combinations of EPRS, PCBP2, ITCH, and Ub after treatment of 293T cells with MG-132.

FIG. 96 shows expression of exogenous MAVS, after treatment of PCBP2-transfected 293T cells with various concentrations of EPRS. The graph shows MAVS band intensity, normalized to that of actin.

FIG. 97 shows expression of endogenous MAVS, after treatment of PCBP2-transfected 293T cells with various concentrations of EPRS. The graph shows MAVS band intensity, normalized to that of actin.

FIG. 98 shows m vitro assay of MAVS ubiquitination by immunoblot analysis with anti-Ub antibody. Purified MAVS protein was incubated with ubiquitin, E1, E2, and a combination of purified EPRS, PCBP2, and ITCH protein.

FIG. 99 shows that EPRS L1 (aa 168-196) domain fused with cell penetrating Tat inhibited MAVS ubiquitination. 293T cells were transfected with PCBP2, ITCH, or Ub plasmid, and treated with various concentrations of Tat-Epep (20 µM, 50 µM, and 100 µM), followed by precipitation of endogenous MAVS with anti-MAVS antibody. The precipitates were immunoblotted with anti-K48 Ub A peptide (Tat-Epep) sequence obtained by fusing EPRS amino acids 168-196 with Tat is shown.

FIG. 100 shows endogenous MAVS levels, after treatment of PCBP2-transfected 293T cells with various concentrations of Tat-Epep (20 µM, 50 µM, and 100 µM). The graph shows MAVS protein band intensity, normalized to that of actin.

FIG. 101 shows that Tat-Epep promoted the secretion of IFN-β and IL-6 in VSV-infected RAW264.7 cells in a dose-dependent manner. Con represents VSV-infected RAW264.7 cells treated with PBS as a negative control group.

FIG. 102 shows representative fluorescence images of VSV-GFP-infected RAW264.7 cells treated with 100 µM of Tat or Tat-Epe.

FIG. 103 shows that Tat-Epep decreased the VSV titers in VSV-infected RAW264.7 cells in a dose-dependent manner Con represents VSV-infected RAW264.7 cells treated with PBS as a negative control group.

FIG. 104 shows that Tat-Epep had no significant effect on viral replication in RAW264.7 cells infected with HSV-GFP (MOI=1) for 12 hours. Con represents HSV-GFP-infected RAW264.7 cells treated with PBS as a negative control group.

FIG. 105 shows that Tat-Epep had no significant effect on IFN-β secretion in RAW264.7 cells infected with HSV-GFP (MOI=1) for 12 hours. Con represents HSV-GFP-infected RAW264.7 cells treated with PBS as a negative control group.

FIG. 106 shows that Tat-Epep had no significant effect on IL-6 secretion in RAW264.7 cells infected with HSV-GFP (MOI=1) for 12 hours. Con represents HSV-GFP-infected RAW264.7 cells treated with PBS as a negative control group.

FIG. 107 shows viability of RAW264.7 cells, assessed by MTS assay, after treatment with various concentrations of Tat-Epep for 12 hours. Con represents 293T cells treated with a lytic surfactant (digitonin, 30 µg/mL) as a positive control group.

FIG. 108 shows viability of 293T cells, after treatment with Tat-Epep for 12 hours or 24 hours. Con represents 293T cells treated with a lytic surfactant (digitonin, 30 µg/mL) as a positive control group.

FIG. 109 shows plaque assay of viral loads in brain tissues (n=7) of mice intraperitoneally administered with Tat-tag (1.05 µM/kg) or Tat-Epep (0.53 µM/kg or 1.05 µM/kg) daily for 3 days at 4 days after intravenous administration with VSV-Indiana ($2\times10^8$ pfu/mouse).

FIG. 110 shows inhibitory effect of New Tat-Epep on VSV virus.

FIG. 111 shows fluorescence images of reduced viral replication by treatment of VSV-GFP-infected RAW264.7 cells with Tat-Epep, and stronger inhibitory effect of New Tat-Epep on viral replication.

FIG. 112 shows IFN-β secretion according to Tat-Epep or New Tat-Epep treatment.

FIG. 113 shows IL-6 secretion according to Tat-Epep or New Tat-Epep treatment.

FIG. 114 shows an illustrative form of a conjugate wherein a drug delivery vehicle is bound to an EPRS protein or a fragment thereof.

FIG. 115 shows an intracellular delivery effect by treatment of AuNP-PEG-T-sEpep.

DETAILED DESCRIPTION OF THE PREFERRED EMBODIMENTS

The present inventors found that one of MSC (multi-tRNA synthetase complex) components, an EPRS (glutamyl-prolyl-tRNA synthetase) protein or a fragment thereof has an anti-RNA viral activity. Specifically, the EPRS protein of the present invention or the fragment thereof competes with MAVS to bind PCBP2 which degrades MAVS which plays a critical role in anti-RNA viral activity, thereby inhibiting degradation of MAVS. Accordingly, a composition comprising the protein or fragment thereof, or both of them may be used for universally effective treatment of RNA viral infectious diseases.

A specific explanation thereof is as follows. Meanwhile, each description and embodiment disclosed herein may be applied to other descriptions and embodiments, respectively. That is, all combinations of various elements disclosed herein fall within the scope of the present invention. Further, the scope of the present invention is not limited to the detailed description described below.

An aspect of the present invention to achieve the above object provides an EPRS (glutamyl-prolyl-tRNA synthetase) protein or a fragment thereof. Specifically, the fragment of the EPRS protein may comprise an amino acid sequence at positions 168 to 186 in SEQ ID NO: 63, and more specifically an amino acid sequence selected from the group consisting of an amino acid sequence at positions 1 to 196 in SEQ ID NO: 63, an amino acid sequence at positions 1 to 269 in SEQ ID NO: 63, an amino acid sequence at positions 1 to 457 in SEQ ID NO: 63, an amino acid sequence at positions 1 to 506 in SEQ ID NO: 63, an amino acid sequence at positions 1 to 682 in SEQ ID NO: 63, an amino acid sequence at positions 166 to 506 in SEQ ID NO: 63, an amino acid sequence at positions 168 to 506 in SEQ ID NO: 63, an amino acid sequence at positions 166 to 269 in SEQ ID NO: 63, an amino acid sequence at positions 168 to 269 in SEQ ID NO: 63, an amino acid sequence at positions 166 to 196 in SEQ ID NO: 63, an amino acid sequence at positions 168 to 196 in SEQ ID NO: 63, an amino acid sequence at positions 166 to 186 in SEQ ID NO: 63, and an amino acid sequence at positions 168 to 186 in SEQ ID NO: 63, but is not limited thereto.

Further, the fragment of the EPRS protein may comprise a polypeptide having at least 80% or higher, 90% or higher, 95% or higher, 97% or higher, or 99% or higher homology to the amino acid sequence at positions 168 to 186 in SEQ ID NO: 63. For example, it is apparent that an amino acid sequence having such a homology, the part of which is deleted, modified, substituted, or added, is also within the scope of the present invention, as long as the resulting amino acid sequence has an efficacy corresponding to that of the protein composed of the amino acid sequence at positions 168 to 186 in SEQ ID NO: 63.

Additionally, it does not exclude a mutation that may occur by the addition of a meaningless sequence upstream or downstream of the amino acid sequence, or a mutation that may occur naturally, or a silent mutation thereof, as long as the peptide has an activity corresponding to that of the polypeptide composed of the amino acid sequence at positions 168 to 186 in SEQ ID NO: 63.

As used herein, the term "homology" refers to a degree of matching with a given amino acid sequence or nucleotide sequence, and the homology may be expressed as a percentage. In the present specification, a homology sequence having an activity which is identical or similar to the given amino acid sequence or nucleotide sequence is expressed as "% homology" For example, the % homology may be confirmed using standard software, e.g., BLAST 2.0, for calculating parameters such as score, identity, and similarity, or by comparing sequences via Southern hybridization experiments under defined stringent conditions, and the appropriate hybridization condition to be defined may be determined by a method which is within the skill of the art and known to those skilled in the art (e.g., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York).

The EPRS protein of the present invention or the fragment thereof may be a peptide having a sequence that differs from the wild-type amino acid sequence by one or more amino acid residues. Amino acid exchanges in a protein and a polypeptide which do not entirely alter an activity are known in the art. The most commonly occurring exchanges involve an exchange between amino acid residues of Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. Further, it may include a protein having increased structural stability for heat, pH, etc. or enhanced protein activity due to mutation or modification of an amino acid sequence.

The EPRS protein fragment of the present invention may consist of 19 to 1511 amino acids. Specifically, the EPRS protein fragment above may consist of 19 to 1511 amino acids, 21 to 1511 amino acids, 19 to 682 amino acids, 19 to 506 amino acids, 19 to 457 amino acids, 19 to 341 amino acids, 19 to 339 amino acids, 19 to 269 amino acids, 19 to 196 amino acids, 19 to 104 amino acids, 19 to 102 amino acids, 19 to 31 amino acids, or 19 to 29 amino acids, but is not particularly limited thereto.

The EPRS protein of the preset invention or the fragment thereof binds to PCBP2 to block the binding between PCBP2 and MAVS, thereby having inhibitory effects on MAVS degradation. Therefore, MAVS not degraded may activate innate immune responses to viral infection by activation of its signaling pathway.

As used herein, the term "EPRS (glutamyl-prolyl-tRNA synthetase) protein" is one of ARSs (aminoacyl-tRNA synthetases), and is one component of a cytoplasmic depot system called "MSC (multi-tRNA synthetase complex)", and known to be involved in protein synthesis. However, there hale been no reports about anti-viral activity of EPRS.

Information about the EPRS protein or a gene encoding the same may be obtained from a known database such as GenBank of NCBI (National Center for Biotechnology Information), and for example, the EPRS protein may have the amino acid sequence of SEQ ID NO: 63, but is not limited thereto.

As used herein, the term "MAVS (mitochondrial antiviral-signaling protein)" refers to a crucial signaling protein that is involved in the production of various kinds of anti-viral cytokines by RIG-I and MDA5 activated after recognition of RNA virus. The absence of MAVS is known to increase the susceptibility to RNA viral infection. The EPRS protein of the present invention or the fragment thereof may block MAVS degradation to activate a signaling pathway thereof, and therefore, the composition comprising the EPRS protein or the fragment thereof may induce anti-viral activities against all RNA viruses.

In a specific embodiment of the present invention. EPRS-knockdown cells showed increased viral replication following infection with PR8 and VSV (FIGS. 5 and 6), and decreased production of antiviral cytokines after viral infection or treatment with poly(I:C) which is a mimic viral gene (FIGS. 8 and 9). In contrast, EPRS-overexpressed cells showed significantly less viral replication and more production of IFN-β and IL-6 following infection with PR8 and VSV (FIGS. 22 to 27). Further, after viral infection. EPRS$^{+/-}$ mice showed higher viral titer and lower levels of IFN-β, IFN-α, and IL-6 in the serum than the EPRS$^{+/-}$ mice (FIGS. 40 to 43), demonstrating that EPRS can positively regulate innate immune responses against RNA viruses.

In another specific embodiment of the present invention, EPRS regions involved in regulating immune responses were examined using many different sizes of EPRS fragments, and as a result, an EPRS L1 region (amino acids at positions 168 to 196 in SEQ ID NO: 63), more specifically an amino acid sequence at positions 168 to 186 in SEQ ID NO: 63, was found to be crucial for antiviral activity of EPRS (FIGS. 75 to 81). Consequently, it can be seen that since the EPRS protein or a fragment thereof comprising the amino acid sequence at positions 168 to 186 in SEQ ID NO: 63 has the anti-RNA virus activity, it may be effectively used as an anti-RNA virus composition.

As used herein, the term "RNA virus" means all viruses that use RNA as their genetic materials. For example, the RNA virus may be Amalgaviridae, Birnaviridae, Chrysoviridae, Cystoviridae, Endornaviridae, Hypoviridae, Megabirnaviridae, Partitiviridae, Picobirnarviridae, Reoviridae, Totiviridae, Quadiridae, Arteriviridae, Coronaviridae, Mesoniviridae, Roniviridae, Dicistroviridae, Iflaviridae, Marnaviridae, Picornaviridae, Secoviridae, Alphalexviridae, Betaflexiviridae, Gammaflexiviridae, Tymoviridae, Bornaviridae, Filoviridae, Paramyoviridae, Rhabdoviridae, Nyamiviridae, Caliciviridae, Flaviviridae, Luteoviridae, Togaviridae, Pneumoviridae, Arenaviridae, Deltavirus, or Orthomyxoviridae virus, but is not limited thereto.

The EPRS protein of the present invention or the fragment thereof may be a conjugate that is bound a drug delivery vehicle. The drug delivery vehicle may be chemically or physically bound to the EPRS protein or the fragment thereof, or bound to the same directly or via a linker. The binding by the linker may be any chemical bond such as a non-covalent chemical bond or a covalent chemical bond, but is not limited thereto.

The linker above may be a peptide linker, a non-peptide linker, and a combination thereof, but is not limited thereto. Although the peptide linker is not particularly limited as long as it shows an activity of the EPRS protein or the fragment thereof which is bound to a drug delivery vehicle, specifically, amino acids such as glycine, alanine, leucine, isoleucine, proline, serine, threonine, asparagine, aspartic acid, cysteine, glutamine, glutamic acid, lysine, arginine, etc. may be used for linking, and more specifically, several amino acids such as valine, leucine, aspartic acid, glycine, alanine, proline, etc. may be used for linking, and even more specifically, in consideration of the ease of genetic manipulation, one to five amino acids such as glycine, valine, leucine, and aspartic acid may be linked and used.

In addition, a non-peptide linker includes a biocompatible polymer in which two or more repeating units are bound, and the repeating units are linked to each other by any covalent bond which is not a peptide bond. The non-peptide linker may be selected from the group consisting of polyethylene glycol, polypropylene glycol, ethylene glycol-propylene glycol copolymer, polyoxyethylated polyol, polyvinyl alcohol, polysaccharide, dextran, polyvinyl ethyl ether, lipid polymer, chitin, hyaluronic acid, or a combination thereof, but is not limited thereto.

As used herein, the term "drug delivery vehicle" refers to a substance that helps to deliver the EPRS protein or the fragment thereof to a site of action, and is not limited to a material that enhances the efficiency of delivery, and may be used for various purposes such as improving the biocompatibility of drug, increasing the half-life of drug, adjusting the release of drug, imaging a drug or etc. The drug delivery vehicle may be one or more selected from the group consisting of a labeling material, a targeting ligand, a cell-penetrating peptide, a polymeric nanoparticle, a viral vector, a virus-like particle, and an inorganic nanoparticle, but is not limited thereto. Meanwhile, the drug refers to a substance having physiological effects on the body, and includes the EPRS protein of the present invention or fragment thereof.

The labeling material refers to a material which images the EPRS protein or fragment thereof, or a material interacting with the EPRS protein or fragment thereof. Specifically, the labeling material may include radioactive isotopes (e.g., $^{32}$P, $^{33}$P, or $^{35}$S), fluorescent labels, chemiluminescent labels, bioluminescent labels, hapten labels (e.g., biotin), and enzyme labels (e.g., streptavidin or avidin). The fluorescent labels may include negatively charged dyes (e.g., dyes of the fluothane family), neutrally charged dyes (e.g., dyes of the rhodamine family), and positively charged dyes (e.g., dyes of the cyanine family). The dyes of the fluothane family, for example, include FAM, HEX, TET, JOE, NAN and ZOE, the dyes of the rhodamine family include Texas Red, ROX, R110, R6G, and TAMRA, and the dyes of the canine family include Cy2, Cy3, Cy5, and Cy7.

The targeting ligand refers to a substance that has affinity for an organ, tissue, cell, or subcellular region at the location in which a substance is to be delivered. The targeting ligand may be used to penetrate a substance to be delivered into a target cell or keep a substance in a target cell, or may be a substance capable of binding to a molecule or a receptor which is highly expressed in a specific organ, tissue, cell, or subcellular region. The targeting ligand may include, but is not limited to, an antibody, a protein, a peptide, a nucleic acid, an aptamer, a sugar, and a small molecule. Specifically, the targeting ligand includes transferrin, folic acid. LyP-1, iRGD, CREKA, NGR, and LABL, but is not limited thereto.

As used herein, the term "cell-penetrating peptide" refers to a short peptide that facilitates cellular intake/uptake of various substances such as nanoparticles, compounds, DNAs, proteins, etc. Specifically. , the cell-penetrating peptide may be Tat, Antennapedia, Transportan, VP22, Hph-1, R11 (SEQ ID NO: 71), R9 (SEQ ID NO: 72), a signal sequence-based peptide, or an amphipathic peptide; but is not limited thereto. The cell-penetrating peptide may be appropriately selected by those skilled in the art, as long as it is capable of facilitating intercellular transport of the EPRS protein of the present invention or the fragment thereof.

The polymeric nanoparticles comprise natural polymers such as albumin, gelatin, alginate, collagen, and chitosan, and synthetic polymers such as polylactic acid (PLA), polyglycolic acid (PGA), and copolymers thereof such as polylactide-co-glycolide (PLGA), polyacrylate, polycaprolactone (PCL), and polyethylene oxide (PEO). The polymeric nanoparticles may also comprise dendrimers, nanogels, liposomes, and lipid nanoparticles.

The viral vector and virus-like particle are designed to mimic the behavior of viruses when infecting cells, meaning that the viral vector retains the gene transfer and expression efficiency, but the virulence of viruses is removed. The virus-like particle (VLP) means that it imitates the structure of actual viruses by containing a viral capsid protein and not completely containing the viral genome.

The inorganic nanoparticles may comprise carbon allotropes such as carbon nanotubes, fullerenes, and quantum dots such as photon dots (e.g., CdSe, CdTe, InP, and InAs), nanoshells, paramagnetic nanoparticles such as iron oxide nanoparticles, and metal nanoparticles such as gold nanoparticles and silver nanoparticles.

An aspect of the present invention may relate to a conjugate comprising an EPRS protein or a fragment thereof along with an inorganic nanoparticle, a polymeric nanoparticle and a labeling material as a drug delivery vehicle.

In an aspect of the present invention, the EPRS protein of the present invention or the fragment thereof may be appropriately modified depending on the kind of drug delivery vehicle to be used. That is, the EPRS protein of the present invention or the fragment thereof is not limited to the amino acid sequence suggested in the present invention, and amino acid sequences may be added/substituted/removed in such a form that is suitably applied to the drug delivery vehicle within a range obvious to those skilled in the art.

For example, the EPRS protein or the fragment thereof may be used after being additionally fused with a cell penetrating peptide in order to increase cell permeability. That is, the EPRS protein or fragment thereof may further comprise a cell-penetrating peptide at the N-terminus, the C-terminus, or both ends thereof. In particular, a linker may be further included between the EPRS protein or fragment thereof and the cell-penetrating peptide, which may be appropriately performed by those skilled in the art.

In a specific embodiment of the present invention, antiviral activity of a fusion peptide (Tat-Epep: SEQ ID NO: 61) obtained by fusing an HIV-1 Tat protein transduction domain (SEQ ID NO: 60) with an EPRS L1 peptide (at positions 168 to 196 in SEQ ID NO: 63) was examined (FIGS. 99 to 109), and as a result, it was confirmed that Tat-Epep shows excellent anti-RNA viral activity in vitro and in vivo by promoting MAVS stability and type I IFN production and significantly decreasing viral titers in virus-infected mouse brain tissues.

In another specific embodiment of the present invention, it was confirmed that a fusion peptide (New Tat-Epep. SEQ ID NO: 64) obtained by fusing the HIV-1 Tat protein transduction domain (SEQ ID NO: 60) with an EPRS L1 peptide fragment (at positions 168 to 186 in SEQ ID NO: 63) significantly decreases viral titers in virus-infected mouse brain tissues and promotes secretion of antiviral cytokines IFN-β and IL-6, as compared with the Tat-Epep (FIGS. 110 to 113).

Further, in order to increase cell permeability, the EPRS protein of the present invention or the fragment thereof may be used together with a reagent known in the art which is able to deliver a protein into a cell or to promote the delivery efficiency. The reagent may be, for example, Chariot (Active motif, Cat. 30025), etc., but is not particularly limited thereto, as long as it is able to deliver the EPRS protein of the present invention or the fragment thereof to cells.

Further, in a specific embodiment of the present invention, as a result of investigating an intracellular delivery effect of an EPRS conjugate in which TAMRA fluorophore, gold nanoparticles, and the fragment of the EPRS protein (an amino acid sequence at positions 166 to 186 in SEQ ID NO: 63) are bound (FIG. 115), the EPRS conjugate was confirmed to be effectively delivered into cells even at low concentrations.

Still another aspect of the present invention provides a polynucleotide encoding the protein or the fragment thereof.

Still another aspect of the present invention provides a vector comprising the polynucleotide.

Still another aspect of the present invention provides a transformant comprising the polynucleotide or the vector.

The EPRS protein or the fragment thereof is the same as described above.

The polynucleotide may be a nucleotide sequence encoding the EPRS protein of the present invention or the fragment thereof, or a nucleotide sequence having at least 80% or more, 90% or more, 95% or more, 97% or more, or 99% or more homology thereto. As long as a polypeptide (i.e., a protein or a fragment thereof) translated therefrom exhibits efficacy corresponding to that of the EPRS protein of the present invention or the fragment thereof, those obtained by addition of a meaningless sequence at the 5'- and/or 3'-terminus of the nucleotide sequence or by deletion, modification, or substitution of a partial sequence may also be included in the scope of the present invention. The polynucleotide may be operably linked to a known promoter sequence to be used in the form of an expression cassette, or the polynucleotide may be used in the form of a vector comprising the same. Preparation of the polynucleotide, expression cassette, or vector may be appropriately performed through a known method by those skilled in the art. The kind of promoter or vector is not particularly limited, and may be appropriately selected by those skilled in the art depending on the purpose. Further, the transformant may be used after being prepared by transforming a host cell with the polynucleotide, expression cassette, or vector. As the transformation method, a known method may also be used without limitation by those skilled in the art. The transformant is an object where the EPRS protein of the present invention or the fragment thereof is intended to be expressed, and the transformant may be a microorganism, a plant, an animal, or an animal excluding a human, but is not limited thereto.

In order to apply/produce the EPRS protein or the fragment thereof for various purposes, those skilled in the art may prepare a vector comprising the polynucleotide encoding the same or a transformant comprising the vector. For example, the polynucleotide or the vector may be directly used in the treatment of a RNA-viral infectious disease, or the transformant which is able to express the EPRS protein or the fragment thereof by comprising the polynucleotide or the vector may be used for the purpose of producing the protein or the fragment thereof or used for the therapeutic purpose, but is not limited thereto.

Another aspect of the present invention provides a composition comprising an EPRS protein or a fragment thereof. The EPRS protein or the fragment thereof is the same as described above.

A composition comprising the EPRS protein of the present invention or the fragment thereof may further comprise an appropriate carrier, excipient, or diluent which is commonly used in the preparation of compositions. A carrier may be a naturally occurring carrier or a non-naturally occurring carrier, but the kind of carrier is not particularly limited, and any carrier may be used as long as it is commonly used in the art.

The composition may be used as a pharmaceutical composition, a quasi-drug composition, a food composition, a cosmetic composition, or a feed composition, but is not limited thereto.

Still another aspect of the present invention provides a pharmaceutical composition for preventing or treating a RNA viral infectious disease, which comprises the composition comprising an EPRS protein or a fragment thereof.

The composition comprising the EPRS protein or fragment thereof is the same as described above.

As used herein, the term "RNA viral infectious disease" refers to all diseases that may occur in a host resulting from infection with RNA viruses. The EPRS protein of the present invention or the fragment thereof is expected to have prophylactic and/or therapeutic effects on the above diseases. For example, the RNA viral infectious disease may be one or more selected from the group consisting of influenza, poliomyelitis anterior acuta, aseptic meningitis, hand-foot-mouth disease, herpangina, acute hemorrhagic conjunctivitis, epidemic pleurodynia, pericarditis, myocarditis, baby white diarrhea, rubella, congenital rubella syndrome, yellow fever, dengue fever, dengue hemorrhagic fever. Japanese encephalitis, Herpes simplex encephalitis, epidemic parotitis, measles, rabies, Marburg disease, Ebola hemorrhagic fever, hemorrhagic fever with renal syndrome, hantavirus pulmonary syndrome (HPS), Congo-Crimean hemorrhagic fever, AIDS (acquired immunodeficiency disease), adult T-cell leukerma, HTLV-1 associated myelopathy, HTLV-1 uveitis, and Lassa fever, but is not limited thereto. All diseases and symptoms caused by RNA viruses are also included in the scope of the present invention.

As used herein, the term "preventing" means all of the actions by which onset of the RNA viral infectious disease is inhibited or delayed by administration of the composition according to the present invention, and the term "treating" means all of the actions by which symptoms of the RNA viral infectious disease have taken a turn for the better or been modified favorably by administration of the composition according to the present invention.

Preventing or treating of the RNA viral infectious disease may be achieved by binding of the EPRS protein of the present invention or the fragment thereof to PCBP2 protein, and furthermore, by activation of MAVS signaling. Therefore, the composition comprising the EPRS protein of the present invention or the fragment thereof may have the above-described anti-RNA viral activity, thereby being effectively used as a composition for preventing or treating RNA viral infectious disease.

The pharmaceutical composition of the present invention may further comprise an appropriate carrier, excipient, or diluent which is commonly used in the preparation of pharmaceutical compositions. A composition comprising a pharmaceutically acceptable carrier may be in a variety of oral or parenteral formulations, and specifically, parenteral formulations, but is not limited thereto. The formulations may be prepared using commonly used diluents or excipients, such as fillers, extenders, binders, wetting agents, disintegrants, surfactants, etc. Solid formulations for oral administration may comprise tablets, pills, powders, granules, capsules, etc. Such solid formulations may be prepared by mixing one or more compounds with at least one excipient, for example, starch, calcium carbonate, sucrose, lactose, gelatin, etc. In addition to simple excipients, lubricants such as magnesium stearate or talc may also be used. Liquid formulations for oral administration may comprise suspensions, oral liquids, emulsions, syrups, etc., and various excipients, for example, humectants, sweeteners, fragrances, preservatives, etc., may be used, in addition to the simple diluents such as water and liquid paraffin commonly used. Formulations for parenteral administration may comprise sterile aqueous solutions, non-aqueous solvents, suspensions, emulsions, lyophilized formulations, suppositories, etc. Examples of the non-aqueous solvents and suspensions may comprise propylene glycol, polyethylene glycol, vegetable oils such as olive oil, an injectable ester such as ethyl oleate, etc. Examples of bases for suppositories may comprise witepsol, macrogol, tween 61, cacao butter, laurin butter, glycerogelatin, etc.

Further, the pharmaceutical composition of the present invention may comprise, but is not limited to, any one formulation selected from the group consisting of a tablet, a pill, a powder, a granule, a capsule, a suspension, an oral liquid, an emulsion, a syrup, a sterilized aqueous solution, a non-aqueous solvent, a suspension, an emulsion, a lyophilized formulation, and a suppository.

The pharmaceutical composition of the present invention may be administered in a pharmaceutically effective amount.

As used herein, the term "administration" means introducing the pharmaceutical composition of the present invention into a subject by any suitable method, and the administration route may comprise administering through various routes comprising oral or parenteral routes as long as the pharmaceutical composition can reach a desired tissue. Specifically, the pharmaceutical composition may be administered via parenteral routes, but is not limited thereto.

The pharmaceutical composition may be appropriately administered to a subject according to a method, an administration route, and an administration dose commonly used in the art, depending on the purpose or necessity. Examples of the administration route may comprise oral, parenteral, subcutaneous, intraperitoneal, intrapulmonary, and intranasal routes, and the parenteral administration may comprise intramuscular, intravenous, intraarterial, intraperitoneal, and subcutaneous administration. Further, appropriate administration dose and administration frequency may be selected according to a method known in the art, and the dose and administration frequency of the pharmaceutical composition of the present invention to be practically administered may be appropriately determined by various factors such as the kind of symptoms to be treated, route of administration, sex, health conditions, diet, an individual's age and weight, and disease severity.

As used herein, the term "pharmaceutically effective amount" refers to an amount sufficient for the inhibition or alleviation of increased vascular permeability at a reasonable benefit/risk ratio applicable to a medical treatment, and the level of the effective dose may be determined based on the factors comprising a subject's kind, severity, age, sex, drug activity, drug sensitivity, administration time, administration route, and excretion rate, and treatment duration, drug(s) to be used simultaneously, and other factors well known in the medical field. The composition of the present invention may be administered alone or in combination with other therapeutic agents, and administered sequentially or simultaneously with existing therapeutic formulation(s). Then, the pharmaceutical composition may be administered in single or multiple doses. Considering all the elements above, it is important to administer a minimum amount, which can obtain maximum effects without causing side effects, and this may be readily determined by one of ordinary skill in the art Still another aspect of the present invention provides a method of preventing or treating a RNA viral infectious disease, comprising administering an EPRS protein, a fragment thereof, or a composition comprising the EPRS protein or fragment thereof to a subject.

The EPRS protein, the fragment thereof, or the composition comprising the EPRS protein or fragment thereof, and the prevention or treatment of a RNA viral infectious disease are the same as described above.

As used herein, the term "subject" refers to all animals comprising humans already having or being at risk of having a RNA viral infectious disease of the present invention. Further, the subject may refer to animals excluding humans, but is not limited thereto. The RNA viral infectious diseases may be prevented or treated by administering the EPRS protein of the present invention, the fragment thereof, or the composition comprising the EPRS protein or fragment thereof to the subject.

Still another aspect of the present invention provides a quasi-drug composition for preventing or improving a RNA viral infectious disease, which comprises a composition comprising an EPRS protein or a fragment thereof.

The composition comprising the EPRS protein or fragment thereof, the RNA viral infectious disease, and the preventing are the same as described above.

As used herein, the term "improving" means all of the actions by which the RNA viral infectious disease have taken a turn for the better or been modified favorably by administration of the composition according to the present invention.

As used herein, the term "quasi-drug" refers to fibers, rubber products, or similar products used for the purpose of medical care, alleviation, treatment, or prevention of disease in humans or animals: non-appliance, non-machinery or similar products which have insignificant influences on or do not directly act upon human bodies: or preparations used for sterilization, insecticide and purposes similar thereto in order to prevent infection, and the quasi-drug may refer to products used for the purposes of diagnosis, medical care, alleviation, treatment, or prevention of diseases of humans or animals, excluding appliances, machinery and equipment; or products, other than appliances, machinery, or equipment, used for the purpose of exerting pharmacological effects upon the structure or functions of humans or animals. The quasi-drug may be specifically skin external agents and personal hygiene products, but is not limited thereto.

When the composition comprising the EPRS protein of the present invention or fragment thereof, is added to the quasi-drug composition in order to prevent or improve the RNA viral infectious disease, the composition comprising the EPRS protein or fragment thereof may be added as it is or used in combination with other quasi-drug components, and may be properly used according to a common method. The mixing amount of the active ingredient may be appropriately determined, depending on the purpose of use.

The skin external agent may be prepared, but is not particularly limited to, for example, as an ointment, a lotion, a spray, a patch, a cream, a powder, a suspension, a gel agent, or a form of gel. The personal hygiene product may be, but is not particularly limited to, specifically a soap, a cosmetic product, a wet tissue, a tissue, a shampoo, a skin cream, a facial cream, a toothpaste, a lip stick, a sunscreen lotion, or a wash gel. Further, other examples of the quasi-drug composition of the present invention may comprise a disinfection cleaner, a shower foam, a wet tissue, a detergent soap, a hand wash, and an ointment.

Still another aspect of the present invention provides a food composition for preventing or improving the RNA viral infectious disease, which comprises a composition comprising an EPRS protein or a fragment thereof.

The composition comprising the EPRS protein or fragment thereof, the RNA viral infectious disease, the preventing, and the improving are the same as described above.

As used herein, the term "food" may comprise meats, sausages, bread, chocolate, candies, snack, confectionery, pizza, ramen, other noodles, gums, dairy products comprising ice cream, various soups, beverages, teas, drinks, alcoholic beverages, multivitamin complex, health functional foods, health foods, etc., and may comprise all the foods that are considered within conventional meaning.

The term "health functional food" is the same term as food for special health use (FoSHU), and refers to a food having high medicinal and medical effects, which is processed to effectively exert a body-regulating function as well as to supply nutrients. Here, the term "functional" means that it is taken for the purpose of controlling nutrients with respect to structures and functions of the human body or of obtaining effects beneficial for health care, such as physiological effects. The health food refers to a food having an effect of actively maintaining or promoting health, compared to a general food, and a health supplement food refers to a food aimed at health supplement. In some cases, the health functional foods, health foods, and health supplement foods can be used interchangeably.

Specifically, the health functional food is a food prepared by adding the anti-RNA virus composition of the present invention to a food material such as beverages, teas, flavors, gums, confectionery, etc., or prepared as a capsule, powder, suspension, etc., and the health functional food means a food that brings out a particular effect on health when taken. Unlike general drugs, the food composition comprises a food as a raw material, and therefore, it has advantages of being free from side effects that may occur when taken for a long period of time.

The food of the present invention may be prepared by a method commonly used in the art, and may be prepared by adding raw materials and ingredients which are commonly added in the art. In addition, the food composition may be prepared as various types of formulations without limitation as long as it is acceptable as a food formulation.

The food composition may further comprise a physiologically acceptable carrier, and the kind of carrier is not particularly limited, and any carrier may be used as long as it is commonly used in the art.

Further, the food composition may further comprise an additional ingredient capable of improving smell, taste, appearance, etc which is commonly used in the food composition. For example, the food composition may comprise vitamin A, C, D, E, B1, B2, B6, or B12, niacin, biotin, folate, panthotenic acid, etc. Further, the food composition may comprise minerals such as zinc (Zn), iron (Fe), calcium (Ca), chromium (Cr), magnesium (Mg), manganese (Mn), copper (Cu) chromium (Cr), etc.; and amino acids such as lysine, tryptophan, cysteine, valine, etc.

Further, the food composition may comprise food additives such as preservatives (potassium sorbate, sodium benzoate, salicylic acid, sodium dehydroacetate, etc), disinfectants (bleaching powder, higher bleaching powder, sodium hypochlorite, etc.), antioxidants (butylhydroxyanisole (BHA), butylhydroxytoluene (BHT), etc.), coloring agents (tar dye, etc.), color fixing agents (sodium nitrite, etc.), bleaching agents (sodium sulfite), seasonings (monosodium glutamate (MSG), etc.), sweeteners (dulcin, cyclemate, saccharin, sodium, etc.), flavors (vanillin, lactones, etc.), swelling agents (alum, potassium D-bitartrate, etc.), fortifiers, emulsifiers, thickeners (adhesive pastes), film-forming agents, gum base agents, antifoaming agents, solvents, improvers, etc. The additives may be selected and used in an appropriate amount according to the food types.

Still another aspect provides a cosmetic composition for preventing or improving the RNA viral infectious disease, which comprises a composition comprising an EPRS protein or a fragment thereof.

The composition comprising the EPRS protein or fragment thereof, the RNA viral infectious disease, the prevention, and the improvement are the same as described above.

The formulation of the cosmetic composition may be a solution, an external ointment, a cream, a foam, a nutritional lotion, a softening lotion, a perfume, a pack, a softening water, a milky lotion, a makeup base, an essence, a soap, a liquid cleanser, a bath preparation, a sunscreen cream, a sun oil, a suspension, an emulsion, a paste, a gel, a lotion, a powder, a soap, a surfactant-containing cleanser, an oil, a powder foundation, an emulsion foundation, a wax foundation, a patch, or a spray, but is not limited thereto.

The cosmetic composition of the present invention may further comprise one or more cosmetically acceptable carriers which are blended in general skin cosmetics Common components, for example, oil, water, a surfactant, a humectant, a lower alcohol, a thickener, a chelate agent, an inorganic salt, a pigment, an antioxidant, a sterilizer, a preservative, a perfume, etc. may be blended, but is not limited thereto.

The cosmetically acceptable carrier may vary depending on the formulation of the cosmetic composition.

When the formulation is an ointment, a paste, a cream, or a gel, as a carrier ingredient, animal oil, vegetable oil, wax, paraffin, starch, tragacanth, a cellulose derivative, polyethylene glycol, silicon, bentonite, silica, talc, or zinc oxide may be used, but is not limited thereto. These may be used alone or in a mixture of two or more thereof.

When the formulation is a powder or a spray, as a carrier ingredient, lactose, talc, silica, aluminum hydroxide, calcium silicate, polyamide powder, etc. may be used. Particularly, when the formulation is a spray, it may additionally comprise propellants, such as chlorofluorohydrocarbons, propane/butane, or dimethyl ether, but is not limited thereto. These may be used alone or in a mixture of two or more thereof.

When the formulation is a solution or an emulsion, as a carrier ingredient, a solvent, a solubilizer, a demulsifying agent, etc. may be used. For example, water, ethanol, isopropanol, ethyl carbonate, ethyl acetate, benzyl alcohol, benzyl benzoate, propylene glycol. 1,3-butyl glycol oil, etc. may be used, and in particular, cottonseed oil, peanut oil, corn germ oil, olive oil, castor oil, sesame oil, glycerol aliphatic esters, polyethylene glycol, or sorbitan fatty acid esters may be used, but is not limited thereto. These may be used alone or in a mixture of two or more thereof.

When the formulation is a suspension, as a carrier ingredient, liquid diluents such as water, ethanol, or propylene glycol, suspending agents such as ethoxylated isosteatryl alcohol, polyoxyethylene sorbitol esters, and polyoxyethylene sorbitan esters, microcrystalline cellulose, aluminum meta-hydroxide, bentonite, agar, tragacanth, etc. may be used, but is not limited thereto. These may be used alone or in a mixture of two or more thereof.

When the formulation of the present invention is a soap, as a carrier ingredient, alkali metal salts of fatty acids, hemiester salts of fatty acids, fatty acid protein hydrolysates, isethionates, lanolin derivatives, aliphatic alcohols, vegetable oil, glycerol, sugars, etc. may be used, but is not limited thereto. These may be used alone or in a mixture of two or more thereof.

Still another aspect of the present invention provides a feed composition for preventing or improving the RNA viral infectious disease, which comprises a composition comprising an EPRS protein or a fragment thereof.

The composition comprising the EPRS protein or fragment thereof, the RNA viral infectious disease, the prevention, and the improvement are the same as described above.

As used herein, the "feed" refers to any natural or artificial diet, meal, etc., or components of such meals intended or suitable for being eaten, taken in, or digested by animals. The feed which comprises the composition comprising the EPRS protein or fragment thereof as an active ingredient may be prepared as various types of feeds known in the art, and may preferably comprise concentrated feeds, bulky feeds, and/or specialized feeds.

Still another aspect of the present invention provides a method of preventing or inhibiting MAVS protein degradation, comprising administering an EPRS protein, a fragment thereof, and a composition comprising the EPRS protein or fragment thereof.

The EPRS protein, the fragment thereof, the composition comprising the EPRS protein or fragment thereof, and the administration are the same as described above.

Still another aspect of the present invention provides a method of inhibiting the binding of PCBP2 to MAVS, comprising administering an EPRS protein, a fragment thereof, or a composition comprising the EPRS protein or fragment thereof to a subject.

The EPRS protein, the fragment thereof, the composition comprising the EPRS protein or fragment thereof, the subject, and the administration are the same as described above.

Hereinafter, the present invention will be described in more detail with reference to Examples. However, these Examples are for Illustrative purposes only, and the scope of the present invention is not intended to be limited by these Examples.

Example 1: Cell Culture and Transfection

HEK293T, HeLa. MDCK, Vero, and RAW264.7 cells were cultured in DMEM containing 10% FBS (Fetal bovine serum, Gibco-BRL) and 1% penicillin-streptomycin (Gibco-BRL). U937 cells were grown in RPMI 1640 medium (Gibco-BRL) containing 10% FBS and 1% penicillin-streptomycin. All the cells were obtained from ATCC (American Type Culture Collection).

Bone marrow derived macrophages (BMDMs) were isolated from 5- to 6-week-old mice, and red blood cells were lysed with an ammonium-chloride-potassium (ACK) lysing buffer (Gibco-BRL). BMDMs were then cultured in DMEM containing 10% FBS, 10% L929 cell-CM (conditioned medium), and GM-CSF (R&D Systems). The medium was replaced with fresh complete medium every 2 days. Cells were used for the experiments on day 7.

Stable RAW264.7 cells in which EPRS was knocked down were established by treatment with shRNA (kindly provided by Dr. Jae U. Jung, University of Southern California) and selection with 2 μg-mL of puromycin for at least 2 weeks.

RAW264.7 cells stably expressing pIRES or pIRES-EPRS-FLAG were established by transfection with the corresponding DNA constructs and maintained in DMEM containing 1 μg/mL of puromycin.

HEK293T cells were transfected with DNA plasmid constructs using an X-tremeGENE HP DNA transfection reagent (Roche). U937, RAW264.7, and BMDM cells were transfected with nucleotransfector (Lonza, Cologne AG, Germany) and immediately cultured in Opti-MEM medium (Gibco-BRL) for 6 h, followed by culture in a complete medium containing 10% FBS for 24 hours.

Example 2: Mice and Viral Infection

C57BL/6EPRS$^{tm1b}$ heterozygous knockout mice were obtained from the Toronto Center for Phenogenomics (Ontario, Canada) and maintained in a specific pathogen-free facility on a 12 h light/dark cycle at 22±2° C. with free access to food and water. Offspring were genotyped by PCR using the following primers:

A:

5'-TACTGTGCTGAATGAAAAGTGCC-3', (SEQ ID NO: 1)

B:

5'-GGTAGAAGTGCTAAGTAGGATGAGG-3', (SEQ ID NO: 2)
(specific to the 218 bp WT band)

C:

5'-CCATTACCAGTTGGTCTGGTGTC-3', (SEQ ID NO: 3)
and

D:

5'-TGCCTGTGACCACCAATAAGAAAGCC-3' (SEQ ID NO: 4)
(specific to the 462 bp mutant band).

All mice were euthanized by $CO_2$ asphyxiation. All animal experiments were approved by the Institutional Animal Use and Care Committee of the Korea Research Institute of Bioscience and Biotechnology, and performed in accordance with the Guide for the Care and Use of Laboratory Animals (published by the US National Institutes of Health).

For the viral infection experiments, 6- to 7-week-old mice were infected with VSV-Indiana ($2 \times 10^8$ pfu/mouse) or VSV-GFP ($2 \times 10^8$ pfu/mouse) via intravenous injection into the tail vein.

Example 3: Reagents and Antibodies

The following primary antibodies were used in immunoblotting and immunofluorescence experiments: anti-EPRS (ab31531), anti-MRS (ab50793), anti-KRS (ab186196), anti-PCBP2 (ab110200), anti-Ceruloplasmin (ab135649), and anti-VSV-G (ab1874) (Abcam), anti-MAVS (human-specific: 3993, rodent-specific: 4983), anti-L13a (2765), anti-IRF3 (4302), anti-phospho-IRF3 (4947), anti-STAT1 (9172), anti-phospho-STAT1 (7649), and anti-Actin-HRP (12620) (Cell Signaling Technology); anti-NSAP1 (AV40641), anti-GAPDH (G9545), and anti-FLAG (F3165) (Sigma), anti-Ub (sc-8017), anti-GFP (sc-9996), and anti-GST (sc-459) (Santa Cruz Biotechnology): anti-AIMP3 (NMS-01-0002, Neomics, Seoul, Korea); anti-V5-HRP (46-0708, Invitrogen): anti-K48-linked polyubiquitin chains (05-1307. Millipore): anti-Strep-HRP (2-1509-001, IBA, Germany).

An affinity-purified rabbit polyclonal phosphate-specific antibody against Ser990 was produced using a $^{983}$DGQRKDP(p)SKNQGGG$^{996}$ peptide (SEQ ID NO: 5) (AbClon, Seoul, Korea). Phosphate-specific Ser886 and Ser999 antibodies were provided by Dr. Paul L. Fox (Lerner Research Institute, Cleveland Clinic, CLV, USA). Goat anti-mouse (7076) or anti-rabbit (7074) IgG-HRP (Cell Signaling Technology) was used as a secondary antibody in the immunoblotting. Alexa488-conjugated anti-mouse IgG (A11059. Invitrogen) and Alexa594-conjugated anti-rabbit IgG (A11037. Invitrogen) were used as a secondary antibody in the immunofluorescence experiments. Other reagents and materials including MG-132 (Sigma), puromycin (Gibco-BRL), poly(I:C) (InvivoGen), IFN-γ (R&D Systems), digitonin (Sigma), protein A/G PLUS-agarose (sc-2003, Santa Cruz Biotechnology), Glutathione Sepharose 4 Fast Flow (17-5132-01, GE Healthcare), anti-FLAG M2 affinity gel (A2220, Sigma), Strep-Tactin Sepharose (2-1201-002, IBA), Ni-NTA agarose (30230, Qiagen), GFP-trap (gta-20, ChromoTek, Germany), and Superdex 200 10/3100 GL column (GE Healthcare) were used.

Example 4: Plasmid Construction

EPRS constructs were generated by conjugation of a FLAG, Strep, His, or GFP tag. Specifically, EPRS fragments harboring each domain was amplified by PCR, and subcloned into GFP-, Strep-. His- or FLAG-tag-containing vectors. Phosphomimetic mutants of EPRS (S886D, S990D, S999D, S886D/S990D, and S886D/S999D) were prepared by PCR using a QuikChange site-directed mutagenesis kit (Stratagene, Amsterdam, Netherlands) PCR primers used for site-directed mutagenesis are listed in the following Table 1.

TABLE 1

| Gene | Forward | Reverse |
|---|---|---|
| qPCR primer | | |
| hEPRS | CTTCTCAAGGGGAAG (SEQ ID NO: 6) | CTGCTTTTCAGATTT (SEQ ID NO: 7) |
| mEPRS | AAGCGGAAAAGGCTCCTAAG (SEQ ID NO: 8) | CCCAGTCTTTTCTTTATACTCAGCTT (SEQ ID NO: 9) |
| IFN-α | CTTGAAGGACAGACATGACTTTGGA (SEQ ID NO: 10) | GGATGGTTTCAGCCTTTTGGA (SEQ ID NO: 11) |
| IFN-β | TCCAAGAAAGGACGAACATTCG (SEQ ID NO: 12) | TGCGGACATCTCCCAACGTCA (SEQ ID NO: 13) |
| ADAR1 | CCAAAGACACTTCCTCTC (SEQ ID NO: 14) | CAGTGTGGTGGTTGTACT (SEQ ID NO: 15) |
| MX1 | ACAAGCACAGGAAACCGTATCAG (SEQ ID NO: 16) | AGGCAGTTTGGACCATCTTAGTG (SEQ ID NO: 17) |
| OAS1 | GAGGCGGTTGGCTGAAGAGG (SEQ ID NO: 18) | GAGGAAGGCTGGCTGTGATTGG (SEQ ID NO: 19) |
| OAS1β | TTGATGTGCTGCCAGCCTAT (SEQ ID NO: 20) | TGAGGCGCTTCAGCTTGGTT (SEQ ID NO: 21) |
| PKR | GCCAGATGCACGGAGTAGCC (SEQ ID NO: 22) | GAAAACTTGGCCAAATCCACC (SEQ ID NO: 23) |

TABLE 1-continued

| Gene | Forward | Reverse |
|---|---|---|
| PML | CCTGCGCTGACTGACATCTACT (SEQ ID NO: 24) | TGCAACACAGAGGCTGGC (SEQ ID NO: 25) |
| P56 | CCCACGCTATACCATCTACC (SEQ ID NO: 26) | CTGAGGCTGCTGCTATCC (SEQ ID NO: 27) |
| ISG15 | CAATGGCCTGGGACCTAAA (SEQ ID NO: 28) | CTTCTTCAGTTCTGACACCGTCAT (SEQ ID NO: 29) |
| ISG20 | AGAGATCACGGACTACAGAA (SEQ ID NO: 30) | TCTGTGGACGTGTCATAGAT (SEQ ID NO: 31) |
| ISG56 | AGAGAACAGCTACCACCTTT (SEQ ID NO: 32) | TGGACCTGCTCTGAGATTCT (SEQ ID NO: 33) |
| GAPDH | TGACCACAGTCCATGCCAT (SEQ ID NO: 34) | GACGGACACATTGGGGGTAG (SEQ ID NO: 35) |
| VSV-G | CAAGTCAAAATGCCCAAGAGTCACA (SEQ ID NO: 36) | TTTCCTTGCATTGTTCTACAGATGG (SEQ ID NO: 37) |
| PCR primers for site-directed mutagenesis | | |
| EPRS S886D | CCCCCATTATCTCAAAGTTCGGATTCAG ACCCAACCAGAAATT (SEQ ID NO: 38) | AATTTCTGGTTGGGTCTGAATCCGAACT TTGAGATAATGGGGG (SEQ ID NO: 39) |
| EPRS S990D | CACACAAAGGAAAGACCCTGATAAAA ACCAAGGAGGTGGG (SEQ ID NO: 40) | CCCACCTCCTTGGTTTTTATCAGGGTCT TTCCTTTGTGTG (SEQ ID NO: 41) |
| EPRS S999D | TCTAAAAACCAAGGAGGTGGGCTCTCA GATAGTGGAGCAGGAGA (SEQ ID NO: 42) | TCTCCTGCTCCACTATCTGAGAGCCCAC CTCCTTGGTTTTTAGA (SEQ ID NO: 43) |
| EPRS S990A | GCCAAAGGAAAGACCCTGCTAAAAAC CAAGGAGGT (SEQ ID NO: 44) | ACCTCCTTGGTTTTTAGCAGGGTCTTTC CTTTGGC (SEQ ID NO: 45) |
| EPRS R201L | GAGATGGGAAAGGTTACCGTCTTATTTC CTCCAGAGGCCAGTGG (SEQ ID NO: 46) | CCACTGGCCTCTGGAGGAAATAAGACG GTAACCTTTCCCATCTC (SEQ ID NO: 47) |
| EPRS R395L | GAAGGTGTTACACATGCCCTGTTAACA GAATACCATGACAG (SEQ ID NO: 48) | CTGTCATGGTATTCTGTTGTTAACAGGG CATGTGTAACACCTTC (SEQ ID NO: 49) |
| EPRS S434A/ K435L | CTCAACAACACAGTGCTAGCGCTGAGA AAACTCACATGGTTTG (SEQ ID NO: 50) | CAAACCATGTGAGTTTTCTCAGCGCTA GCACTGTGTTGTTGAG (SEQ ID NO: 51) |
| EPRS R1152L | GTGGTGCAATGTGGTGCTTTGGGAATTC AAGCATC (SEQ ID NO: 52) | GATGCTTGAATTCCCAAAGCACCACATT GCACCAC (SEQ ID NO: 53) |
| siRNA sequence | | |
| hEPRS | CUAAUUCCUCAGCAAGUAU (SEQ ID NO: 54) | |
| mEPRS | CAAAGUCAUCAUCAAACAC (SEQ ID NO: 55) | |
| mMAVS 1 | UUGCUGAGGACAAGACCUAUA (SEQ ID NO: 56) | |
| mMAVS 2 | CAGAGGAGAAUGAGUAUUC (SEQ ID NO: 57) | |
| sgRNA sequence | | |
| sgEPRS 1 | GAATTCTATACTTCGCTACTTGG (SEQ ID NO: 58) | |
| sgEPRS 2 | GCTAGAGTTGCAACTACAGCTGG (SEQ ID NO: 59) | |

FLAG-, Strep-, His-, or GST-tagged full-length and truncated PCBP2 were also prepared. MAVS was cloned into FLAG-, GST- or Strep-tag containing vectors. These vectors used in luciferase reporter analysis were provided by Dr. Jae U. Jung (University of Southern California).

Example 5: RNA-Seq Analysis

Primary normal human bronchial epithelial (NHBE) cells were purchased from ScienCell Research Laboratories, and differentiated as a method previously known. Monolayers of NHBE cells were infected with A/PR/8/34 influenza virus (MOI=1) for 8 hours or 24 hours. Total RNA was isolated from the infected cells using an RNeasy RNA extraction Mini-Kit (Qiagen) and the quality of the isolated RNA was confirmed by agarose gel electrophoresis.

The sequencing library was prepared using a TruSeq RNA sample preparation kit v2 (Illumina). Specifically. mRNA derived from total RNA using poly-T oligo-attached magnetic beads was fragmented and converted into cDNA.

Adapters were ligated to the cDNA, which were amplified by PCR. Paired-end sequencing (101×2) was performed using a Hiseq-2000 (Illumina). Each condition was sequenced in duplicate. Reference genome sequence data from *Homo sapiens* were obtained from the University of California Santa Cruz Genome Browser Gateway (assembly ID: hgl9). The reference genome index was built using SAMtools (v. 0.1.19) and Bowtie2-build component of Bowtie2 (v. 2.1.0). Reads were mapped to the reference genome using Tophat2 (v. 2.0). The number of rpkm (reads per kilobase per million mapped reads) for each gene of 46.895 RefSeq (UCSC hgl9) gene models was calculated using Cufflinks (v. 2.2.1). Heat maps were constructed using Mev (v. 4.9.0). Statistical analyses and graph construction were performed using R (v. 3.1.0) and PYTHON (v. 2.7.6). The RNA-Seq data described in the present invention have been deposited in NCBI's GEO (Gene Expression Omnibus) under accession code GSE75699.

Example 6: Luciferase Assay

HEK293T cells were transfected with a mixture containing a luciferase reporter plasmid a *renilla* luciferase internal control vector (phRL-TK, Promega), and each of the plasmids. The reporter gene assay was performed at 24 hours after transfection using a luminometer (Promega) and a dual-luciferase reporter assay system (Promega). Data are expressed in terms of relative firefly luciferase activity normalized against *renilla* luciferase activity. Promoter activity in cells expressing only reporter and *renilla* plasmids was measured as a control (Con).

Example 7: RNA Interference

Cells were transfected with duplex siRNA using a TransIT-TKO transfection reagent (Mirus) according to the manufacturer's protocol. The sequence of the EPRS-specific siRNA is provided in Table 1. A non-targeting siRNA was used as a control Cells were incubated with siRNA or control for 36 hours to 48 hours before exposure to viruses.

Example 8: Virus Replication Assay

Cells were infected with virus in a medium containing 1% FBS for 2 hours. Excess virus was removed by replacing the medium with a complete medium. Viral titers were determined in MDCK cells (PR8-GFP) or Vero cells (VSV-GFP or HSV-GFP) using a standard plaque assay. Homogenates of freeze-thawed tissue extracts were used for plaque counting when titrating viruses present in mouse tissues. The replication of GFP-tagged virus was measured using a fluorescence module of GloMax® Multi-Microplate Multimode Reader (Promega). Images were acquired using a Nikon eclipse Ti microscope fitted with a 20×1.4 NA Plan-Apochromat objective lens.

Example 9: ELISA

Cytokine concentrations were measured by ELISA of infected cell culture supernatants or mouse serum. The following ELISA kits were used according to the manufacturer's instructions, mouse or human IL-6 (BD Biosciences), IFN-α and IFN-β(PBL interferon source), and IFN-γ (KOMA, Korea).

Example 10: Quantitative Real-Time PCR

Total RNA was extracted from cells and murine tissues using an RNeasy RNA extraction Mini-Kit (Qiagen). cDNA was synthesized using an Enzynomix kit (Enzynomix) and quantitative PCR was performed using gene-specific primer sets (Bioneer, Daejeon, Korea) and SYBR Green PCR Master Mix (Roche). Real-time PCR was performed using a Rotor-Gene Q instrument (Qiagen) according to the manufacturer's instructions. Data were normalized against gapdh expression. Relative expression was calculated using a delta-delta CT method. The sequences of the primers used are listed in Table 1.

Example 11: Immunoblotting Analysis and Immunoprecipitation Analysis

For immunoblotting analysis, cells were lysed with RIPA buffer (20 mM Tris-HCl, pH 7.4, 150 mM NaCl, 1% NP-40, and 1 mM EDTA) containing a protease inhibitor cocktail and a phosphatase inhibitor cocktail (Roche). Whole cell lysates (50 μg to 100 μg) were subjected to SDS-PAGE, followed by immunoblotting with respective antibodies.

To detect phosphorylated proteins, cell lysates were prepared in a phosphosafe extraction buffer (Millipore) containing protease inhibitor cocktail at 4° C.

For immunoprecipitation, cell lysates were pre-cleared by incubation with protein A beads for 1 hour at 4° C. The pre-cleared cell lysates were incubated overnight at 4° C. with the respective antibodies, followed by incubation with 30 μL of protein A/G PLUS-agarose beads for 3 to 4 hours at 4° C. The immunoprecipitates were then collected and washed five times with a lysis buffer before immunoblotting analysis.

Example 12: Protein Purification and Size-Exclusion Chromatography

The plasmids expressing hexahistidine (His)-tagged EPRS (aa 1-732, aa 1-196, and aa 1-168). His-tagged PCBP2 (aa 11-82 and aa 168-279), GST-fused PCBP2 (aa 11-82), or GST-fused MAVS (aa 460-540) protein were transformed into *Escherichia coli* BL21-CodonPlus (DE3)-RIPL cells, and expression was induced by treatment with 0.5 mM IPTG at 18° C. for 18 hours. The cells were suspended in Buffer A (50 mM Tris-HCl, pH 7.5, and 150 mM NaCl) and lysed by sonication on ice. Then, cell lysates were centrifuged at 25.000 g at 4° C. for 1 hour. The supernatants containing His-tagged EPRS domains or PCBP2 domains were loaded onto a Ni-NTA agarose column, washed with Buffer A, and eluted with 250 mM imidazole. Supernatants containing GST-fused PCBP2 or MAVS domains were loaded onto a Glutathione Sepharose 4B column, washed with Buffer A, and eluted with 10 mM reduced glutathione. The purified proteins were then dialyzed against Buffer A and stored at −80° C. until use. Purified EPRS (aa 1-732) was examined by size-exclusion chromatography using a Superdex 200 10/300 GL column at 4° C. Alcohol dehydrogenase (150 kDa) and albumin (66 kDa) were used as molecular weight standards. All eluted proteins were analyzed by SDS-PAGE, followed by staining with Coomassie Brilliant Blue.

Example 13: In Vitro Pull-Down Analysis

Purified His-tagged EPRS domains (10 μM) and GST-fused PCBP2 domain (20 μM) were mixed in a binding buffer (50 mM Tris-HCl. pH 7.5, and 300 mM NaCl). In addition, purified GST-fused MAVS (10 μM) was mixed with the His-tagged PCBP2 domains (5 μM) in the binding buffer. These protein mixtures were then incubated with 50

µL of Ni-NTA agarose beads for 1 hour at 4° C. After washing with wash buffer (50 mM Tris-HCl, pH 7.5, 300 mM NaCl, and 10 mM imidazole), the bound proteins were eluted with an elution buffer (50 mM Tris-HCl, pH 7.5, 300 mM NaCl, and 250 mM imidazole). Samples were loaded onto 4-12% SDS-PAGE gels and protein bands were visualized by Coomassie Blue staining.

Example 14: Histological Analysis

Brain samples were fixed in 4% paraformaldehyde, embedded in paraffin, and cut into 4 µm-thick sections. The sections were then deparaffinized with xylene and stained with H&E.

To detect VSV, brain sections were deparaffinized with xylene and subjected to antigen retrieval by microwaving in citrate buffer (pH 6.5). After staining with a VSV-G antibody (rabbit, 1:200), the sections were incubated with Alexa488-conjugated anti-rabbit IgG (1:250), followed by DAPI staining.

Fluorescence images were captured with a Nikon laser scanning confocal microscope (C2plus, Tokyo. Japan) and processed using NIS-Elements software (Nikon).

Example 15: Confocal Microscopy

HeLa cells were seeded into 8-well plates (Labtek). After virus infection, the infected cells were fixed in 4% paraformaldehyde at room temperature for 20 minutes. To obtain a clear image of the MSC complex, cells were incubated with 25 µg/mL of digitonin on ice for 10 minutes. After permeabilization with 100% methanol for 20 minutes at −20° C., cells were blocked with PBS containing 2% BSA at room temperature for 1 hour. Cells were then washed three times with PBS-T (PBS containing 0.05% Tween-20) and incubated with the appropriate primary antibodies overnight at 4° C. After washing a further three times, cells were incubated for 1 hour at room temperature with the appropriate secondary antibody. Cells were then stained with DAPI at room temperature for another 10 minutes, washed three times with PBS-T, and mounted in a mounting solution. Images were acquired under a Nikon laser scanning confocal microscope (C2plus) and analyzed using NIS-Elements software. The co-localization index based on the Pearson's correlation coefficient was calculated using software tools.

Example 16: Mass Spectrometry to Identify EPRS Phosphorylation Sites and Interactomes HEK293T cells were transfected with Strep-EPRS plasmid construct for 24 hours, followed by infection with PR8-GFP (MOI=5) for 6 hours. Infected cells were harvested in a lysis buffer (20 mM Tris-HCl, pH 8.0, 150 mM NaCl, 0.5% NP-40, and 1 mM EDTA) containing protease inhibitor and phosphatase inhibitor cocktails (Roche), and incubated with Strep-Tactin Superflow high capacity resin (IBA) overnight at 4° C. The resin was washed five times with the lysis buffer, and bound proteins were eluted with an elution buffer (100 mM Tris-HCl, pH 8.0, 150 mM NaCl, 1 mM EDTA, and 2.5 mM desthiobiotin). The final eluted fractions were concentrated in Amicon Ultra-4 (10K MWCO) centrifugation devices (Millipore). The samples were then analyzed by SDS-PAGE and silver stained. Stained protein bands were cut out and subjected to in-gel tryptic digestion. Tryptic peptides were recovered and injected into a reversed-phase Magic 18aq (5 µm, 200 Å, Michrom BioResources) column (15 cm 75 µm, packed in-house) coupled to an Eksigent MDLC system. The peptides were eluted at a flow rate of 300 nL/min with a 40 min linear gradient of acidified water (0.1% formic acid) containing 5-40%, acetonitrile. The HPLC system was coupled to an LTQ XL-Orbitrap mass spectrometer (Thermo Scientific).

Survey full-scan MS spectra (300-2,000 m/z) were acquired, with a resolution of 100,000 for precursor selection and peptide charge state determination. The source of ionization parameters were as follows: spray voltage, 1.9 kV, capillary temperature, 250° C.

The MS/MS spectra for the most intense ions with a charge state≥2 from the MSI scan were acquired using the following options: isolation width, 2.0 m/z, normalized collision energy, 35%; and dynamic exclusion duration, 30 seconds. Raw data were searched using the SEQUEST algorithm in Proteome Discoverer 1.4 (Thermo Scientific) and with the MASCOT search engine (v. 2.3.01; Matrix Science). The human Uniprot database (released in 2013.07) was searched using the following parameters' full tryptic peptide cleavage specificity, two missed cleavages, fixed modification of carbamidomethyl cysteine (±57.021 Da), variable modifications of oxidized methionine (+15.995 Da), and phosphorylated serine, threonine, and tyrosine (+79.9799 Da).

Example 17: In Vivo and In Vitro Ubiquitination Assay

HEK293T cells were transfected with different combinations of MAVS-FLAG, ITCH-V5, GST-PCBP2, and Strep-EPRS plasmids. After 24 hours, the cells were treated with 10 µM MG-132 for 6 hours before lysis with RIPA buffer and immunoprecipitation with anti-FLAG affinity gel at 4° C. for 6 hours. To detect endogenous MAVS ubiquitination, cell lysates were incubated overnight with an anti-MAVS antibody, followed by incubation with protein A/G PLUS-agarose beads at 4° C. for 3 hours. The immune complexes were washed five times with lysis buffer and boiled in an SDS sample buffer for 10 minutes. Ubiquitination was analyzed using anti-Ub or anti-K48 antibody. For the in vitro ubiquitination assay, Strep-MAVS. Strep-PCBP2, and Strep-EPRS proteins were precipitated from the lysates of HEK293T cells transfected with each of the plasmids Itch-V5 protein was prepared by incubating lysates with an anti-VS antibody, followed by incubation with protein A/G PLUS-agarose beads. The purified proteins were incubated at 37° C. for 1 hour with ubiquitin, E1 and E2 from UbcH5b (Boston Biochem) in a reaction buffer containing $Mg^{2+}$-ATP. The reaction was terminated by boiling, followed by the addition of SDS sample buffer containing 1 mM DTT for 10 minutes. Ubiquitination was detected with an anti-Ub antibody.

Example 18: Peptide Design and Synthesis

EPRS L1 (aa 168-196) was fused with cell-penetrating HIV-1 TAT peptide (aa 47-57, YGRKKRRQRRR; SEQ ID NO: 60). The fused peptides (Tat-Epep) were then synthesized and purified to ≥93% by reverse-phase HPLC (Ab-Clon) The Tat-Epep sequence is (SEQ ID NO: 61)
YGRKKRRQRRR-GG-DVSTTKARVAPEKKQDVGKFVELPGAEMG.

TAT harboring the YGRKKRRQRRR sequence (SEQ ID NO: 60) was used as a control peptide. Lyophilized peptides were stored in desiccant at −80° C., and dissolved in PBS before use.

Example 19: Cytotoxicity Assay

HEK293T or RAW264.7 cells were seeded in 96-well plates (10,000 per well) before treatment with Tat-Epep (20-200 μM) for 0-24 hours. Cytotoxicity was determined in a colorimetric assay using MTS [3-(4,5-dimethylthiazole-2-yl)-5-(carboxymethoxyphenyl)-2-(4-sulfophenyl)-2H-tetrazolium salt] (Promega) 20 μL of MTS was added to each well at 37° C. for 1 hour. Optical density at 490 nm was recorded using an automated microplate reader (BioTek). Background absorbance at 630 nm was subtracted from each sample reading.

Example 20: Animal Experiment Using Designed Peptide

C57BL/6 mice (female, 7-week-old) were purchased from Koatech (Pyeongtaek, Korea), and infected by intravenous injection of VSV Indiana ($2\times10^8$ pfu/mouse) 24 hours later, Tat-Epep (2.5 mg/kg [0.53 μM/kg] or 5 mg/kg 11.05 μM/kg]) was intraperitoneally administered to the mice daily for 3 days. A Tat PTD peptide (1.65 mg/kg [1.05 μM/kg]) was used as a control. At day 4, brain tissues were harvested from the mice. The harvested samples were immediately homogenized using a TissueLyser (Qiagen), and viral titers were determined by the above-described method.

Example 21: Statistical Analysis

Statistical analysis was performed using Prism (Version 6.0, GraphPad Software). Data were analyzed using Student's unpaired t test, the log-rank test, or the non-parametric Mann-Whitney test, as appropriate. Normality of data was assessed using the Kolmogorov-Smirnov test. Data are expressed as the mean±SD unless stated otherwise, and all experiments were repeated independently at least three times. P-values of *<0.05, <0.01, or *<0.001 were considered significant according to the analysis.

Experimental Example 1: Anti-Viral Ability of EPRS (Glutamyl-Prolyl-tRNA Synthetase)

Aminoacyl-tRNA synthetases (ARSs) have important roles in diverse non-translational cellular processes, but there is limited information about their roles during viral infection. Thus, the present inventors conducted a global transcriptome analysis using RNA sequencing to assess the expression patterns of the genes encoding MSC (Multi-tRNA synthetase complex) components in human bronchial epithelial cells infected with influenza A virus. Through this, both heterogeneous expression and temporal fluctuation of these genes were observed, which suggested a possible role of the genes in responses to viral infection (FIG. 1).

Then, the present inventors examined the MSC proteins which may trigger antiviral responses, and found that EPRS (glutamyl-prolyl-tRNA synthetase) induced marked activity of IFN-β promoter (FIG. 2) In addition, the expression of EPRS mRNA was gradually induced in different cell lines infected with virus (FIG. 3). When EPRS in RAW264.7 cells (FIG. 4) was knocked down using siRNA, the replication of RNA viruses (PR8 influenza A virus and vesicular stomatitis virus (VSV)) was increased (FIGS. 5 and 6), but the replication of herpes simplex virus (HSV) (DNA virus) was not affected (FIG. 7). EPRS-knocked down cells showed considerable attenuation of the production of antiviral cytokines (IFN-β and IL-6) following viral infection or treatment with the synthetic dsRNA poly(I:C) (FIGS. 8 and 9). However. HSV did not significantly alter cytokine induction (FIGS. 8 and 9). Similar results were obtained from EPRS-knocked down HEK293T cell line (FIGS. 10 to 12) and RAW264.7 cell line stably transduced with shRNA for knockdown of EPRS (FIGS. 13 to 19). Furthermore, activation of the IFN-related signaling molecules IRF3 and STAT1 was significantly lowered in EPRS-knocked down cells (FIG. 20). In contrast, RAW264.7 cells stably overexpressing EPRS (FIG. 21) showed significantly less viral replication and more production of IFN-β and IL-6 following infection with PR8 (FIGS. 22 to 24) or VSV (FIGS. 25 to 27).

Collectively, these data demonstrated that EPRS positively regulated antiviral innate immune responses, specifically those directed against RNA viruses.

Experimental Example 2: In Vivo Defense of EPRS Against Viral Infection

The present inventors used heterozygous EPRS$^{+/-}$ mice to investigate the physiological role of EPRS in antiviral immune responses, because homozygous deletion of EPRS is lethal at the pre-weaning stage. When BMDMs (bone-marrow-derived macrophages) isolated from wild-type (WT, EPRS$^{+/+}$) and EPRS$^{+/-}$ mice infected with PR8 or VSV were examined, the viral titer in EPRS$^{+/-}$ BMDMs was much higher than that in WT BMDMs (FIG. 28). Consistent with that observation, the concentration of IFN-β and IL-6 produced by EPRS$^{+/-}$ BMDMs was significantly lower than that produced by EPRS$^{+/+}$ cells in response to both viral infection (FIG. 29) and treatment with poly(I:C) (FIG. 30). Similar results were obtained from EPRS-knockdown BMDMs transfected using siRNA (FIGS. 31 to 34). Moreover. IFN-β level, antiviral IFN-related gene expression, and inflammation-related gene expression were much lower in VSV-infected EPRS$^{+/-}$ BMDMs than in VSV-infected EPRS$^{+/+}$ cells (FIG. 35).

The induction of antiviral genes in EPRS-knockdown RAW264.7 cells was also much lower following PR8 infection than that in control cells (FIG. 36). In contrast, there was no substantial difference between HSV-infected EPRS$^{+/+}$ and EPRS$^{+/-}$ BMDMs in their viral replication or cytokine secretion (FIGS. 37 and 38).

Next, EPRS$^{+/+}$ and EPRS$^{+/-}$ mice were administered intravenously with the VSV Indiana strain, and their survival was daily monitored. It was found that 43% of EPRS$^{+/-}$ mice (6/14) but only 7% of EPRS$^{+/+}$ mice (1/15) died within 6 days of infection (FIG. 39). To investigate the viral load in mouse tissue, the brain and spleen of mice were sampled and analyzed at day 5 after viral infection. Viral titers in the brain and spleen of EPRS$^{+/-}$ mice were significantly higher than in those of EPRS$^{+/+}$ mice (FIGS. 40 and 41), indicating that EPRS$^{+/-}$ mice were more susceptible to VSV infection.

Next, to further assess the functional importance of EPRS during immune responses, EPRS$^{+/+}$ and EPRS$^{+/-}$ mice were intravenously administered with recombinant VSV-GFP, and measured the viral load and the level of antiviral cytokines in serum samples at 12 hours after infection. As a result, viremia was greater (FIG. 42) and the levels of IFN-β, IFN-α, and IL-6 in the serum were lower (FIG. 43).

Finally, brain tissue samples were collected at 0 to 5 days after infection, and the histological features induced by VSV were assessed. H&E (hematoxylin-eosin)-stained brain sections from EPRS+/− mice showed greater infiltration by inflammatory cells (particularly around the lateral ventricle regions) than that of sections from EPRS+/+ mice (FIG. 44). In addition, immunohistochemical analysis of sectioned brain tissue stained with anti-VSV-G antibody confirmed the presence of infected virus at sites around the inflammation and viral clearance was slower in EPRS+/− mice than in EPRS+/+ mice (FIG. 45).

Taken together, these results demonstrated that EPRS was involved in mouse intracellular innate immune responses to viral infection.

Experimental Example 3: Infection-Specific Modification of EPRS for Antiviral Activity Results of previous studies have reported that post-translational modifications, such as phosphorylation, are key drivers of the release of ARSs from the MSC and subsequent interaction with downstream effector molecules, as well as for activation of non-canonical functions. For example, IFN-γ-dependent sequential phosphorylation of EPRS at Ser886 and Ser999 induces EPRS release from MSC to form the GAIT complex. To assess the function of EPRS following viral infection, the present inventors infected human macrophage-like U937 cells, which are the cell type mainly used for the study of EPRS in the context of IFN-γ activation, with PR8. As a result, the interaction of EPRS with KRS and AIMP3 was significantly reduced following virus infection, indicating dissociation of EPRS from MSC (FIG. 46) Immunoblot analysis with an antibody against NSAP1, which is a component of the pre-GAIT complex that directly binds EPRS via phosphorylation at Ser886, revealed that EPRS bound weakly to NSAP1 at 24 hours. However, EPRS did not bind GAPDH, which is a constituent of GAIT complex that requires phosphorylation of EPRS at Ser999 to allow formation of a functional complex (FIG. 46).

Next, whether EPRS release from MSC is induced by virus was further confirmed by co-immunoprecipitation (co-IP) of PR8-infected RAW264.7 macrophage lysates with anti-EPRS or anti-KRS antibody (FIGS. 47 and 48). Confocal microscopy analysis also revealed that EPRS colocalized with KRS, but the extent of colocalization was reduced following viral infection (FIGS. 49 to 51). These results suggested that a distinct virus-specific mechanism related to EPRS activation exists.

To investigate the mechanism of EPRS activation and its role in antiviral responses, the present inventors next used a mass-spectrometry-based proteomics approach to identify specific post-translational modifications in Strep-tagged EPRS ectopically expressed in HEK293T cells (FIG. 52). Phosphorylation of Ser886 was detected in both uninfected and infected cells, whereas Ser999 (which is phosphorylated following IFN-γ stimulation) was unmodified under all conditions (FIGS. 53 to 55). Unexpectedly, viral infection induced phosphorylation of EPRS at Ser990 (FIGS. 56 and 57). To verify that finding, a rabbit polyclonal antibody directed against this site was prepared by using the phosphorylated peptide $^{983}$DGQRKDP(p)SKNQGGG$^{996}$ (SEQ ID NO: 62) as an antigen. Phosphorylation of EPRS at Ser990 gradually increased after infection of U937 cells with PR8 (FIG. 58). In contrast. IFN-γ treatment did not induce phosphorylation of Ser990 (FIG. 58). Similar results were obtained with other virus- or synthetic-RNA-treated cells (FIGS. 59 to 62).

The present inventors also detected small amounts of Ser886 phosphorylation in uninfected cells, which increased following PR8 infection, although the increase was less than that observed after stimulation by IFN-γ (FIG. 63). Viral infection did not induce phosphorylation of Ser999, whereas IFN-γ stimulation clearly did (FIG. 64). Furthermore, viral infection did not affect the secretion of IFN-γ or suppression of the expression of Cp which is a target of the GAIT complex (FIGS. 65 to 67). The results of the previous studies using ectopically expressed phosphomimetics of EPRS have shown that phosphorylation of Ser886 and Ser999 induces the release of EPRS from MSC. In particular, strep-tagged EPRS mono-phosphomimetic S990D did not interact with the MSC components, KRS, AIMP3, and MRS, indicating inducible release from MSC (FIG. 68).

Taken together, these results suggested that virus-induced phosphorylation of EPRS at Ser990 induced its release from MSC to execute a function distinct from its role in the IFN-γ-activated GAIT translational silencing pathway.

Experimental Example 4: Interaction of EPRS with PCBP2

Following the entry of a virus into cells, the intracellular sensor RIG-I is activated. RIG-I then interacts with MAVS to trigger a signaling cascade that culminates m the production of type I IFN. Analysis of this signaling cascade revealed that EPRS increased RIG-I-, MDA5-, poly(I:C)-, and MAVS-mediated activity of the IFNB promoter in a dose-dependent manner (FIG. 69). However, no substantial activation of the IFN-β promoter was observed in the presence of TRAF3, TBK1, or IRF7 (FIG. 70). These results suggested that EPRS is a positive regulator of the type I IFN pathway and acts downstream of MAVS and upstream of the TRF3 signaling axis.

To identify the EPRS-interacting molecules that regulate MAVS signaling during viral infection, Strep-EPRS-specific complexes from PR8-infected cells were used to perform proteomics analysis (FIG. 71). As a result, it was found that MSC proteins but not GAIT proteins (NSAP, GAPDH, and L13a) exist. Particularly, EPRS interacted with PCBP2 which is known to trigger ubiquitination and degradation of MAVS following viral infection. Endogenous co-IP analysis confirmed the virus-induced interaction of EPRS with PCBP2 in RAW264.7 and U937 cells and that the interaction between the two proteins increased over time (FIGS. 72 and 73). Furthermore, consistent with the results of the previous studies, following viral infection, PCBP2 translocated from the nucleus to the cytoplasm, where it colocalized with EPRS (FIG. 74).

Next, to identify the EPRS region responsible for the interaction with PCBP2, plasmid constructs containing various EPRS domains were prepared (FIG. 75). The amino acid sequence of full-length EPRS is 1512 sequence represented by SEQ ID NO: 63. Then, co-IP was performed to assess the interactions between each EPRS region and PCBP2. As a result, it was revealed that the N-terminal domain of EPRS, which contains GST-like domain and a linker region L1 (an 1-196), was crucial for the interaction with PCBP2 and the region induced IFN-β promoter activation comparable with that induced by full-length EPRS. However, the GST-like domain alone (an 1-168) did not induce antiviral activity (FIGS. 75 to 79). These results suggested that the L1 region (an 168-196) between the GST-like domain and ERS was crucial for both the interaction with PCBP2 and the antiviral responses. The present inventors confirmed that L1-deleted mutant did not interact with PCBP2 and showed diminished ability to activate IFN-β, suggesting that L1 region (aa 168-196) and L1 region-containing fragment (aa 168-269) have antiviral effects (FIGS. 80 and 81).

On the other hand, the present inventors found that the N-terminal KH1 domain (aa 1-81) of PCBP2, not the linker region, was sufficient for binding to EPRS (FIGS. 82 and 83). An in vitro precipitation assay revealed that PCBP2 KH1 specifically interacted with the GST and L1 regions of EPRS but not with the GST-like domain alone (aa 1-168) (FIGS. 84 to 86). Taken together, these data indicated that Ser990-phosphorylation-driven release of EPRS from MSC facilitated its interaction with PCBP2 and potentially regulated MAVS signaling.

Experimental Example 5: Protecting Effect of EPRS on MAVS from PCBP2-Mediated Ubiquitination It has been reported that PCBP2 is induced after viral infection and it interacts with MAVS, leading to ubiquitination of MAVS for proteasomal degradation. Thus, the present inventors hypothesized that EPRS might protect MAVS by blocking PCBP2-mediated ubiquitination. When the interaction of PCBP2 with MAVS was re-evaluated, it was found that MAVS specifically interacted with PCBP2 KH1 domain, which is the domain that bound EPRS (FIGS. 87 to 90). Targeting of the same KH1 domain by EPRS and MAVS suggested that EPRS might compete with MAVS, thereby preventing its interaction with PCBP2.

Indeed, the interaction between PCBP2 and MAVS was significantly reduced in the presence of EPRS (FIG. 91). However, EPRS did not disrupt the binding of PCBP2 to ITCH E3 ligase (FIG. 92), which suggested that EPRS specifically competed with MAVS to bind PCBP2 KH1. These results were confirmed by endogenous interaction assays, which revealed that the binding of PCBP2 to MAVS gradually decreased, whereas its interaction with EPRS markedly increased, after infection with PR8 These results suggested that EPRS acted to counter the endogenous binding of PCBP2 to MAVS in the infected cells (FIG. 93).

PCBP2 accelerates ubiquitin(Ub)-mediated degradation of MAVS by recruiting ITCHE3. Accordingly, the present inventors found that MAVS-FLAG exogenously expressed in 293T cells was ubiquitinated by ITCH and the reaction markedly increased following the addition of PCBP2 (FIG. 94). However, the addition of EPRS inhibited PCBP2-mediated ubiquitination of MAVS in a dose-dependent manner (FIG. 94). Likewise, endogenous ubiquitination of MAVS was greatly enhanced by PCBP2 but was significantly attenuated in the presence of EPRS (FIG. 95). Consistent with the results of the ubiquitination assay, both exogenous MAVS (FIG. 96) and endogenous MAVS (FIG. 97) were degraded by PCBP2, but were rescued from this degradation by the addition of EPRS.

Finally, analysis of a cell-free system reconstituted with purified EPRS revealed much less PCBP2-mediated ubiquitination of MAVS (FIG. 98). Thus, EPRS specifically blocked PCBP2-mediated negative regulation of MAVS, thereby maintaining strong antiviral immune responses.

Experimental Example 6: Antiviral Activity of EPRS-Derived Peptide

Experimental Example 6-1: In Vitro and In Vivo Antiviral Activity of Tat-Epep

Thus far, the present inventors had found that EPRS inhibited PCBP2-mediated degradation of MAVS in antiviral immune responses, and particularly. EPRS L1 region (aa 168-196) was both crucial for interaction with PCBP2 and responsible for promoting antiviral type I IFN signaling. The present inventors next designed a cell-penetrating peptide by fusing the HIV-1 Tat protein transduction domain to the EPRS L1 region (hereinafter, referred to as "Tat-Epep", SEQ ID NO: 61), and assessed its effects on antiviral activity. Tat-Epep compromised PCBP2-mediated endogenous ubiquitination of MAVS (FIG. 99) and restored the cellular expression of MAVS (FIG. 100). Tat-Epep also increased the production of IFN-β and IL-6 in virus-infected cells (FIG. 101) and reduced VSV replication in RAW264.7 cells in a dose-dependent manner (FIGS. 102 and 103). However, Tat-Epep showed no substantial antiviral activity in RAW264.7 cells infected with HSV (FIGS. 104 to 106), suggesting that Tat-Epep was specific to infection with RNA viruses. Tat-Epep had no effect on the viability of RAW264.7 or 293T cells at the concentrations tested, indicating that the diminished viral titer was not a result of peptide-mediated cytotoxicity (FIGS. 107 and 108). These results suggested that Tat-Epep might be a potential anti-RNA virus agent that promotes MAVS stability and type I IFN production.

To further examine the antiviral effect of Tat-Epep in vivo, the present inventors intravenously administered VSV-Indiana strain to mice. After injection, Tat or Tat-Epep was intraperitoneally administered to the mice daily for 3 days. As a result. Tat-Epep-treated mice showed significant decreases in viral titers in the brain tissues, as compared with Tat-tag-treated mice (FIG. 109). These data also demonstrated that Tat-Epep might be effective as a potential anti-RNA virus agent.

Experimental Example 6-2: In Vitro and In Vivo Antiviral Activity of New Tat-Epep The present inventors prepared a new peptide (hereinafter, referred to as "New Tat-Epep") by using 21-mer (aa 166-186) as the EPRS peptide fragment of Tat-Epep. The New Tat-Epep has an amino acid sequence of YGRKKRRQRRR-GG-KWDVSTTKARVAPEKKQDVGK (SEQ ID NO: 64). In the same manner as in Example 6-1, the New Tat-Epep was treated to mice which had been intravenously injected with VSV (TAT-control group: 100 μg, 7 mice: New Tat-Epep: 200 μg, 3 mice). Consequently, as in the Tat-Epep, the New Tat-Epep was found to decrease VSV viral titers in the mouse brains (FIG. 110). Furthermore, when the New Tat-Epep was treated to VSV-GAP virus-infected RAW264.7 cells, the New Tat-Epep induced a 2- to 3-fold increase m the secretion of antiviral cytokines IFN-β and IL-6, as compared with Tat-Epep (FIGS. 111 to 113). These results demonstrated that New Tat-Epep might be also effective as an anti-RNA virus agent.

Accordingly, it can be seen that only the fragment of aa 168-186, lacking aa 187-196, in EPRS L (aa 168-196) has excellent anti-RNA viral activity.

Experimental Example 7: Antiviral Activity of Conjugate of EPRS-Derived Peptide

Next, the present inventors prepared a conjugate (hereinafter, referred to as "EPRS conjugate") in which a drug delivery vehicle is bound to the EPRS protein or the fragment thereof, and identified the intracellular delivery effect and antiviral activity of the EPRS conjugate.

Specifically, while preparing the EPRS conjugate, an amino acid sequence at positions 166 to 186 in SEQ ID NO: 63 was used as the EPRS protein or the fragment thereof. The conjugate, in which TAMRA fluorophore (Abs/

Em=555/580 nm) and the fragment of the EPRS protein are bound (custom ordered in Peptrone company, hereinafter referred to as "T-sEpep"), was incubated together with poly(ethylene glycol) 2-mercaptoethyl ether acetic acid (purchased in Sigma-Aldrich, product name: 757829) having an average molecular mass of 2100 Da so that T-sEpep was coated with PEG. A new EPRS conjugate (hereinafter, "AuNP-PEG-T-sEpep") was prepared by forming an electrostatic interaction by incubating the coated conjugate with gold nanoparticles (hereinafter referred to as "AuNP") having a size of 10 nm for 1 hour. The form of the conjugate may be represented as shown in FIG. 114.

As a result of treating RAW 264.7 cells with AuNP-PEG-T-sEpep (T-sEpep-control group: 1 μm: AuNP-PEG-T-sEpep: 1 μm), AuNP-PEG-T-sEpep were confirmed to be effectively delivered into cells compared to T-sEpep without AuNP and PEG (FIG. 115). Through the results, it was confirmed that forming a conjugate with the EPRS protein or the fragment thereof leads the EPRS protein or the fragment thereof to be effectively delivered into the cells even at low concentrations.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the present invention is defined by the appended claims rather than by the description preceding them, and therefore all changes and modifications that fall within metes and bounds of the claims, or equivalents of such metes and bounds are therefore intended to be embraced by the claims.

Effect of the Invention

The EPRS protein of the present invention or the fragment thereof may bind to PCBP2 protein to activate the MAVS signaling pathway which is crucial for all anti-RNA viral activities, and thus it has universal anti-RNA viral effects, thereby being effective for preventing or treating a RNA viral infectious disease.

What is claimed is:

1. A method of treating an RNA viral infectious disease in a subject in need thereof, comprising administering to the subject in need thereof a fragment of an EPRS (glutamyl-prolyl-tRNA synthetase) protein that is optionally bound to a drug delivery vehicle, wherein the fragment of the EPRS protein consists of an amino acid sequence selected from the group consisting of the amino acid sequence at positions 166 to 506, the amino acid sequence at positions 168 to 506, the amino acid sequence at positions 166 to 269, the amino acid sequence at positions 168 to 269, the amino acid sequence at positions 166 to 196, the amino acid sequence at positions 168 to 196, the amino acid sequence at positions 166 to 186, and the amino acid sequence at positions 168 to 186 in SEQ ID NO: 63.

2. The method of claim 1, wherein the fragment of the EPRS protein consists of the amino acid sequence at positions 168 to 186 in SEQ ID NO: 63.

3. The method of claim 1, wherein the RNA viral infectious disease agent is one or more selected from the group consisting of Amalgaviridae, Birnaviridae, Chrysoviridae, Cystoviridae, Endornaviridae, Hypoviridae, Megabirnaviridae, Partitiviridae, Picobirnaviridae, Reoviridae, Totiviridae, Quadriviridae, Arteriviridae, Coronaviridae, Mesoniviridae, Roniviridae, Dicistroviridae, Iflaviridae, Marnaviridae, Picornaviridae, Secoviridae, Alphaflexiviridae, Betaflexiviridae, Gammaflexiviridae, Tymoviridae, Bornaviridae, Filoviridae, Paramyxoviridae, Rhabdoviridae, Nyamiviridae, Caliciviridae, Flaviviridae, Luteoviridae, Togaviridae, Pneumoviridae, Arenaviridae, Deltavirus, and Orthomyxoviridae viruses.

4. The method of claim 1, wherein the fragment of the EPRS protein is bound to the drug delivery vehicle.

5. The method of claim 4, wherein the drug delivery vehicle is selected from the group consisting of a labeling material, a targeting ligand, a cell-penetrating peptide, a polymeric nanoparticle, a viral vector, a virus-like particle, and an inorganic nanoparticle.

6. The method of claim 5, wherein the cell-penetrating peptide is selected from the group consisting of Tat, Antennapedia, Transportan, VP22, Hph-1, R11 (SEQ ID NO: 71), and R9 (SEQ ID NO: 72).

7. A method of inhibiting MAVS protein degradation in a subject in need thereof, comprising administering to the subject in need thereof a fragment of an EPRS (glutamyl-proplyl-tRNA synthetase) protein, wherein the fragment of the EPRS protein consists of an amino acid sequence selected from the group consisting of the amino acid sequence at positions 166 to 506, the amino acid sequence at positions 168 to 506, the amino acid sequence at positions 166 to 269, the amino acid sequence at positions 168 to 269, the amino acid sequence at positions 166 to 196, the amino acid sequence at positions 168 to 196, the amino acid sequence at positions 166 to 186, and the amino acid sequence at positions 168 to 186 in SEQ ID NO: 63.

8. A fragment of an EPRS protein bound to a drug delivery vehicle, wherein the fragment of the EPRS protein consists of an amino acid sequence selected from the group consisting of the amino acid sequence at positions 166 to 506, the amino acid sequence at positions 168 to 506, the amino acid sequence at positions 166 to 269, the amino acid sequence at positions 168 to 269, the amino acid sequence at positions 166 to 196, the amino acid sequence at positions 168 to 196, the amino acid sequence at positions 166 to 186, and the amino acid sequence at positions 168 to 186 in SEQ ID NO: 63.

9. The fragment of the EPRS protein bound to a drug delivery vehicle of claim 8, wherein the fragment of the EPRS protein consists of the amino acid sequence at positions 168 to 186 of SEQ ID NO: 63.

10. The fragment of the EPRS protein bound to a drug delivery vehicle of claim 8, wherein the drug delivery vehicle is bound to the fragment of the EPRS protein via a linker.

11. The fragment of the EPRS protein bound to a drug delivery vehicle of claim 8, wherein the drug delivery vehicle is selected from the group consisting of a labeling material, a targeting ligand, a cell-penetrating peptide, a polymeric nanoparticle, a viral vector, a virus-like particle, and an inorganic nanoparticle.

12. The fragment of the EPRS protein of claim 11, wherein the cell-penetrating peptide is selected from the group consisting of Tat, Antennapedia, Transportan, VP22, Hph-1, R11 (SEQ ID NO: 71), and R9 (SEQ ID NO: 72).

13. A polynucleotide encoding the fragment of the EPRS protein bound to a drug delivery vehicle of claim 8.

14. A vector comprising the polynucleotide of claim 13.

15. A transformant comprising the polynucleotide of claim 13.

16. A composition comprising the fragment of the EPRS protein bound to a drug delivery vehicle of claim 8.

17. The composition of claim 16, wherein the composition further comprises a non-naturally occurring carrier.

18. The method according to claim 1, wherein the subject is diagnosed with an RNA viral infectious disease.

19. The method of claim 1, wherein the fragment of the EPRS protein that is optionally bound to a drug delivery vehicle is Tat-Epep (SEQ ID NO: 64).

\* \* \* \* \*

SEQUENCE LISTING

<160> NUMBER OF SEQ ID NOS: 70

<210> SEQ ID NO 1
<211> LENGTH: 23
<212> TYPE: DNA
<213> ORGANISM: Artificial Sequence
<220> FEATURE:
<223> OTHER INFORMATION: WT-specific primer-1

<400> SEQUENCE: 1
tactgtgctg aatgaaaagt gcc                           23

<210> SEQ ID NO 2
<211> LENGTH: 25
<212> TYPE: DNA
<213> ORGANISM: Artificial Sequence
<220> FEATURE:
<223> OTHER INFORMATION: WT-specific primer-2

<400> SEQUENCE: 2
ggtagaagtg ctaagtagga tgagg                         25

<210> SEQ ID NO 3
<211> LENGTH: 23
<212> TYPE: DNA
<213> ORGANISM: Artificial Sequence
<220> FEATURE:
<223> OTHER INFORMATION: mutant-specific primer-1

<400> SEQUENCE: 3
ccattaccag ttggtctggt gtc                           23

<210> SEQ ID NO 4
<211> LENGTH: 26
<212> TYPE: DNA
<213> ORGANISM: Artificial Sequence
<220> FEATURE:
<223> OTHER INFORMATION: mutant-specific primer-2

<400> SEQUENCE: 4
tgcctgtgac caccaataag aaagcc                        26

<210> SEQ ID NO 5

```
<211> LENGTH: 14
<212> TYPE: PRT
<213> ORGANISM: Artificial Sequence
<220> FEATURE:
<223> OTHER INFORMATION: ser990 antigen
<220> FEATURE:
<221> NAME/KEY: MOD_RES
<222> LOCATION: (8)
<223> OTHER INFORMATION: PHOSPHORYLATION,

<400> SEQUENCE: 5

Asp Gly Gln Arg Lys Asp Pro Ser Lys Asn Gln Gly Gly Gly
1               5                   10

<210> SEQ ID NO 6
<211> LENGTH: 15
<212> TYPE: DNA
<213> ORGANISM: Artificial Sequence
<220> FEATURE:
<223> OTHER INFORMATION: hEPRS primer F

<400> SEQUENCE: 6
cttctcaagg ggaag                                                15

<210> SEQ ID NO 7
<211> LENGTH: 15
<212> TYPE: DNA
<213> ORGANISM: Artificial Sequence
<220> FEATURE:
<223> OTHER INFORMATION: hEPRS primer R

<400> SEQUENCE: 7
ctgcttttca gattt                                                15

<210> SEQ ID NO 8
<211> LENGTH: 20
<212> TYPE: DNA
<213> ORGANISM: Artificial Sequence
<220> FEATURE:
<223> OTHER INFORMATION: mEPRS primer F

<400> SEQUENCE: 8
aagcggaaaa ggctcctaag                                           20

<210> SEQ ID NO 9
<211> LENGTH: 26
<212> TYPE: DNA
<213> ORGANISM: Artificial Sequence
<220> FEATURE:
<223> OTHER INFORMATION: mEPRS primer R

<400> SEQUENCE: 9
cccagtcttt tctttatact cagctt                                    26

<210> SEQ ID NO 10
<211> LENGTH: 25
<212> TYPE: DNA
<213> ORGANISM: Artificial Sequence
<220> FEATURE:
<223> OTHER INFORMATION: IFN-a primer F

<400> SEQUENCE: 10
cttgaaggac agacatgact ttgga                                     25

<210> SEQ ID NO 11
<211> LENGTH: 21
<212> TYPE: DNA
```

```
<213> ORGANISM: Artificial Sequence
<220> FEATURE:
<223> OTHER INFORMATION: IFN-a primer R

<400> SEQUENCE: 11
ggatggtttc agcctttgg a                                              21

<210> SEQ ID NO 12
<211> LENGTH: 22
<212> TYPE: DNA
<213> ORGANISM: Artificial Sequence
<220> FEATURE:
<223> OTHER INFORMATION: IFN-b primer F

<400> SEQUENCE: 12
tccaagaaag gacgaacatt cg                                            22

<210> SEQ ID NO 13
<211> LENGTH: 21
<212> TYPE: DNA
<213> ORGANISM: Artificial Sequence
<220> FEATURE:
<223> OTHER INFORMATION: IFN-b primer R

<400> SEQUENCE: 13
tgcggacatc tcccaacgtc a                                             21

<210> SEQ ID NO 14
<211> LENGTH: 18
<212> TYPE: DNA
<213> ORGANISM: Artificial Sequence
<220> FEATURE:
<223> OTHER INFORMATION: ADAR1 primer F

<400> SEQUENCE: 14
ccaaagacac ttcctctc                                                 18

<210> SEQ ID NO 15
<211> LENGTH: 18
<212> TYPE: DNA
<213> ORGANISM: Artificial Sequence
<220> FEATURE:
<223> OTHER INFORMATION: ADAR1 primer R

<400> SEQUENCE: 15
cagtgtggtg gttgtact                                                 18

<210> SEQ ID NO 16
<211> LENGTH: 23
<212> TYPE: DNA
<213> ORGANISM: Artificial Sequence
<220> FEATURE:
<223> OTHER INFORMATION: MX1 primer F

<400> SEQUENCE: 16
acaagcacag gaaaccgtat cag                                           23

<210> SEQ ID NO 17
<211> LENGTH: 23
<212> TYPE: DNA
<213> ORGANISM: Artificial Sequence
<220> FEATURE:
<223> OTHER INFORMATION: MX1 primer R

<400> SEQUENCE: 17
aggcagtttg gaccatctta gtg                                           23
```

<210> SEQ ID NO 18
<211> LENGTH: 20
<212> TYPE: DNA
<213> ORGANISM: Artificial Sequence
<220> FEATURE:
<223> OTHER INFORMATION: OAS1 primer F

<400> SEQUENCE: 18
gaggcggttg gctgaagagg                                               20

<210> SEQ ID NO 19
<211> LENGTH: 22
<212> TYPE: DNA
<213> ORGANISM: Artificial Sequence
<220> FEATURE:
<223> OTHER INFORMATION: OAS1 primer R

<400> SEQUENCE: 19
gaggaaggct ggctgtgatt gg                                            22

<210> SEQ ID NO 20
<211> LENGTH: 20
<212> TYPE: DNA
<213> ORGANISM: Artificial Sequence
<220> FEATURE:
<223> OTHER INFORMATION: OAS1b primer F

<400> SEQUENCE: 20
ttgatgtgct gccagcctat                                               20

<210> SEQ ID NO 21
<211> LENGTH: 20
<212> TYPE: DNA
<213> ORGANISM: Artificial Sequence
<220> FEATURE:
<223> OTHER INFORMATION: OAS1b primer R

<400> SEQUENCE: 21
tgaggcgctt cagcttggtt                                               20

<210> SEQ ID NO 22
<211> LENGTH: 20
<212> TYPE: DNA
<213> ORGANISM: Artificial Sequence
<220> FEATURE:
<223> OTHER INFORMATION: PKR primer F

<400> SEQUENCE: 22
gccagatgca cggagtagcc                                               20

<210> SEQ ID NO 23
<211> LENGTH: 21
<212> TYPE: DNA
<213> ORGANISM: Artificial Sequence
<220> FEATURE:
<223> OTHER INFORMATION: PKR primer R

<400> SEQUENCE: 23
gaaaacttgg ccaaatccac c                                             21

<210> SEQ ID NO 24
<211> LENGTH: 22
<212> TYPE: DNA
<213> ORGANISM: Artificial Sequence
<220> FEATURE:

<223> OTHER INFORMATION: PML primer F

<400> SEQUENCE: 24
cctgcgctga ctgacatcta ct                                    22

<210> SEQ ID NO 25
<211> LENGTH: 18
<212> TYPE: DNA
<213> ORGANISM: Artificial Sequence
<220> FEATURE:
<223> OTHER INFORMATION: PML primer R

<400> SEQUENCE: 25
tgcaacacag aggctggc                                         18

<210> SEQ ID NO 26
<211> LENGTH: 20
<212> TYPE: DNA
<213> ORGANISM: Artificial Sequence
<220> FEATURE:
<223> OTHER INFORMATION: P56 primer F

<400> SEQUENCE: 26
cccacgctat accatctacc                                       20

<210> SEQ ID NO 27
<211> LENGTH: 18
<212> TYPE: DNA
<213> ORGANISM: Artificial Sequence
<220> FEATURE:
<223> OTHER INFORMATION: P56 primer R

<400> SEQUENCE: 27
ctgaggctgc tgctatcc                                         18

<210> SEQ ID NO 28
<211> LENGTH: 19
<212> TYPE: DNA
<213> ORGANISM: Artificial Sequence
<220> FEATURE:
<223> OTHER INFORMATION: ISG15 primer F

<400> SEQUENCE: 28
caatggcctg ggacctaaa                                        19

<210> SEQ ID NO 29
<211> LENGTH: 24
<212> TYPE: DNA
<213> ORGANISM: Artificial Sequence
<220> FEATURE:
<223> OTHER INFORMATION: ISG15 primer R

<400> SEQUENCE: 29
cttcttcagt tctgacaccg tcat                                  24

<210> SEQ ID NO 30
<211> LENGTH: 20
<212> TYPE: DNA
<213> ORGANISM: Artificial Sequence
<220> FEATURE:
<223> OTHER INFORMATION: ISG20 primer F

<400> SEQUENCE: 30
agagatcacg gactacagaa                                       20

```
<210> SEQ ID NO 31
<211> LENGTH: 20
<212> TYPE: DNA
<213> ORGANISM: Artificial Sequence
<220> FEATURE:
<223> OTHER INFORMATION: ISG20 primer R

<400> SEQUENCE: 31
tctgtggacg tgtcatagat                                               20

<210> SEQ ID NO 32
<211> LENGTH: 20
<212> TYPE: DNA
<213> ORGANISM: Artificial Sequence
<220> FEATURE:
<223> OTHER INFORMATION: ISG56 primer F

<400> SEQUENCE: 32
agagaacagc taccaccttt                                               20

<210> SEQ ID NO 33
<211> LENGTH: 20
<212> TYPE: DNA
<213> ORGANISM: Artificial Sequence
<220> FEATURE:
<223> OTHER INFORMATION: ISG56 primer R

<400> SEQUENCE: 33
tggacctgct ctgagattct                                               20

<210> SEQ ID NO 34
<211> LENGTH: 19
<212> TYPE: DNA
<213> ORGANISM: Artificial Sequence
<220> FEATURE:
<223> OTHER INFORMATION: GAPDH primer F

<400> SEQUENCE: 34
tgaccacagt ccatgccat                                                19

<210> SEQ ID NO 35
<211> LENGTH: 20
<212> TYPE: DNA
<213> ORGANISM: Artificial Sequence
<220> FEATURE:
<223> OTHER INFORMATION: GAPDH primer R

<400> SEQUENCE: 35
gacggacaca ttgggggtag                                               20

<210> SEQ ID NO 36
<211> LENGTH: 25
<212> TYPE: DNA
<213> ORGANISM: Artificial Sequence
<220> FEATURE:
<223> OTHER INFORMATION: VSV-G primer F

<400> SEQUENCE: 36
caagtcaaaa tgcccaagag tcaca                                         25

<210> SEQ ID NO 37
<211> LENGTH: 25
<212> TYPE: DNA
<213> ORGANISM: Artificial Sequence
<220> FEATURE:
<223> OTHER INFORMATION: VSV-G primer R
```

<400> SEQUENCE: 37
tttccttgca ttgttctaca gatgg                                          25

<210> SEQ ID NO 38
<211> LENGTH: 43
<212> TYPE: DNA
<213> ORGANISM: Artificial Sequence
<220> FEATURE:
<223> OTHER INFORMATION: EPRS S886D primer F

<400> SEQUENCE: 38
cccccattat ctcaaagttc ggattcagac ccaaccagaa att                      43

<210> SEQ ID NO 39
<211> LENGTH: 43
<212> TYPE: DNA
<213> ORGANISM: Artificial Sequence
<220> FEATURE:
<223> OTHER INFORMATION: EPRS S886D primer R

<400> SEQUENCE: 39
aatttctggt tgggtctgaa tccgaacttt gagataatgg ggg                      43

<210> SEQ ID NO 40
<211> LENGTH: 40
<212> TYPE: DNA
<213> ORGANISM: Artificial Sequence
<220> FEATURE:
<223> OTHER INFORMATION: EPRS S990D primer F

<400> SEQUENCE: 40
cacacaaagg aaagaccctg ataaaaacca aggaggtggg                          40

<210> SEQ ID NO 41
<211> LENGTH: 40
<212> TYPE: DNA
<213> ORGANISM: Artificial Sequence
<220> FEATURE:
<223> OTHER INFORMATION: EPRS S990D primer R

<400> SEQUENCE: 41
cccacctcct tggtttttat cagggtcttt cctttgtgtg                          40

<210> SEQ ID NO 42
<211> LENGTH: 44
<212> TYPE: DNA
<213> ORGANISM: Artificial Sequence
<220> FEATURE:
<223> OTHER INFORMATION: EPRS S999D primer F

<400> SEQUENCE: 42
tctaaaaacc aaggaggtgg gctctcagat agtggagcag gaga                     44

<210> SEQ ID NO 43
<211> LENGTH: 44
<212> TYPE: DNA
<213> ORGANISM: Artificial Sequence
<220> FEATURE:
<223> OTHER INFORMATION: EPRS S999D primer R

<400> SEQUENCE: 43
tctcctgctc cactatctga gagcccacct ccttggtttt taga                     44

<210> SEQ ID NO 44
<211> LENGTH: 35

-continued

```
<212> TYPE: DNA
<213> ORGANISM: Artificial Sequence
<220> FEATURE:
<223> OTHER INFORMATION: EPRS S990A primer F

<400> SEQUENCE: 44
gccaaaggaa agaccctgct aaaaaccaag gaggt                              35

<210> SEQ ID NO 45
<211> LENGTH: 35
<212> TYPE: DNA
<213> ORGANISM: Artificial Sequence
<220> FEATURE:
<223> OTHER INFORMATION: EPRS S990A primer R

<400> SEQUENCE: 45
acctccttgg tttttagcag ggtctttcct ttggc                              35

<210> SEQ ID NO 46
<211> LENGTH: 44
<212> TYPE: DNA
<213> ORGANISM: Artificial Sequence
<220> FEATURE:
<223> OTHER INFORMATION: EPRS R201L primer F

<400> SEQUENCE: 46
gagatgggaa aggttaccgt cttatttcct ccagaggcca gtgg                    44

<210> SEQ ID NO 47
<211> LENGTH: 44
<212> TYPE: DNA
<213> ORGANISM: Artificial Sequence
<220> FEATURE:
<223> OTHER INFORMATION: EPRS R201L primer R

<400> SEQUENCE: 47
ccactggcct ctggaggaaa taagacggta acctttccca tctc                    44

<210> SEQ ID NO 48
<211> LENGTH: 41
<212> TYPE: DNA
<213> ORGANISM: Artificial Sequence
<220> FEATURE:
<223> OTHER INFORMATION: EPRS R395L primer F

<400> SEQUENCE: 48
gaaggtgtta cacatgccct gttaacagaa taccatgaca g                       41

<210> SEQ ID NO 49
<211> LENGTH: 44
<212> TYPE: DNA
<213> ORGANISM: Artificial Sequence
<220> FEATURE:
<223> OTHER INFORMATION: EPRS R395L primer R

<400> SEQUENCE: 49
ctgtcatggt attctgttgt taacagggca tgtgtaacac cttc                    44

<210> SEQ ID NO 50
<211> LENGTH: 43
<212> TYPE: DNA
<213> ORGANISM: Artificial Sequence
<220> FEATURE:
<223> OTHER INFORMATION: EPRS S434A/K435L primer F

<400> SEQUENCE: 50
```
ctcaacaaca cagtgctagc gctgagaaaa ctcacatggt ttg          43

<210> SEQ ID NO 51
<211> LENGTH: 43
<212> TYPE: DNA
<213> ORGANISM: Artificial Sequence
<220> FEATURE:
<223> OTHER INFORMATION: EPRS S434A/K435L primer R

<400> SEQUENCE: 51
caaaccatgt gagttttctc agcgctagca ctgtgttgtt gag          43

<210> SEQ ID NO 52
<211> LENGTH: 35
<212> TYPE: DNA
<213> ORGANISM: Artificial Sequence
<220> FEATURE:
<223> OTHER INFORMATION: EPRS R1152L primer F

<400> SEQUENCE: 52
gtggtgcaat gtggtgcttt gggaattcaa gcatc                   35

<210> SEQ ID NO 53
<211> LENGTH: 35
<212> TYPE: DNA
<213> ORGANISM: Artificial Sequence
<220> FEATURE:
<223> OTHER INFORMATION: EPRS R1152L primer R

<400> SEQUENCE: 53
gatgcttgaa ttcccaaagc accacattgc accac                   35

<210> SEQ ID NO 54
<211> LENGTH: 19
<212> TYPE: RNA
<213> ORGANISM: Artificial Sequence
<220> FEATURE:
<223> OTHER INFORMATION: hEPRS siRNA

<400> SEQUENCE: 54
cuaauuccuc agcaaguau                                     19

<210> SEQ ID NO 55
<211> LENGTH: 19
<212> TYPE: RNA
<213> ORGANISM: Artificial Sequence
<220> FEATURE:
<223> OTHER INFORMATION: mEPRS siRNA

<400> SEQUENCE: 55
caaagucauc aucaaacac                                     19

<210> SEQ ID NO 56
<211> LENGTH: 21
<212> TYPE: RNA
<213> ORGANISM: Artificial Sequence
<220> FEATURE:
<223> OTHER INFORMATION: mMAVS 1 siRNA

<400> SEQUENCE: 56
uugcugagga caagaccuau a                                  21

<210> SEQ ID NO 57
<211> LENGTH: 19
<212> TYPE: RNA
<213> ORGANISM: Artificial Sequence

```
<220> FEATURE:
<223> OTHER INFORMATION: mMAVS 2 siRNA

<400> SEQUENCE: 57
cagaggagaa ugaguauuc                                              19

<210> SEQ ID NO 58
<211> LENGTH: 23
<212> TYPE: DNA
<213> ORGANISM: Artificial Sequence
<220> FEATURE:
<223> OTHER INFORMATION: sgEPRS 1

<400> SEQUENCE: 58
gaattctata cttcgctact tgg                                         23

<210> SEQ ID NO 59
<211> LENGTH: 23
<212> TYPE: DNA
<213> ORGANISM: Artificial Sequence
<220> FEATURE:
<223> OTHER INFORMATION: sgEPRS 2

<400> SEQUENCE: 59
gctagagttg caactacagc tgg                                         23

<210> SEQ ID NO 60
<211> LENGTH: 11
<212> TYPE: PRT
<213> ORGANISM: Artificial Sequence
<220> FEATURE:
<223> OTHER INFORMATION: HIV-1 TAT peptide

<400> SEQUENCE: 60

Tyr Gly Arg Lys Lys Arg Arg Gln Arg Arg Arg
1               5                   10

<210> SEQ ID NO 61
<211> LENGTH: 42
<212> TYPE: PRT
<213> ORGANISM: Artificial Sequence
<220> FEATURE:
<223> OTHER INFORMATION: Tat-Epep

<400> SEQUENCE: 61

Tyr Gly Arg Lys Lys Arg Arg Gln Arg Arg Arg Gly Gly Asp Val Ser
1               5                   10                  15

Thr Thr Lys Ala Arg Val Ala Pro Glu Lys Lys Gln Asp Val Gly Lys
            20                  25                  30

Phe Val Glu Leu Pro Gly Ala Glu Met Gly
        35                  40

<210> SEQ ID NO 62
<211> LENGTH: 14
<212> TYPE: PRT
<213> ORGANISM: Artificial Sequence
<220> FEATURE:
<223> OTHER INFORMATION: ser990 antigen
<220> FEATURE:
<221> NAME/KEY: MOD_RES
<222> LOCATION: (8)
<223> OTHER INFORMATION: PHOSPHORYLATION,

<400> SEQUENCE: 62

Asp Gly Gln Arg Lys Asp Pro Ser Lys Asn Gln Gly Gly Gly
1               5                   10
```

-continued

<210> SEQ ID NO 63
<211> LENGTH: 1512
<212> TYPE: PRT
<213> ORGANISM: Artificial Sequence
<220> FEATURE:
<223> OTHER INFORMATION: EPRS full-length

<400> SEQUENCE: 63

```
Met Ala Thr Leu Ser Leu Thr Val Asn Ser Gly Asp Pro Leu Gly
1               5                   10                  15

Ala Leu Leu Ala Val Glu His Val Lys Asp Val Ser Ile Ser Val
                20                  25                  30

Glu Glu Gly Lys Glu Asn Ile Leu His Val Ser Glu Asn Val Ile Phe
            35                  40                  45

Thr Asp Val Asn Ser Ile Leu Arg Tyr Leu Ala Arg Val Ala Thr Thr
        50                  55                  60

Ala Gly Leu Tyr Gly Ser Asn Leu Met Glu His Thr Glu Ile Asp His
65                  70                  75                  80

Trp Leu Glu Phe Ser Ala Thr Lys Leu Ser Ser Cys Asp Ser Phe Thr
                85                  90                  95

Ser Thr Ile Asn Glu Leu Asn His Cys Leu Ser Leu Arg Thr Tyr Leu
                100                 105                 110

Val Gly Asn Ser Leu Ser Leu Ala Asp Leu Cys Val Trp Ala Thr Leu
                115                 120                 125

Lys Gly Asn Ala Ala Trp Gln Glu Gln Leu Lys Gln Lys Lys Ala Pro
            130                 135                 140

Val His Val Lys Arg Trp Phe Gly Phe Leu Glu Ala Gln Gln Ala Phe
145                 150                 155                 160

Gln Ser Val Gly Thr Lys Trp Asp Val Ser Thr Thr Lys Ala Arg Val
                165                 170                 175

Ala Pro Glu Lys Lys Gln Asp Val Gly Lys Phe Val Glu Leu Pro Gly
            180                 185                 190

Ala Glu Met Gly Lys Val Thr Val Arg Phe Pro Pro Glu Ala Ser Gly
        195                 200                 205

Tyr Leu His Ile Gly His Ala Lys Ala Ala Leu Leu Asn Gln His Tyr
    210                 215                 220

Gln Val Asn Phe Lys Gly Lys Leu Ile Met Arg Phe Asp Asp Thr Asn
225                 230                 235                 240

Pro Glu Lys Glu Lys Glu Asp Phe Glu Lys Val Ile Leu Glu Asp Val
                245                 250                 255

Ala Met Leu His Ile Lys Pro Asp Gln Phe Thr Tyr Thr Ser Asp His
            260                 265                 270

Phe Glu Thr Ile Met Lys Tyr Ala Glu Lys Leu Ile Gln Glu Gly Lys
        275                 280                 285

Ala Tyr Val Asp Asp Thr Pro Ala Glu Gln Met Lys Ala Glu Arg Glu
    290                 295                 300

Gln Arg Ile Asp Ser Lys His Arg Lys Asn Pro Ile Glu Lys Asn Leu
305                 310                 315                 320

Gln Met Trp Glu Glu Met Lys Lys Gly Ser Gln Phe Gly Gln Ser Cys
                325                 330                 335

Cys Leu Arg Ala Lys Ile Asp Met Ser Ser Asn Asn Gly Cys Met Arg
            340                 345                 350

Asp Pro Thr Leu Tyr Arg Cys Lys Ile Gln Pro His Pro Arg Thr Gly
        355                 360                 365
```

```
Asn Lys Tyr Asn Val Tyr Pro Thr Tyr Asp Phe Ala Cys Pro Ile Val
    370                 375                 380

Asp Ser Ile Glu Gly Val Thr His Ala Leu Arg Thr Thr Glu Tyr His
385                 390                 395                 400

Asp Arg Asp Glu Gln Phe Tyr Trp Ile Ile Glu Ala Leu Gly Ile Arg
                405                 410                 415

Lys Pro Tyr Ile Trp Glu Tyr Ser Arg Leu Asn Leu Asn Asn Thr Val
            420                 425                 430

Leu Ser Lys Arg Lys Leu Thr Trp Phe Val Asn Glu Gly Leu Val Asp
        435                 440                 445

Gly Trp Asp Asp Pro Arg Phe Pro Thr Val Arg Gly Val Leu Arg Arg
450                 455                 460

Gly Met Thr Val Glu Gly Leu Lys Gln Phe Ile Ala Ala Gln Gly Ser
465                 470                 475                 480

Ser Arg Ser Val Val Asn Met Glu Trp Asp Lys Ile Trp Ala Phe Asn
                485                 490                 495

Lys Lys Val Ile Asp Pro Val Ala Pro Arg Tyr Val Ala Leu Leu Lys
            500                 505                 510

Lys Glu Val Ile Pro Val Asn Val Pro Glu Ala Gln Glu Glu Met Lys
        515                 520                 525

Glu Val Ala Lys His Pro Lys Asn Pro Glu Val Gly Leu Lys Pro Val
530                 535                 540

Trp Tyr Ser Pro Lys Val Phe Ile Glu Gly Ala Asp Ala Glu Thr Phe
545                 550                 555                 560

Ser Glu Gly Glu Met Val Thr Phe Ile Asn Trp Gly Asn Leu Asn Ile
                565                 570                 575

Thr Lys Ile His Lys Asn Ala Asp Gly Lys Ile Ile Ser Leu Asp Ala
            580                 585                 590

Lys Leu Asn Leu Glu Asn Lys Asp Tyr Lys Lys Thr Thr Lys Val Thr
        595                 600                 605

Trp Leu Ala Glu Thr Thr His Ala Leu Pro Ile Pro Val Ile Cys Val
610                 615                 620

Thr Tyr Glu His Leu Ile Thr Lys Pro Val Leu Gly Lys Asp Glu Asp
625                 630                 635                 640

Phe Lys Gln Tyr Val Asn Lys Asn Ser Lys His Glu Glu Leu Met Leu
                645                 650                 655

Gly Asp Pro Cys Leu Lys Asp Leu Lys Lys Gly Asp Ile Ile Gln Leu
            660                 665                 670

Gln Arg Arg Gly Phe Phe Ile Cys Asp Gln Pro Tyr Glu Pro Val Ser
        675                 680                 685

Pro Tyr Ser Cys Lys Glu Ala Pro Cys Val Leu Ile Tyr Ile Pro Asp
690                 695                 700

Gly His Thr Lys Glu Met Pro Thr Ser Gly Ser Lys Glu Lys Thr Lys
705                 710                 715                 720

Val Glu Ala Thr Lys Asn Glu Thr Ser Ala Pro Phe Lys Glu Arg Pro
                725                 730                 735

Thr Pro Ser Leu Asn Asn Asn Cys Thr Thr Ser Glu Asp Ser Leu Val
            740                 745                 750

Leu Tyr Asn Arg Val Ala Val Gln Gly Asp Val Val Arg Glu Leu Lys
        755                 760                 765

Ala Lys Lys Ala Pro Lys Glu Asp Val Asp Ala Val Lys Gln Leu
770                 775                 780
```

-continued

```
Leu Ser Leu Lys Ala Glu Tyr Lys Glu Lys Thr Gly Gln Glu Tyr Lys
785                 790                 795                 800

Pro Gly Asn Pro Pro Ala Glu Ile Gly Gln Asn Ile Ser Ser Asn Ser
            805                 810                 815

Ser Ala Ser Ile Leu Glu Ser Lys Ser Leu Tyr Asp Glu Val Ala Ala
        820                 825                 830

Gln Gly Glu Val Val Arg Lys Leu Lys Ala Glu Lys Ser Pro Lys Ala
    835                 840                 845

Lys Ile Asn Glu Ala Val Glu Cys Leu Leu Ser Leu Lys Ala Gln Tyr
850                 855                 860

Lys Glu Lys Thr Gly Lys Glu Tyr Ile Pro Gly Gln Pro Pro Leu Ser
865                 870                 875                 880

Gln Ser Ser Asp Ser Ser Pro Thr Arg Asn Ser Glu Pro Ala Gly Leu
            885                 890                 895

Glu Thr Pro Glu Ala Lys Val Leu Phe Asp Lys Val Ala Ser Gln Gly
        900                 905                 910

Glu Val Val Arg Lys Leu Lys Thr Glu Lys Ala Pro Lys Asp Gln Val
    915                 920                 925

Asp Ile Ala Val Gln Glu Leu Leu Gln Leu Lys Ala Gln Tyr Lys Ser
930                 935                 940

Leu Ile Gly Val Glu Tyr Lys Pro Val Ser Ala Thr Gly Ala Glu Asp
945                 950                 955                 960

Lys Asp Lys Lys Lys Lys Glu Lys Asn Lys Ser Glu Lys Gln Asn
            965                 970                 975

Lys Pro Gln Lys Gln Asn Asp Gly Gln Arg Lys Asp Pro Ser Lys Asn
        980                 985                 990

Gln Gly Gly Gly Leu Ser Ser Ser Gly Ala Gly Glu Gly Gln Gly Pro
    995                 1000                1005

Lys Lys Gln Thr Arg Leu Gly Leu Glu Ala Lys Lys Glu Glu Asn Leu
1010                1015                1020

Ala Asp Trp Tyr Ser Gln Val Ile Thr Lys Ser Glu Met Ile Glu Tyr
1025                1030                1035                1040

His Asp Ile Ser Gly Cys Tyr Ile Leu Arg Pro Trp Ala Tyr Ala Ile
            1045                1050                1055

Trp Glu Ala Ile Lys Asp Phe Phe Asp Ala Glu Ile Lys Lys Leu Gly
        1060                1065                1070

Val Glu Asn Cys Tyr Phe Pro Met Phe Val Ser Gln Ser Ala Leu Glu
    1075                1080                1085

Lys Glu Lys Thr His Val Ala Asp Phe Ala Pro Glu Val Ala Trp Val
1090                1095                1100

Thr Arg Ser Gly Lys Thr Glu Leu Ala Glu Pro Ile Ala Ile Arg Pro
1105                1110                1115                1120

Thr Ser Glu Thr Val Met Tyr Pro Ala Tyr Ala Lys Trp Val Gln Ser
            1125                1130                1135

His Arg Asp Leu Pro Ile Lys Leu Asn Gln Trp Cys Asn Val Val Arg
        1140                1145                1150

Trp Glu Phe Lys His Pro Gln Pro Phe Leu Arg Thr Arg Glu Phe Leu
    1155                1160                1165

Trp Gln Glu Gly His Ser Ala Phe Ala Thr Met Glu Glu Ala Ala Glu
1170                1175                1180

Glu Val Leu Gln Ile Leu Asp Leu Tyr Ala Gln Val Tyr Glu Glu Leu
1185                1190                1195                1200

Leu Ala Ile Pro Val Val Lys Gly Arg Lys Thr Glu Lys Glu Lys Phe
```

```
                    1205                1210                1215
Ala Gly Gly Asp Tyr Thr Thr Thr Ile Glu Ala Phe Ile Ser Ala Ser
            1220                1225                1230

Gly Arg Ala Ile Gln Gly Gly Thr Ser His His Leu Gly Gln Asn Phe
        1235                1240                1245

Ser Lys Met Phe Glu Ile Val Phe Glu Asp Pro Lys Ile Pro Gly Glu
    1250                1255                1260

Lys Gln Phe Ala Tyr Gln Asn Ser Trp Gly Leu Thr Thr Arg Thr Ile
1265                1270                1275                1280

Gly Val Met Thr Met Val His Gly Asp Asn Met Gly Leu Val Leu Pro
            1285                1290                1295

Pro Arg Val Ala Cys Val Gln Val Val Ile Ile Pro Cys Gly Ile Thr
        1300                1305                1310

Asn Ala Leu Ser Glu Glu Asp Lys Glu Ala Leu Ile Ala Lys Cys Asn
    1315                1320                1325

Asp Tyr Arg Arg Arg Leu Leu Ser Val Asn Ile Arg Val Arg Ala Asp
    1330                1335                1340

Leu Arg Asp Asn Tyr Ser Pro Gly Trp Lys Phe Asn His Trp Glu Leu
1345                1350                1355                1360

Lys Gly Val Pro Ile Arg Leu Glu Val Gly Pro Arg Asp Met Lys Ser
                1365                1370                1375

Cys Gln Phe Val Ala Val Arg Arg Asp Thr Gly Glu Lys Leu Thr Val
            1380                1385                1390

Ala Glu Asn Glu Ala Glu Thr Lys Leu Gln Ala Ile Leu Glu Asp Ile
        1395                1400                1405

Gln Val Thr Leu Phe Thr Arg Ala Ser Glu Asp Leu Lys Thr His Met
    1410                1415                1420

Val Val Ala Asn Thr Met Glu Asp Phe Gln Lys Ile Leu Asp Ser Gly
1425                1430                1435                1440

Lys Ile Val Gln Ile Pro Phe Cys Gly Glu Ile Asp Cys Glu Asp Trp
            1445                1450                1455

Ile Lys Lys Thr Thr Ala Arg Asp Gln Asp Leu Glu Pro Gly Ala Pro
        1460                1465                1470

Ser Met Gly Ala Lys Ser Leu Cys Ile Pro Phe Lys Pro Leu Cys Glu
    1475                1480                1485

Leu Gln Pro Gly Ala Lys Cys Val Cys Gly Lys Asn Pro Ala Lys Tyr
    1490                1495                1500

Tyr Thr Leu Phe Gly Arg Ser Tyr
1505                1510

<210> SEQ ID NO 64
<211> LENGTH: 34
<212> TYPE: PRT
<213> ORGANISM: Artificial Sequence
<220> FEATURE:
<223> OTHER INFORMATION: New Tat-Epep

<400> SEQUENCE: 64

Tyr Gly Arg Lys Lys Arg Arg Gln Arg Arg Gly Gly Lys Trp Asp
1               5                   10                  15

Val Ser Thr Thr Lys Ala Arg Val Ala Pro Glu Lys Lys Gln Asp Val
                20                  25                  30

Gly Lys

<210> SEQ ID NO 65
```

```
<211> LENGTH: 19
<212> TYPE: PRT
<213> ORGANISM: Artificial Sequence
<220> FEATURE:
<223> OTHER INFORMATION: 2+ EPRS peptide
<220> FEATURE:
<221> NAME/KEY: MOD_RES
<222> LOCATION: (16)
<223> OTHER INFORMATION: PHOSPHORYLATION,

<400> SEQUENCE: 65

Glu Tyr Ile Pro Gly Gln Pro Pro Leu Ser Gln Ser Ser Asp Ser Ser
1               5                   10                  15

Pro Thr Arg

<210> SEQ ID NO 66
<211> LENGTH: 19
<212> TYPE: PRT
<213> ORGANISM: Artificial Sequence
<220> FEATURE:
<223> OTHER INFORMATION: 2+ EPRS peptide

<400> SEQUENCE: 66

Glu Tyr Ile Pro Gly Gln Pro Pro Leu Ser Gln Ser Ser Asp Ser Ser
1               5                   10                  15

Pro Thr Arg

<210> SEQ ID NO 67
<211> LENGTH: 18
<212> TYPE: PRT
<213> ORGANISM: Artificial Sequence
<220> FEATURE:
<223> OTHER INFORMATION: 2+ EPRS peptide

<400> SEQUENCE: 67

Asn Gln Gly Gly Gly Leu Ser Ser Ser Gly Ala Gly Glu Gly Gln Gly
1               5                   10                  15

Pro Lys

<210> SEQ ID NO 68
<211> LENGTH: 18
<212> TYPE: PRT
<213> ORGANISM: Artificial Sequence
<220> FEATURE:
<223> OTHER INFORMATION: 2+ EPRS peptide
<220> FEATURE:
<221> NAME/KEY: MOD_RES
<222> LOCATION: (8)
<223> OTHER INFORMATION: PHOSPHORYLATION,

<400> SEQUENCE: 68

Asn Gln Gly Gly Gly Leu Ser Ser Ser Gly Ala Gly Glu Gly Gln Gly
1               5                   10                  15

Pro Lys

<210> SEQ ID NO 69
<211> LENGTH: 23
<212> TYPE: PRT
<213> ORGANISM: Artificial Sequence
<220> FEATURE:
<223> OTHER INFORMATION: 3+ EPRS peptide

<400> SEQUENCE: 69

Lys Asp Pro Ser Lys Asn Gln Gly Gly Gly Leu Ser Ser Ser Gly Ala
1               5                   10                  15
```

```
Gly Glu Gly Gln Gly Pro Lys
            20

<210> SEQ ID NO 70
<211> LENGTH: 23
<212> TYPE: PRT
<213> ORGANISM: Artificial Sequence
<220> FEATURE:
<223> OTHER INFORMATION: 3+ EPRS peptide
<220> FEATURE:
<221> NAME/KEY: MOD_RES
<222> LOCATION: (4)
<223> OTHER INFORMATION: PHOSPHORYLATION,

<400> SEQUENCE: 70

Lys Asp Pro Ser Lys Asn Gln Gly Gly Leu Ser Ser Ser Gly Ala
1               5                   10                  15

Gly Glu Gly Gln Gly Pro Lys
            20
```